(12) United States Patent
Kovacs et al.

(10) Patent No.: US 7,034,141 B2
(45) Date of Patent: Apr. 25, 2006

(54) PACKAGING OF POSITIVE-STRAND RNA VIRUS REPLICON PARTICLES

(75) Inventors: Gerald R. Kovacs, Rockville, MD (US); Nikos Vasilakis, Galveston, TX (US); Jacek Kowalski, Mahwah, NJ (US); Seema Gangolli, Park Ridge, NJ (US); Timothy Zamb, Nyack, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 42 days.

(21) Appl. No.: 10/363,082

(22) PCT Filed: Aug. 28, 2001

(86) PCT No.: PCT/US01/41888

§ 371 (c)(1),
(2), (4) Date: Aug. 27, 2003

(87) PCT Pub. No.: WO02/18585

PCT Pub. Date: Mar. 7, 2002

(65) Prior Publication Data

US 2004/0029279 A1 Feb. 12, 2004

Related U.S. Application Data

(60) Provisional application No. 60/228,906, filed on Aug. 29, 2000.

(51) Int. Cl.
*C07H 21/04* (2006.01)
*C12N 15/40* (2006.01)
*C12N 15/86* (2006.01)
*C12N 7/01* (2006.01)

(52) U.S. Cl. .............................. 536/23.72; 435/320.1; 435/456; 435/235.1

(58) Field of Classification Search ................ 435/456, 435/235.1; 424/93.1
See application file for complete search history.

(56) References Cited

U.S. PATENT DOCUMENTS 5,792,462 A    8/1998   Johnston et al.

OTHER PUBLICATIONS

Radecke, F. et al., "Rescue of measles virus from cloned DNA", 1995, EMBO Journal, vol. 14: pp. 5773-5784.*
Roberts, A. et al., "Recovery of Negative-Strand RNA Viruses from Plasmid DNAS: A Positive Approach Revitalizes a Negative Field", 1998, Virology, vol. 247: pp. 1-6.*
Frolov Ilya et al, Journal of Virology, vol. 71, No. 4: 2819-2829 (1997).
R. Hewson, Molecular Medicine Today, vol. 1, No. 6:28-35 (2000).
P. Pushko, et al, Virology, vol. 239:389-401 (1997).
Frolov Ilya et al, Proceedings of the National Academy of Sciences of the United States, vol. 93, No. 21:11371-11377 (1996).
P. Berglund, et al., Trends in Biotechnology, vol. 14, No. 4:130-134 (1996).

* cited by examiner

*Primary Examiner*—David Guzo
*Assistant Examiner*—Michael D. Burkhart
(74) *Attorney, Agent, or Firm*—Darrell Fontenot

(57) ABSTRACT

The invention generally relates to recombinant polynucleotides, positive-strand RNA virus (psRNAV) recombinant expression vectors, and packaging systems. The packaging systems are based on the expression of helper functions by coinfecting recombinant poxvirus vectors comprising recombinant polynucleotides. Methods for obtaining psRNAV replicon particles using these packaging systems are disclosed. Immunogenic compositions and pharmaceutical formulations are provided that comprise replicon particles of the invention. Methods for generating an immune response or producing a pharmaceutical effect are also provided.

37 Claims, 24 Drawing Sheets

```
CCTCCTGAAAAACTGGAATTTAATACACCATTTGTGTTCATCATCAGACATGATATTACTGGATT
TATATTGTTTATGGGTAAGGTAGAATCTCCTTAATATGGGTACGGTGTAAGGAATCATTATTTTA
TTTATATTGATGGGTACGTGAAATCTGAATTTTCTTAATAAATATTATTTTTATTAAATGTGTAT
ATGTTGTTTTGCGATAGCCATGTATCTACTAATCAGATCTATTAGAGATATTATTAATTCTGGTG
CAATATGACAAAAATTATACACTAATTAGCGTCTCGTTTCAGACATGGATCTGTCACGAATTAA
TACTTGGAAGTCTAAGCAGCTGAAAAGCTTTCTCTCTAGCAAAGATGCATTTAAGGCGGATGTC
CATGGACATAGTGCCTTGTATTATGCAATAGCTGATAATAACGTGCGTCTAGTATGTACGTTGTT
GAACGCTGGAGCATTGAAAAATCTTCTAGAGAATGAATTTCCATTACATCAGGCAGCCACATTG
GAAGATACCAAAATAGTAAAGATTTTGCTATTCAGTGGACTGGATGATTCGAGGTACCCGGGG
ATCCTCTAGAGTCAACCTTATTTATGATTATTTCTCGCTTTCAATTTAACACAACCCTCAAGAAC
CTTTGTATTTATTTTCAATTTTTAGCTGCAGGTGGATGCGATCATGACGTCCTCTGCAATGGATA
ACAATGAACCTAAAGTACTAGAAATGGTATATGATGCTACAATTTTACCCGAAGGTAGTAGCAT
GGATTGTATAAACAGACACATCAATATGTGTATACAACGCACCTATAGTTCTAGTATAATTGCC
ATATTGGATAGATTCCTAATGATGAACAAGGATGAACTAAATAATACACAGTGTCATATAATTA
AAGAATTTATGACATACGAACAAATGGCGATTGACCATTATGGAGAATATGTAAACGCTATTCT
ATATCAAATTCGTAAAAGACCTAATCAACATCACACCATTAATCTGTTTAAAAAAATAAAAAGA
ACCCGGTATGACACTTTTAAAGTGGATCCCGTAGAATTCGTAAAAAAAGTTATCGGATTTGTAT
CTATCTTGAACAAATATAAACCGGTTTATAGTTACGTCCTGTACGAGAACGTCCTGTACGATGA
GTTCAAATGTTTCATTGACTACGTGGAAACTAAGTATTTCTAAAATTAATGATGCATTAATTTTT
GTATTGATTCTCAATCCTAAAAACTAAAATATGAATAAGTATTAAACATAGCGGTGTACTAATT
GATTTAACATAAAAAATAGTTGTTAACTAATCATGAGGACTCTACTTATTAGATATATTCTTTGG
AGAAATGACAACGATCAAACCGGGCATGCAAGCTTGTCTCCCTATAGTGAGTCGTATTAGAGCT
TGGCGTAATCATGGTCATAGCTGTTTCCTGTGTGAAATTGTTATCCGCTCACAATTCCACACAAC
ATACGAGCCGGAAGCATAAAGTGTAAAGCCTGGGGTGCCTAATGAGTGAGCTAACTCACATTA
ATTGCGTTGCGCTCACTGCCCGCTTTCGAGTCGGGAAACCTGTCGTGCCAGCTGCATTAATGAA
TCGGCCAACGCGCGGGGAGAGGCGGTTTGCGTATTGGGCGCTCTTCCGCTTCCTCGCTCACTGA
CTCGCTGCGCTCGGTCGTTCGGCTGCGGCGAGCGGTATCAGCTCACTCAAAGGCGGTAATACGG
TTATCCACAGAATCAGGGGATAACGCAGGAAAGAACATGTGAGCAAAAGGCCAGCAAAAGGC
CAGGAACCGTAAAAAGGCCGCGTTGCTGGCGTTTTTCGATAGGCTCCGCCCCCCTGACGAGCAT
CACAAAAATCGACGCTCAAGTCAGAGGTGGCGAAACCCGACAGGACTATAAAGATACCAGGCG
TTTCCCCCTGGAAGCTCCCTCGTGCGCTCTCCTGTTCCGACCCTGCCGCTTACCGGATACCTGTC
CGCCTTTCTCCCTTCGGGAAGCGTGGCGCTTTCTCATAGCTCACGCTGTAGGTATCTCAGTTCGG
TGTAGGTCGTTCGCTCCAAGCTGGGCTGTGTGCACGAACCCCCCGTTCAGCCCGACCGCTGCGC
CTTATCCGGTAACTATCGTCTTGAGTCCAACCCGGTAAGACACGACTTATCGCCACTGGCAGCA
GCCACTGGTAACAGGATTAGCAGAGCGAGGTATGTAGGCGGTGCTACAGAGTTCTTGAAGTGG
TGGCCTAACTACGGCTACACTAGAAGGACAGTATTTGGTATCTGCGCTCTGCTGAAGCCAGTTA
CCTTCGGAAAAAGAGTTGGTAGCTCTTGATCCGGCAAACAAACCACCGCTGGTAGCGGTGGTTT
TTTTGTTTGCAAGCAGCAGATTACGCGCAGAAAAAAAGGATCTCAAGAAGATCCTTTGATCTTT
TCTACGGGGTCTGACGCTCAGTGGAACGAAAACTCACGTTAAGGGATTTTGGTCATGAGATTAT
CAAAAAGGATCTTCACCTAGATCCTTTTAAATTAAAAATGAAGTTTTAAATCAATCTAAAGTAT
ATATGAGTAAACTTGGTCTGACAGTTACCAATGCTTAATCAGTGAGGCACCTATCTCAGCGATC
TGTCTATTTCGTTCATCCATAGTTGCCTGACTCCCCGTCGTGTAGATAACTACGATACGGGAGGG
CTTACCATCTGGCCCCAGTGCTGCAATGATACCGCGAGACCCACGCTCACCGGCTCCAGATTTA
TCAGCAATAAACCAGCCAGCCGGAAGGGCCGAGCGCAGAAGTGGTCCTGCAACTTTATCCGCC
TCCATCCAGTCTATTAATTGTTGCCGGGAAGCTAGAGTAAGTAGTTCGCCAGTTAATAGTTTGC
GCAACGTTGTTGGCATTGCTACAGGCATCGTGGTGTCACGCTCGTCGTTTGGTATGGCTTCATTC
AGCTCCGGTTCCCAACGATCAAGGCGAGTTACATGATCCCCATGTTGTGCAAAAAGCGGTTA
GCTCCTTCGGTCCTCCGATCGTTGTCAGAAGTAAGTTGGCCGCAGTGTTATCACTCATGGTTATG
GCAGCACTGCATAATTCTCTTACTGTCATGCCATCCGTAAGATGCTTTTCTGTGACTGGTGAGTA
CTCAACCAAGTCATTCTGAGAATAGTGTATGCGGCGACCGAGTTGCTCTTGCCCGGCGTCAATA
CGGGATAATACCGCGCCACATAGCAGAACTTTAAAAGTGCTCATCATTGGAAAACGTTCTTCGG
GGCGAAAACTCTCAAGGATCTTACCGCTGTTGAGATCCAGTTCGATGTAACCCACTCGTGCACC
CAACTGATCTTCAGCATCTTTTACTTTCACCAGCGTTTCTGGGTGAGCAAAAACAGGAAGGCAA
AATGCCGCAAAAAAGGGAATAAGGGCGACACGGAAATGTTGAATACTCATACTCTTCCTTTTTC
AATATTATTGAAGCATTTATCAGGGTTATTGTCTCATGAGCGGATACATATTTGAATGTATTTAG
```

Figure 18A

```
AAAAATAAACAAATAGGGGTTCCGCGCACATTTCCCCGAAAAGTGCCACCTGACGTCTAAGAA
ACCATTATTATCATGACATTAACCTATAAAAATAGGCGTATCACGAGGCCCTTTCGTCTCGCGC
GTTTCGGTGATGACGGTGAAAACCTCTGACACATGCAGCTCCCGGAGACGGTCACAGCTTGTCT
GTAAGCGGATGCCGGGAGCAGACAAGCCCGTCAGGGCGCGTCAGCGGGTGTTGGCGGGTGTCG
GGGCTGGCTTAACTATGCGGCATCAGAGCAGATTGTACTGAGAGTGCACCATATGCGGTGTGAA
ATACCGCACAGATGCGTAAGGAGAAAATACCGCATCAGGCGCCATTCGCCATTCAGGCTGCGC
AACTGTTGGGAAGGGCGATCGGTGCGGGCCTCTTCGCTATTACGCCAGCTGGCGAAAGGGGGA
TGTGCTGCAAGGCGATTAAGTTGGGTAACGCCAGGGTTTTCCCAGTCACGACGTTGTAAAACGA
CGGCCAGTGAATTGGATTTAGGTGACACTATAGAATACGAATTC
```

Figure 18B

Confluent cultures of VERO cells were infected with IMVA3 indicator virus (Panels A and C), and/or VRPgD replicons (Panels B and C). Cells were observed with UV fluorescence microscopy at 24 hpi.

PACKAGING OF POSITIVE-STRAND RNA VIRUS REPLICON PARTICLES

FIELD OF THE INVENTION

The present invention generally relates to recombinant polynucleotides, positive-strand RNA virus recombinant expression vectors, and packaging systems. The packaging systems are based on the expression of split-helper functions by coinfecting cells with recombinant vectors, such as recombinant poxvirus vectors.

BACKGROUND OF THE INVENTION

Recombinant DNA technology has now made it possible to use viruses to introduce virtually any gene of interest into almost any cell of interest. Because such viruses are engineered to "express" the gene of interest, i.e., produce the protein encoded by the gene, they are called "viral expression vectors".

Recent attention has focused on alphaviruses, which are positive-strand RNA viruses (viruses whose nucleic acid is in the form of RNA, rather than DNA) that are transmitted to mammals via arthropods (reviewed in (16) and (17)). Positive strand RNA viruses, and in particular, alphaviruses, are especially attractive viral expression vectors for several reasons: 1) their genomes are easily manipulated in cDNA form and are infectious as naked RNA, 2) their replication cycle is exclusively cytoplasmic, 3) foreign gene expression is driven by a strong viral promoter, and 4) they have a broad host-range in vitro.

Structurally, as set forth in FIG. 1, the alphavirus genome is a single-stranded RNA, approximately 11.7 kilobases (kb) long, that is "capped" at the 5' end and "polyadenylated" at the 3' end. The two-thirds of the genome at the 5' end encodes nonstructural proteins (nsPs), and the one third at the 3' end encodes structural proteins (sPs). FIG. 1 also shows that the nonstructural proteins are responsible for both replication (copying) of the entire RNA sequence as well as transcription of a "subgenomic" RNA that leads to translation of the structural proteins (for review see (32) and (34)).

For replication, the nsPs are translated directly from the infecting viral genome, designated (+) RNA, as set forth in step 1 of FIG. 1 (steps are indicated by dark circles that contain numbers). The translation of the nsPs yields four proteins that form a "replication/transcription complex", comprising a "replicase" and a "transcriptase." The replicase/transcriptase mediates the synthesis of a genome-length complementary strand, designated (−) RNA, which is also termed the "antigenome", as set forth in step 2. In step 3, the replicase/transcriptase then creates an additional copy of (+) full-length RNA using the antigenome as a template.

The antigenome also serves as the template for transcription of the last third of the genome into subgenomic mRNA, as indicated in the step prior to step 4. As noted above, the 3' one-third of the genome encodes sPs and, accordingly, the subgenomic mRNA encodes the sPs. The sPs are encoded in the form of a large "polyprotein" that is then processed to yield a capsid protein and two envelope proteins, which are designated E1 and E2. The transcription of the subgenomic segment is mediated by nucleotides that span the junction between the nsP coding region and the sP coding region, and serve as a "promoter". Transcription from the subgenomic promoter can yield levels of subgenomic mRNA that can reach $10^6$ copies/cell, resulting in $10^8$ viral structural proteins per infected cell (30).

Once the envelope proteins and capsid proteins are synthesized, as per step 4, the capsid protein interacts with the replicated genome RNA to form a "nucleocapsid", which is then packaged by the envelope proteins. "Packaging signals" that are located within the nsP coding sequence of the genomic RNA serve to facilitate this process. Because the subgenomic RNA lacks these packaging signals, only the genomic RNA is encapsidated.

Viruses in the Togaviridae and Flaviviridae have similar enveloped, icosahedral nucleocapsid structures, and are believed to have evolved from a common ancestral virus (54). Alphaviruses and rubiviruses (eg. rubella virus), both members of the Togaviridae family, have similar genomic structures and replication cycles (see FIG. 22). The replicase/transcriptase complex is translated directly from the 5'-end of the genome, and the sPs are transcribed downstream from a subgenomic promoter present on the antisense RNA. Viruses in the Flaviviridae (eg. Dengue virus, hepatitis C virus, tick-borne encephalitis virus), all have common genome organizations and replication strategies. Unlike the togaviruses, flavivirus genomes serve as the mRNA for a polyprotein that encodes both the sPs and the nSPs. The expression of these gene products is regulated at post-translational steps; there is no subgenomic transcription in the Flaviviridae. Furthermore, the gene arrangement is inverted, i.e., the sP genes are located upstream of the nSPs. Although these viruses differ in their genomic arrangement and replication strategies, they can be substituted for the viruses described herein. For example, they can be engineered into replicon expression vectors by removing the sPs coding region ((55), (56)), and packaged into virus-like particles by providing the sPs in trans (57), using techniques substantially similar to those described herein.

Other positive strand RNA viruses that have been engineered as either live and/or replication-defective expression vectors include poliovirus (58) and coronavirus (59). Although they also differ from the alphaviruses, replicon vectors derived from these viruses may be packaged using techniques similar to those described herein.

Understanding the replication/transcription processes of the alphaviruses, as well as their nucleic acid sequence, has permitted their use as expression vectors. Several alphaviruses have been sequenced, and infectious cDNA clones have also been engineered for Sindbis virus (SV; (31)), Semliki Forest virus (SFV; (20)), Venezuelan equine encephalitis virus (VEE; (11)), and Ross River virus (RRV; (18)). Vectors based on SV, SFV and VEE have shown promise as effective gene expression systems (for reviews see (14), (21), (15)).

There are, in general, two types of alphavirus expression vectors. In one type of vector, the "replication-competent" vector, a second subgenomic promoter is added to direct the expression of a foreign (heterologous) gene. This type of double-subgenomic promoter vector expresses the foreign gene of interest, as well as all the structural components needed for viral packaging; thus, these vectors are self-replicating and self-packaging. The apparent disadvantage of such a system is the production of viable virus.

To minimize the potential production of a viable virus, the alphavirus expression vectors have been further engineered to be "replication-defective." These vectors are created by removing the genes that encode for sPs, and substituting one or more foreign genes under the control of the subgenomic promoter. Since the nsP coding sequence remains intact, these vectors can form the replication complex and self-replicate and express the foreign gene(s). They are not self-packaging, however, because they lack the sPs which encode the capsid and envelope proteins. To package these vectors into infectious particles, the vectors can be complemented "in trans" with "helper" vectors, i.e., vectors that bear the sPs on a separate RNA molecule. For example, these vectors may be packaged by cotransfecting the vector with in vitro transcribed defective-helper (DH) RNAs that encode the viral capsid and glycoproteins (19), (5) or, alternatively, by transfecting the replicon RNA into a continuous packaging cell line which expresses DH RNAs under the regulation of a nuclear promoter (26). With either system, the helper RNA is either not packaged, or packaged with very low efficiency, since it lacks the packaging signal present within the nsP coding region.

Recombination frequently occurs, however, between alphavirus replication intermediates (including the replicon and DH RNAs) and can result in the creation of self-replication and self-packaging virus (35), (29), (37). This poses potential biosafety and regulatory concerns about the use of these packaging systems. To address these concerns, scientists have developed "split-helper" packaging systems which significantly decrease the probability of generating vectors that are able to replicate and self-package (14), (27), (33). The "split-helper" system uses two separate DH RNAs, one encoding the capsid protein and another encoding the viral glycoproteins (E2/E1). This is a costly and inefficient system, however, since the two separate DH RNAs must first be transcribed in vitro, purified, and subsequently inserted into a packaging cell that has been prepared for transfection. Numerous manipulations of the RNA and cells result in inconsistent production of replicon particles.

Cells infected with an alphavirus typically produce $10^{3-10}4$ infectious virus particles/cell. The production of replicon particles, by contrast, is much less efficient. Cells transfected with these vectors typically produce an average of 1–50 replicon particles per cell. The low yield of replicon particles is the result of the cumulative effects of poor in vitro transcription and cellular transfection. For example, successful expression of RNA that has been transcribed in vitro requires that the RNA be capped at the 5' end. For the split-helper systems, which contain two separate DH RNAs, there are three RNA segments that must be capped: both helper RNAs and the replicon itself. If the efficiency of the capping of the replicon in vitro is, for example, 65% and of each DH RNA is 85%, then the efficiency of the transfection is at best 42% (0.65×0.8×0.8). Thus, the efficiency of expression is limited by the efficiency of the three capping reactions and the transfection process.

Compounding the capping problem is the fact that transfection procedures using chemical reagents are relatively ineffective. Electroporation methods, where RNAs are introduced into cells using an electric field rather than chemicals, are more efficient, but they require numerous manipulations and rigorous optimizations. Additionally, electroporation methods have not yet been successfully used in large-scale preparations.

The ideal packaging system would entail using an efficient gene delivery system that is optimized for gene expression. Such a system can be based on plasmids or viral vectors (e.g., poxviruses, adenoviruses, herpesviruses, poliovirus, influenza viruses, retroviruses, etc.). Viral vectors can be used to infect a broad range of cell types in large-scale with great efficiency. Many viral vectors have been engineered for optimal gene expression and limited growth in specific cell lines.

Yet another potential limitation to using these replicon vectors is the lack of large-scale packaging systems for vector particles. The preparation of the reagents needed for packaging of, for example, alphavirus particles is costly, impractical, and not amenable to meaningful scale-up. Thus, there exists a need in the art for safe and cost-effective replicon expression vectors and packaging systems. Such vectors would be used to efficiently deliver and express psRNAV-derived RNAs for the large-scale production of infectious replicon particles for the purposes of subunit vaccine gene delivery, gene therapy, cancer immunotherapy, and recombinant protein synthesis.

SUMMARY OF THE INVENTION

The present invention is directed to infectious positive-strand RNA virus (psRNAV) replicon particles, recombinant positive-strand RNA virus expression vectors, and packaging systems for producing psRNAV replicon particles using recombinant poxvirus vectors. These packaging systems do not require the in vitro synthesis or transfection of viral RNAs. Instead, the methods and compositions of the invention use recombinant DNA viruses and/or plasmids to deliver to a cell the components required to assemble infectious psRNA replicon particles. Methods and compositions are provided, including immunogenic compositions and pharmaceutical formulations for administering to a host. Also provided are recombinant polynucleotides and vectors for creating poxvirus-based replicon particle packaging systems. Kits for use with the disclosed compositions and methods are provided.

Certain packaging systems of the invention are based on coinfection with a pair of recombinant poxvirus vectors whose expression products can package recombinant psRNAV replicon particles. This system produces infectious replicon particles, including at least one foreign gene (that is a gene that is taken out of its natural state), which may be a viral gene. In an exemplary embodiment, the pair of poxvirus vectors is based on a vaccinia virus, specifically, a severely host-restricted, attenuated strain of vaccinia virus (modified vaccinia virus Ankara, or MVA). In this embodiment, the psRNAV is an alphavirus, Venezuelan equine encephalitis virus (VEE). The pair of MVA vectors produce the VEE capsid and envelope proteins that thereafter package the VEE replicon RNA to produce an infectious VEE replicon particle (VRP).

The MVA-based VRP packaging systems rely on the production of replicon RNAs and helper proteins. The expression of the helper proteins is either inducible or constitutive based on the form of the RNAs transcribed by the MVA vector. Inducible helper RNAs are replicated and transcribed by the VEE replicase/transcriptase prior to being translated. Constitutive helper RNAs are transcribed as mRNAs and therefore are translated directly.

The replicon particle packaging systems of the invention yield greater titers of replicon particles than the conventional split-helper RNA transfection method discussed above. Using the packaging systems disclosed herein, helper function RNAs can be expressed either as DH RNAs, or as mRNAs, depending on the packaging system employed. The probability of generating self-replicating infectious virus during the replicon packaging process is further reduced in the constitutive system since all of the psRNAV regulatory sequences are absent from the helper RNAs. This system provides the greatest level of safety of all known packaging systems.

Additionally, the invention provides methods for using other poxvirus vectors in the large-scale production of recombinant gene products (2). These methods are amenable to adaptation for the mass-production of replicon particles.

The novel recombinant polynucleotides and recombinant vectors, including recombinant viruses, can be prepared using standard cloning and molecular biology techniques that are well known in the art. Descriptions of such techniques can be found, among other places, in Sambrook et al., Molecular Cloning (1989) (38) and Ausbel et al., Current Protocols in Molecular Biology (1993, including supplements (39)).

The invention is based upon recombinant polynucleotides that serve as components for recombinant vectors, including recombinant viruses, that in turn are components of replicon particle packaging systems. In certain embodiments, these recombinant viruses and packaging systems are used in methods of the invention to obtain replicon particles.

In certain embodiments, recombinant polynucleotides within the invention comprise at least a first portion and a second portion. The first portion includes a sequence with at least a first heterologous promoter that is operatively linked to a sequence that encodes a DNA-dependent RNA polymerase. By "operatively linked" is meant a linkage that permits regulatory control, such as a promoter that controls expression. The second portion includes a second heterologous promoter that is operatively linked to a sequence that encodes at least one psRNAV structural protein, but it does not encode all of the psRNAV structural proteins. Thus, the second portion may encode a psRNAV capsid or it may encode a psRNAV glycoprotein, but not both. The terms first portion and second portion are not intended to indicate any sequential position within the recombinant polynucleotides. Thus the first portion may be either upstream or downstream of the second portion.

Further, the terms first portion and second portion are not intended to be limiting. For example, in certain embodiments the recombinant polynucleotides comprise three or more portions. For instance, a second portion may comprise a sequence that encodes an E1 glycoprotein and a third portion may comprise a sequence that encodes an E2 glycoprotein.

The promoters of the first and second portions may be the same or different. In the first portion, the DNA-dependent RNA polymerase to which the first heterologous promoter is attached may be a viral or bacteriophage polymerase, for example, without limitation, a bacteriophage T3, T7, or SP6 DNA-dependent RNA polymerase.

In certain embodiments, the first and second heterologous promoters are different. For example, without limitation, the first promoter may comprise a poxvirus promoter and the second promoter comprise a bacteriophage promoter. In one exemplary embodiment, the recombinant polynucleotide has a vaccinia virus synthetic early/late promoter operatively linked to a sequence encoding bacteriophage T7 DNA-dependent RNA polymerase, and a second heterologous promoter, that binds to T7 DNA-dependent RNA polymerase, operatively linked to a sequence encoding at least one psRNAV structural protein, such as a Venezuelan equine encephalitis virus glycoprotein.

In certain embodiments of the invention, recombinant polynucleotides comprise a first portion which includes a first heterologous promoter operatively linked to a sequence encoding at least one, but not all, of the psRNAV structural proteins. Thus, the first portion will contain a sequence encoding either the psRNAV capsid protein or a psRNAV glycoprotein, but not both. The second portion includes a second heterologous promoter operatively linked to a psRNAV "replicon" which is capable of replication. The psRNAV replicon of the second portion includes a psRNAV subgenomic promoter operatively linked to a sequence encoding at least one foreign polypeptide. In certain embodiments, the first and second heterologous promoters may bind the same polymerase, for example, but not limited to, T7 DNA-dependent RNA polymerase, or they may bind different polymerases, for example, but without limitation, DNA-dependent RNA polymerases from poxvirus or bacteriophage T3, T7, or SP6. In certain embodiments, the psRNAV is an alphavirus.

In one exemplary embodiment, the recombinant polynucleotide has a bacteriophage T7 promoter operatively linked to a sequence encoding an alphavirus capsid protein, and a second T7 promoter operatively linked to a sequence encoding an alphavirus replicon. In certain embodiments, the alphavirus capsid and alphavirus replicon are from Venezuelan equine encephalitis virus.

In yet other embodiments, the recombinant polynucleotide has a first portion which includes a first heterologous promoter operatively linked to a sequence encoding a DNA-dependent RNA polymerase. The second portion includes a sequence encoding a replicon-like psRNAV helper RNA operatively linked to a second heterologous promoter. Thus, when a DNA-dependent RNA polymerase binds to the second heterologous promoter, a replicon-like psRNAV helper RNA is transcribed. When the replicon-like helper RNA is exposed to the psRNAV replication complex, it is replicated by the replicase to produce an "antigenomic" strand that is transcribed by the transcriptase to produce a subgenomic transcript. The subgenomic transcript is then translated to produce either a psRNAV capsid protein or a psRNAV glycoprotein, but not both.

In these embodiments, the sequence encoding a DNA-dependent RNA polymerase encodes a bacteriophage polymerase, such as from bacteriophage T3, T7, SP6, or the like, and the replicon-like helper sequence comprises the sequence encoding a psRNAV capsid In these embodiments, the first heterologous promoter comprises, for example, a poxvirus synthetic early/late promoter, and the second heterologous promoter binds to a bacteriophage DNA-dependent RNA polymerase, such as T3, T7, or SP6 polymerase.

In other embodiments, recombinant polynucleotide has a vaccinia virus synthetic early/late promoter operatively linked to a sequence encoding a bacteriophage T7 polymerase; and a second heterologous promoter, that binds to a T7 DNA-dependent RNA polymerase, is operatively linked to a replicon-like helper sequence comprising a sequence encoding a psRNAV capsid.

In yet other embodiments, a recombinant polynucleotide of the invention has a first portion including a sequence encoding a replicon-like psRNAV helper RNA operatively linked to a first heterologous promoter; and a second portion comprising a second heterologous promoter operatively linked to a psRNAV replicon. The psRNAV replicon includes a psRNAV subgenomic promoter operatively linked to a sequence encoding at least one foreign polypeptide. In these embodiments, the first and second heterologous promoters may be the same or they may be different. In certain embodiments, the replicon-like helper sequence comprises a sequence encoding a psRNAV glycoprotein. In certain embodiments, the first and second heterologous promoters binds to a bacteriophage DNA-dependent RNA polymerase, for example, without limitation, T3, T7, or SP6 polymerase. In certain embodiments, the psRNAV is an alphavirus.

In one exemplary embodiment, the first and second promoters of the recombinant polynucleotide bind to a T7 DNA-dependent RNA polymerase, and the replicon-like helper sequence comprises a sequence encoding an alphavirus glycoprotein, for example, but not limited to, Venezuelan equine encephalitis virus glycoprotein.

Once the recombinant polynucleotides discussed above have been generated, they can be used to create recombinant vectors, such as but not limited to, a cloning vector or expression vector. Exemplary cloning vectors or expression vectors include bacterial plasmids, phagemids, recombinant viruses, yeast vectors, and the like. Favorable attributes of cloning vectors may include ease of cloning and in vitro manipulations. Favorable attributes of expression vectors may include robust gene expression, broad host-range of infectivity, limited growth or no growth in restrictive cell lines, infectious to mammalian host cells, control of host-cell antiviral responses, nonpathogenic to laboratory personnel. Preferred recombinant plasmid or virus vectors include poxviruses, adenoviruses, herpesviruses, poliovirus, influenza viruses, and retroviruses. A particularly preferred recombinant poxvirus vector is modified vaccinia virus Ankara (MVA).

In certain embodiments, for biosafety reasons, the packaging systems of the invention may comprise three recombinant vectors, each encoding a different psRNAV structural polypeptide. In certain embodiments, the three recombinant vectors include, but are not limited to, a first recombinant vector comprising a sequence encoding a capsid, a second recombinant vector comprising a sequence encoding an E1 glycoprotein, and a third recombinant vector comprising a sequence encoding an E2 glycoprotein.

The skilled artisan will understand that the recombinant virus vectors used in the packaging systems of the invention may, but need not, be derived from the same recombinant virus. For example, with certain virus systems, infection by a first virus may cause the infected cell to become refractory to superinfection by another virus from the same virus system. Thus, in certain embodiments, it may be preferred to employ a packaging system wherein the first recombinant virus is derived from a different virus system than the second recombinant virus. For example, but not limited to, a packaging system comprising a poxvirus-derived vector and an adenovirus-derived vector.

Additionally, double-promoter insertion/expression vectors can be used. For example, the synthetic early/late promoter of vaccinia virus has been engineered in a back-to-back configuration so that two genes can be inserted simultaneously into the same site of the poxvirus (50). This same type of vector could also be used to insert multiple expression cassettes in the MVA packaging systems.

In certain embodiments, recombinant MVAs comprise one or more recombinant polynucleotides of the invention inserted into MVA deletions II or III (See FIG. 2). In other embodiments, recombinants comprise one or more recombinant polynucleotides of the invention inserted into the MVA hemagglutinin gene (42), the thymidine kinase gene (52), or into other nonessential regions of the MVA genome. Insertions into other MVA deletion sites are also within the scope of the invention. For example, six MVA deletions have been mapped, including deletion I, a 2.9 kilobasepair (kbp) deletion within the HindIII C restriction fragment; deletion II, a 5.0 kbp deletion within the HindIII N restriction fragment; deletion III, a 3.5 kbp deletion within the HindIII A restriction fragment; deletion IV, a 10.2 kbp deletion within the HindIII B restriction fragment; deletion V, a 4.7 kbp deletion within the HindIII C fragment; and deletion VI, a 3.8 kbp deletion within the HindIII A restriction fragment (See FIG. 2 for HindIII restriction map). Descriptions of the mapping of MVA deletions can be found, among other places, in references (41), (49) and (51).

Replicon packaging systems are also provided. The novel packaging systems disclosed herein comprise at least two recombinant vectors of the invention. The packaging systems of the invention may be inducible or constitutive. An exemplary psRNAV replicon packaging system comprises two recombinant MVAs, each of which has a first and second portion. A first exemplary recombinant MVA has a first portion that comprises a vaccinia virus synthetic early/late promoter operatively linked to a sequence encoding bacteriophage T7 DNA-dependent RNA polymerase, and a second portion that comprises a second heterologous promoter that binds to T7 DNA-dependent RNA polymerase, operatively linked to a sequence encoding at least one alphavirus structural protein inserted into deletion III, wherein that sequence encodes VEE glycoprotein (see FIG. 2). A second exemplary recombinant MVA has a first portion comprising a bacteriophage T7 promoter operatively linked to a sequence encoding a Venezuelan equine encephalitis virus capsid protein inserted into deletion III, and a second portion comprising a T7 promoter operatively linked to a sequence encoding a VEE replicon, inserted into deletion II (see FIG. 2).

Methods for producing infectious replicon particles are also provided. According to certain embodiments, cells are coinfected with recombinant viruses comprising a novel replicon particle packaging system of the invention. In one exemplary embodiment, cells are coinfected with one or more MVA recombinant viruses comprising a novel replicon particle packaging system of the invention. In another exemplary embodiment, methods of amplifying infectious replicon particles are provided. Cells are coinfected with psRNAV replicon particles and MVA recombinant(s) that express psRNAV capsid and glycoproteins. In both exemplary embodiments, the coinfected cells are incubated under appropriate conditions for replicon particles to be generated. Once generated, the replicon particles are obtained.

Methods of titering replicon particles are provided. According to certain embodiments, cells are infected with an MVA recombinant that delivers to the cell a suitable reporter gene. When a cell is coinfected with a replicon particle, the reporter gene is activated, and the cell can then be detected. Examples of reporter genes that may be used with this system include green fluorescent protein, blue fluorescent protein, yellow fluorescent protein, beta-galactosidase, beta-glucoronidase choramphenicol acetyl-transferase, and luciferase.

The replicon particles of the invention may be used in immunogenic compositions or pharmaceutical formulations to be administered to a host. Such compositions and formulations may further comprise appropriate physiologically acceptable carriers, adjuvants, diluents, excipients, immunostimulatory compounds, and the like. These compositions and formulations may be administered using any effective method. Exemplary administration methods include, intravenous, intramuscular, or intradermal injection, intranasal instillation, orally, topical application to a dermal or mucosal surface, and the like.

In certain embodiments, methods for inducing an immune response in a mammalian or human host are provided. Such methods comprise administering to the host an immunologically effective amount of an immunogenic composition of the invention to induce an immune response in the host. In certain embodiments, methods for producing a prophylactic, therapeutic, or palliative effect in a mammalian or human host are provided. These methods comprise administering to the host an effective amount of a pharmaceutical formulation of the invention to produce a prophylactic, therapeutic, or palliative effect.

Also within the scope of the invention are foreign proteins that are expressed by the recombinant polypeptides; recombinant vectors, including recombinant viruses; replicon particle packaging systems of the invention; and replicon particles obtained using the methods of the invention.

BRIEF DESCRIPTION OF THE DRAWINGS

FIG. 18. Depicts the nucleotide sequence of vector pLW17 (obtained from B. Moss), see Example 1B. (SEQ ID NO: 3)

DETAILED DESCRIPTION OF THE PREFERRED EMBODIMENTS

Figure 1:
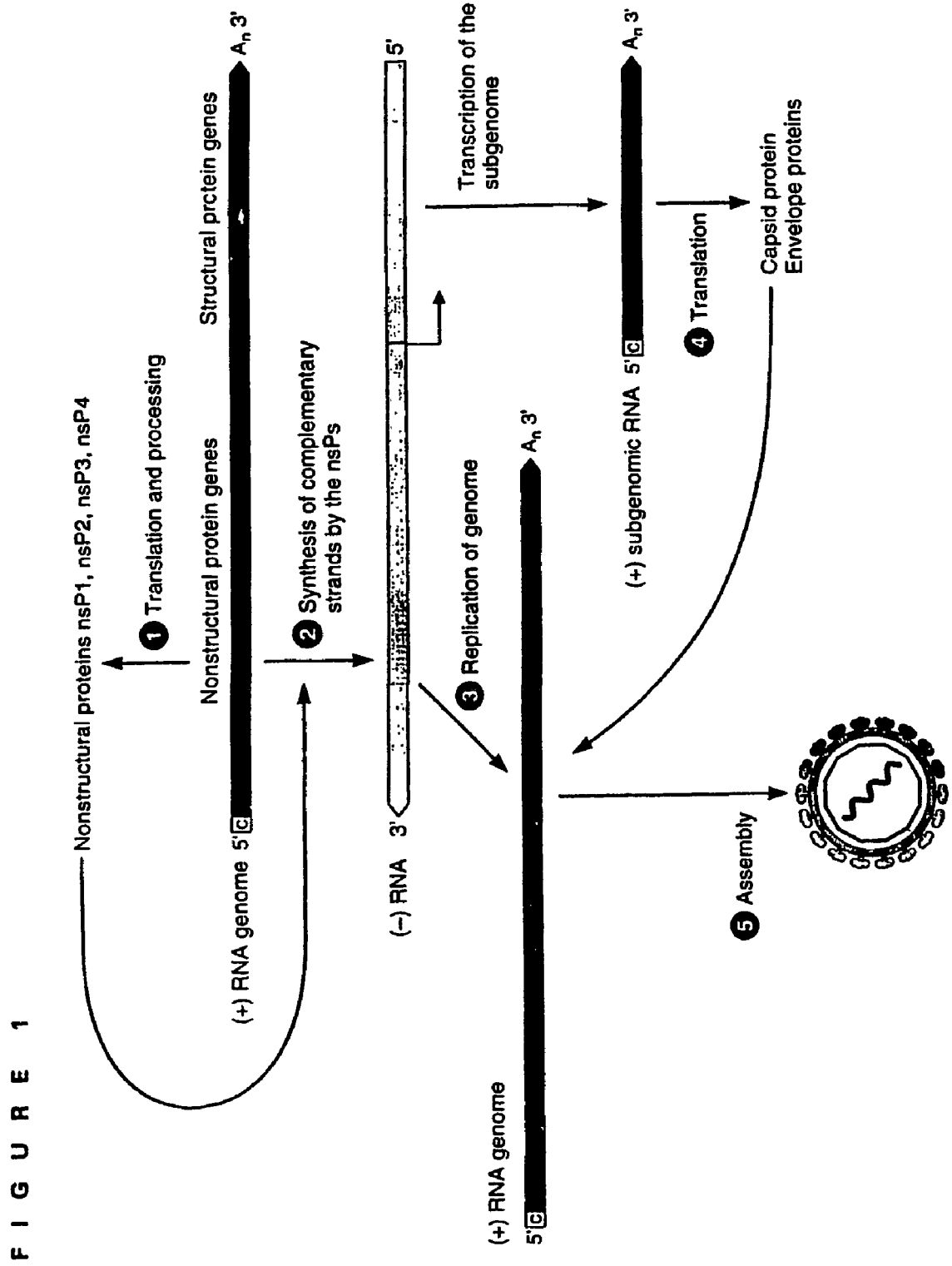
FIG. 1. Schematic diagram showing the steps of the alphavirus replication cycle. Within the infected cell, the 5' two-thirds of the alphavirus genome is translated, from a single translation initiation site, to generate the four alphavirus nonstructural proteins (nsPs) (step 1). The nsPs are required for the synthesis of the complementary (−) RNA strand (step 2) that serves as the template for replicating the genomic RNA and transcription of the subgenomic RNA (step 3). The subgenomic RNA is translated to produce the structural proteins (sPs) (step 4) that interact with the packaging signals on the genomic RNA, but not the subgenomic RNA, to assemble infectious alphavirus particles (step 5). The horizontal arrow shown on the complementary (−) RNA strand indicates the alphavirus subgenomic promoter. (Figure from Schiessinger, S. 1999. ASM News 65:688–95.)

The section headings used herein are for organizational purposes only and are not to be construed as limiting the subject matter described. All references cited in this application, including articles, books, patents, and patent applications, are expressly incorporated by reference for any purpose.

Definitions

As used herein, the term "positive-strand RNA virus" or "psRNAV" refers to RNA viruses that exist as a positive-strand RNA. Positive-strand RNA viruses include, but are not limited to, alphaviruses, including but not limited to Ross River virus, Semliki forest virus, Sindbis virus, and Venezuelan equine encephalitis virus; flaviviruses, including but not limited to Dengue virus; hepaciviruses, including but not limited to Hepatitus C virus; coronaviridae, including but not limited to coronavirus; and rubiviruses, including but not limited to rubella virus.

The term "glycoprotein" encompasses the alphavirus glycoproteins, as well as the functionally homologous proteins of other positive-strand RNA viruses. The term "glycoprotein" when used in reference to alphavirus proteins or genes, are both used in a broad sense, encompassing the alphavirus E1 glycoprotein, the alphavirus E2 glycoprotein, the alphavirus E2/E1 glycoprotein precursor, and/or an alphavirus polyprotein comprising E3/E2/6K/E1, or combinations thereof.

The term "replicon" refers to a replication-defective psRNAV that has at least one foreign gene inserted into the psRNAV genome in place of the sequence that encodes the psRNAV structural proteins. The at least one foreign gene is operatively linked to, and is thus transcriptionally regulated by, the psRNAV subgenomic promoter. In certain embodiments, the inserted foreign gene replaces only some of the sequence encoding the psRNAV structural proteins. Thus, the replicon encodes both a foreign gene and some, but not all, of the psRNAV structural proteins.

The term "defective helper RNA," also referred to as "DH RNA," describes an RNA that has been designed to contain cis-acting sequences essential for replication, and a subgenomic promoter for transcription of one or more structural protein genes. Expression of the structural proteins is achieved by providing the psRNAV replicase/transcriptase in trans.

The term "foreign gene" when used herein refers to a nucleic acid sequence that has been removed form its natural genetic environment and placed into a different genetic environment. For example, but not limited to, a gene encoding a human amyloid peptide that is operatively linked to an alphavirus subgenomic promoter, or a Sindbis virus glycoprotein gene operatively linked to a subgenomic promoter from Venezuelan equine encephalitis. The term "foreign polypeptide," as used herein refers to a polypeptide that is encoded by a foreign gene.

As used herein, the term "immunogenic composition" refers to one or more substances that stimulate or enhance a humoral or cellular immune response. Examples of such immunogenic compositions include, but are not limited to, antigens, T-cell epitopes, peptides or nucleotides that stimulate or enhance an immune response.

The term "operatively linked" refers to a promoter and coding sequence combination wherein the promoter transcriptionally regulates the expression of the coding sequence. The term "heterologous promoter", as used herein, refers to a promoter that is operatively linked to a different coding sequence than the promoter is naturally associated with. Exemplary heterologous promoters may be prokaryotic, eukaryotic, or viral, and include, but are not limited to, poxvirus promoters, including vaccinia virus synthetic early/late promoters, bacteriophage T7, T3, and SP6 promoters, cytomegalovirus (CMV) promoters, Rous sarcoma virus (RSV) promoters, MMTV promoters, Murine leukemia virus promoters, mammalian pol I promoters, mammalian pol II promoters, and mammalian pol III promoters. Exemplary heterologous promoters also include inducible promoters, such as estrogen-responsive promoters, tetracycline-responsive promoters, metallothionein promoters, calcium-responsive promoters, and lac promoters. In certain embodiments, an operatively linked heterologous promoter is a vaccinia virus promoter operatively linked to a bacteriophage coding sequence. Certain embodiments provide a bacteriophage promoter operatively linked to an alphavirus coding sequence.

The term "pharmaceutical formulation", as used herein, refers to one or more substances that, when provided to a host in an effective amount, produces a prophylactic, therapeutic, or palliative effect in the host. Pharmaceutical formulations may or may not stimulate an immune response in the host. Examples of such pharmaceutical formulations include, without limitation, alphavirus replicon particles encoding insulin, growth hormone, monokines, cytokines, virokines, or other genes that are desirable for gene therapy.

The term "polymerase" refers to an enzyme that can synthesize nucleic acid polymers from nucleotides in a template-dependent manner. The nucleic acid polymer that is produced is complementary to the template. Polymerases that synthesize RNA polymers are referred to as RNA polymerase while polymerases that synthesize DNA polymers are referred to as DNA polymerase. Additionally, polymerases are categorized based on whether they function using a DNA template or a RNA template. Thus, for example, a DNA-dependent RNA polymerase synthesizes a complementary RNA copy using a DNA template.

The term "polypeptide", as used herein, refers to two or more amino acids linked together by at least one peptide bond. The term is used in a general sense to include peptides, oligopeptides, and proteins.

The term "replicon-like helper RNA" refers to a sequence that is transcribed to produce a helper RNA template upon which a psRNAV replication complex can act. One element in the psRNAV replication complex, the psRNAV replicase, uses the helper RNA template to synthesize a single-stranded, negative-sense "antigenome". That antigenome serves serves as a template for another element of the replication complex, the psRNAV transcriptase. The transcriptase synthesizes a mRNA that, when translated, produces either a psRNAV capsid protein or a psRNAV glycoprotein, but not both.

The term "synthetic early/late promoter" refers to a nucleotide sequence that is useful as a transcriptional promoter and that has been genetically optimized for expression based on detailed mutagenesis of a family of promoters (e.g. vaccinia virus early or late promoters).

The term "transcription" refers to the process wherein a RNA polymerase synthesizes a complementary RNA copy of a DNA or RNA template.

The term "translation" refers to the process wherein proteins are synthesized by the translation complexes based on a RNA template, generally, mRNA.

Exemplary Embodiments of the Invention

The packaging systems of the invention are based on coinfection with two recombinant vectors bearing a psRNAV replicon and helper RNAs or genes. These systems do not require transfection of in vitro synthesized RNA molecules. To more clearly illustrate the invention, exemplary recombinant vector-based alphavirus replicon particle packaging systems were generated using a bacteriophage T7 DNA-dependent RNA polymerase, a modified vaccinia virus (MVA) vector, and VEE. Both inducible and constitutive alphavirus replicon particle packaging systems are provided.

One difference between the two types of systems is in the structure of the helper function RNAs. In some exemplary inducible type systems, defective helper (DH) RNAs are transcribed by a T7 DNA-dependent RNA polymerase and subsequently expressed when replicated and transcribed in the presence of an inducer, VEE replicase. In some exemplary constitutive type systems, the helper functions are transcribed as mRNAs by the vaccinia virus DNA-dependent RNA polymerase, and are expressed throughout the course of infection, even in the absence of the VEE replicase. The constitutive packaging system can also be engineered to express the structural protein genes under the regulation of bacteriophage promoters.

Replicon particles are generated when a cell is coinfected with both of the recombinant vectors of the packaging system. The replicon particles that are generated are capable of initiating a single round of infection. However, the replicon particles cannot form viable virus because only replicon genomes containing the foreign gene(s) are packaged. This results from the creation of packaging systems that express replicons that contain packaging signals and helper RNAs that lack packaging signals.

Since the psRNAV replicon is not on the same recombinant viral vector as the T7 DNA-dependent RNA polymerase gene, the replicon is not expressed unless the second recombinant viral vector, containing the polymerase gene, is present in the cell. Further, only the replicon, not the helper RNAs, contain a packaging signal. Consequently, only the expressed replicon is packaged to produce infectious particles.

The skilled artisan will understand that DNA-dependent RNA polymerases obtained from sources other than bacteriophage T7 are within the scope of the invention, as are poxviruses and positive-strand RNA viruses, other than MVA and VEE. Further, in addition to the consensus nucleotide or amino acid sequences for a given polymerase, poxvirus, or psRNAV, sequences from variants, for example, additional clinical isolates or in vitro generated variant viruses, are contemplated in the invention. Additionally, due to the degeneracy of the nucleotide code, many different nucleotide sequences will encode the same amino acid sequence. Thus degenerate nucleotide sequences are within the intended scope of the invention.

Figure 3:
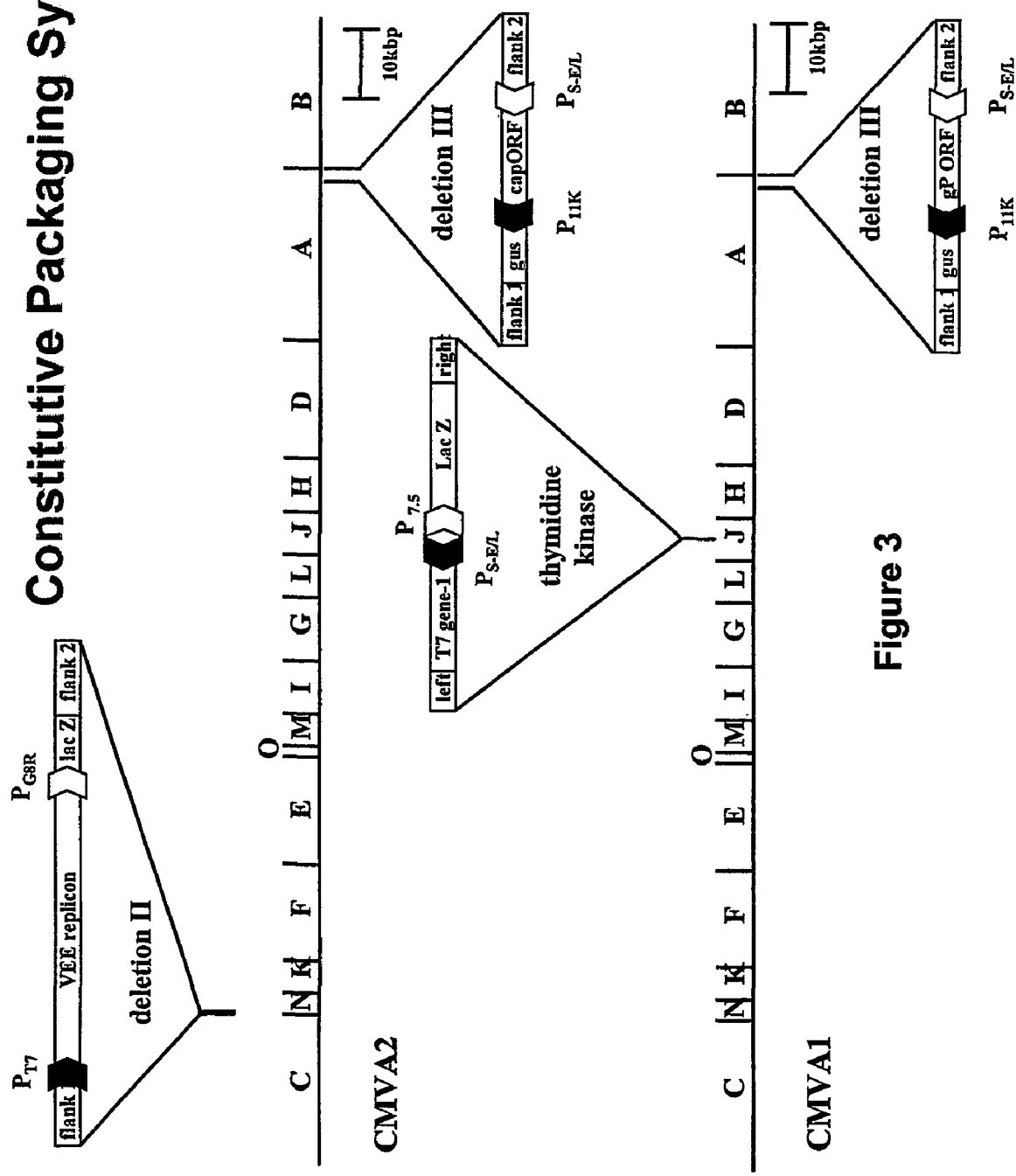
FIG. 3. Schematic representation of an exemplary alphavirus replicon particle constitutive packaging system. The HindIII restriction map is shown superimposed on CMVA1 and CMVA2. Abbreviations used in FIGS. 3 and 4—$P_{T7}$: bacteriophage T7 promoter; $P_{7.5}$: vaccinia 7.5K promoter; $P_{S-E/L}$: vaccinia synthetic early/late promoter; $P_{11K}$: vaccinia 11K promoter; $P_{G8R}$: G8R promoter; capORF: capsid open reading frame; gP ORF: glycoprotein open reading frame; DH gP: sequence encoding glycoprotein defective helper RNA; DHcap: sequence encoding capsid defective helper RNA.

In more detail, the constitutive packaging systems comprise two recombinant poxvirus vectors, which, for illustration purposes, are constitutive MVA vector 1 (CMVA1, also referred to as MVGKT7/gp) and constitutive MVA vector 2 (CMVA2, also referred to as MVA/VEEGFP/cap) (See FIG. 3). CMVA1 comprises the bacteriophage T7 gene-1, encoding a DNA-dependent RNA polymerase, operatively linked to a vaccinia virus synthetic early/late promoter, inserted into the thymidine kinase locus. CMVA1 further comprises the VEE E2/E1 open reading frame operatively linked to a vaccinia virus synthetic early/late promoter inserted into MVA deletion III (see FIG. 3). CMVA2 comprises the VEE capsid open reading frame operatively linked to a vaccinia virus synthetic early/late promoter inserted into MVA deletion III. CMVA2 further comprises an alphavirus replicon, containing the nsPs and at least one foreign gene, operatively linked to a T7 promoter inserted into MVA deletion II (see FIG. 3). Cells infected with both CMVA1 and CMVA2 produce T7 polymerase, which transcribes the full-length replicon. The capsid and E2/E1 mRNAs are translated directly from mRNAs to produce the alphavirus structural proteins which encapsidate the replicon, thus producing alphavirus replicon particles. Of note, the helper functions are transcribed in the constitutive packaging systems, even if the alphavirus replicase is absent.

An illustrative inducible packaging systems also comprise two recombinant poxvirus vectors: inducible MVA vector 1 (IMVA1, also referred to as MVGKT7/DHcap) and inducible MVA vector 2 (IMVA2, also referred to as MVA/

Figure 4:
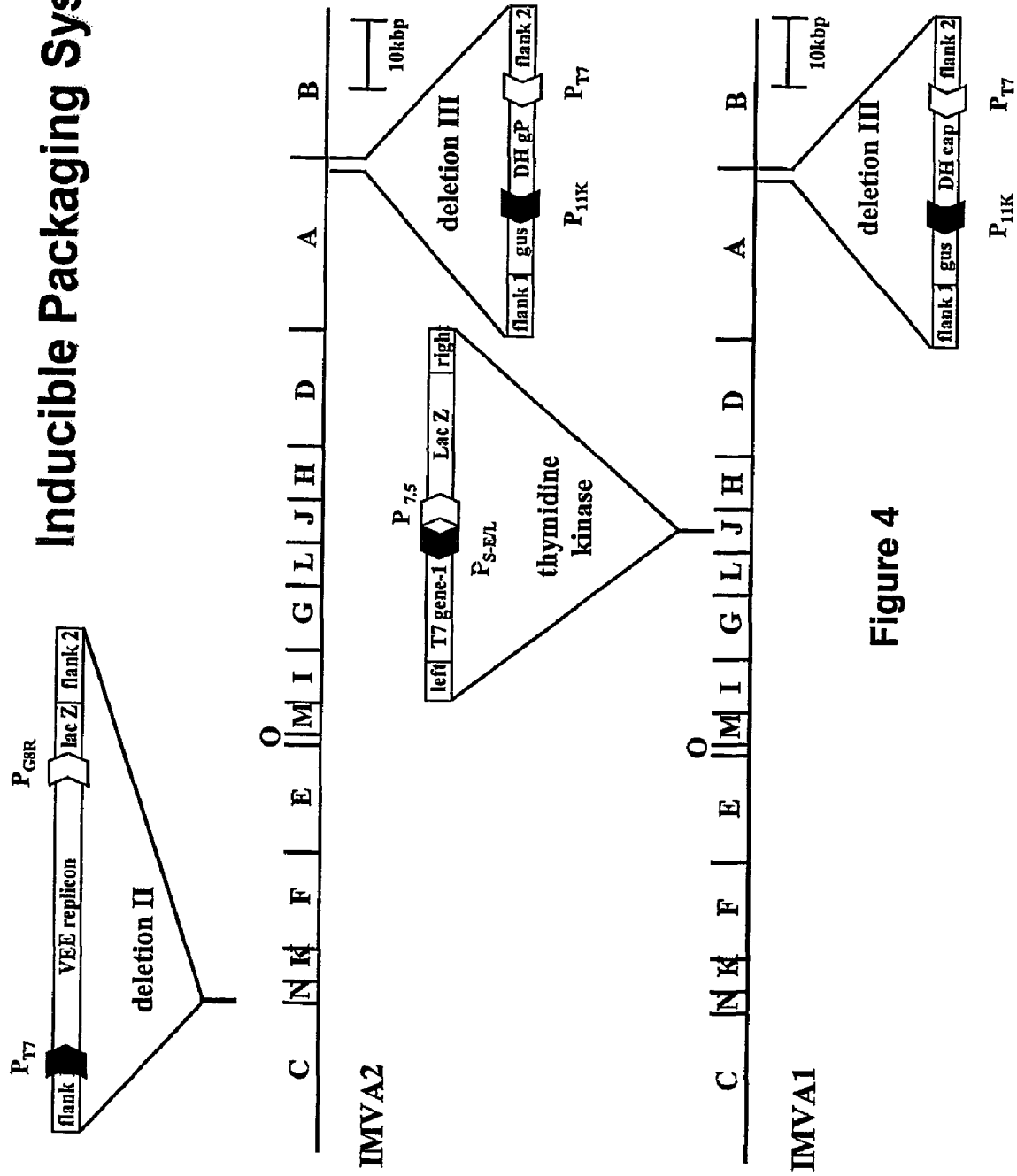
FIG. 4. Schematic representation of an exemplary alphavirus replicon particle inducible packaging system. Abbreviations are as identified in the brief description of FIG. 3, above.

VEEGFP/DHgP) (See FIG. 4). Like CMVA1, IMVA1 comprises the bacteriophage T7 gene-1, encoding a DNA-dependent RNA polymerase, operatively linked to a vaccinia virus synthetic early/late promoter, inserted into the thymidine kinase locus. In contrast to CMVA1, IMVA1 further comprises a replicon-like capsid helper RNA operatively linked to a T7 promoter inserted into MVA deletion III. IMVA2 comprises a replicon-like E2/E1 helper RNA operatively linked to a T7 promoter, inserted into MVA deletion III (See FIG. 4). IMVA2 further comprises a VEE replicon operatively linked to a T7 promoter inserted into deletion II of MVA (See FIG. 4). All of the replicon-like helper RNAs of the inducible packaging systems must be replicated by the alphavirus replicase before they are translated into helper proteins. Thus, cells infected with IMVA1 and IMVA2 will produce alphavirus replicon particles only if an alphavirus replicase is present.

Once psRNAV replicon particles have been produced, they may be amplified by coinfecting cells with the replicon particles and an MVA recombinant expressing psRNAV capsid and glycoproteins. In this system, the psRNAV replicon is able to replicate, but it lacks the structural genes required to form new replicon particles. Upon coinfection with an MVA recombinant expressing the structural proteins, replicon particles bearing the psRNAV replicon are assembled. In certain embodiments, the MVA recombinant expresses each structural protein under the control of a heterologous promoter. In certain embodiments, the promoter is a vaccinia virus synthetic early/late promoter, or another suitable poxvirus promoter(s), bacteriophage T7, T3, or SP6 promoters, or another promoter that is can direct transcription in the cytoplasm of the cell. In certain embodiments, vectors expressing bacteriophage T7, T3, or SP6 are provided in trans, and/or are stably expressed in the host cell. The skilled artisan will quickly recognize which promoters would be suitable in the amplification system described herein.

The skilled artisan will understand that, following the disclosed examples and applying only ordinary skill, alternate polymerases, poxvirus vectors, positive-strand RNA viruses, psRNAV structural or nonstructural protein sequences, replicons, and replicon-like helper RNAs, may be used interchangeably in the recombinant vectors and replicon packaging systems of the invention, without undue experimentation. Such recombinant vectors and packaging systems are within the scope of the invention.

The recombinant polynucleotides of the invention also include nucleic acid sequences that encode for polypeptide analogs or derivatives of the various polymerase and viral sequences, which differ from naturally-occurring forms, e.g., deletion analogs that contain less than all of the amino acids of the naturally-occurring forms, substitution analogs that have one or more amino acids replaced by other residues, and addition analogs that have one or more amino acids added to the naturally-occurring sequence. These various analogs share some or all of the biological properties of the polymerase or viral sequences or polypeptides from which they are derived. For example, but not limited to, catalyzing a DNA template-directed RNA polymerization reaction, transcriptionally regulating an operationally linked encoding sequence, forming a psRNAV replication complex, transcribing a psRNAV "antigenome", forming a psRNAV particle, and the like, as appropriate. One skilled in the art will be able to design suitable analogs and to test such analogs for biological activity using in vitro assay systems.

In certain preferred embodiments, conservative amino acid substitutions will be made. Conservative amino acid substitutions include, but are not limited to, a change in which a given amino acid may be replaced, for example, by a residue having similar physiochemical or biochemical characteristics. Examples of such conservative substitutions include, but are not limited to, substitution of one aliphatic residue for another, such as lie, Val, Leu, or Ala for one another, substitutions of one polar residue for another, such as between Lys and Arg, Glu and Asp, or Gin and Asn; or substitutions of one aromatic residue for another, such as Phe, Trp, or Tyr for one another. Other conservative substitutions, e.g., involving substitutions of entire regions having similar hydrophobicity characteristics, are well known. See Biochemistry: A Problems Approach, (Wood, W. B., Wilson, J. H., Benbow, R. M., and Hood, L. E., eds.) Benjamin/Cummings Publishing Co., Inc., Menlo Park, Calif. (1981), page 14–15.

In certain embodiments, the analogs will be 70%, 75%, 80%, 85%, 90%, 95%, or 99% identical or homologous to the naturally-occurring consensus sequences. As would be understood in the art, percent identity involves the relatedness between amino acid or nucleic acid sequences. One determines the percent of identical matches between two or more sequences with gap alignments that are addressed by a particular method. The percent identity may be determined by visual inspection and/or mathematical calculation. Alternatively, the percent identity of two nucleic acid sequences can be determined by comparing sequence information using the GAP computer program, version 6.0 described by Devereux et al. (*Nucl. Acids Res.* 12:387, 1984) and available from the University of Wisconsin Genetics Computer Group (UWGCG). The preferred default parameters for the GAP program include: (1) a unitary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps. Other programs used by one skilled in the art of sequence comparison may also be used.

Methods for obtaining infectious replicon particles are also provided. According to certain methods, mammalian or insect cells are coinfected with the recombinant viruses which form a novel packaging system of the invention. Any cell line that has been certified for use by the Food and Drug Administration for vaccine production may be used. Other cell lines shown to be restrictive for MVA growth may also be good candidates for replicon particle production, including, but not limited to, CHO, CHL, CV-1, 293, HeLa, SW 839, PK(15), MDCK, RK13, RAB-9, SIRC, Balb3t3, FS-2, MIB, SK 29 MEL 1, LC 5, 85 HG 66, U 138, C 8166, HUT 78, SY 9287, and Vero cells, described, among other places, in references (43), (44), and (46). Preferred mammalian cells include BHK-21 cells and FRhL cells. (ATCC Nos. CCL-10 and CL-160, respectively).

The coinfected cells are incubated under appropriate conditions for replicon particles to be generated. The skilled artisan will appreciate that appropriate conditions may vary, for example, from one cell line to another or one packaging system to another. The skilled artisan will know, or can readily determine, the appropriate conditions for generating replicon particles. Such appropriate conditions may include, for example, the optimal incubation temperatures and times, $CO_2$ concentrations, growth media, supplements, serum source and concentrations, inhibitors of DNA replication, such as AraC, and the like.

In certain embodiments of the invention, a vector containing the structural genes of a psRNAV and a replicon expression vector can be delivered to a cell using plasmids in lieu of viral vectors. The vectors are delivered to the cell using transfection technology that is well known in the art. Transfection methods are described in Sambrook et al., Molecular Cloning (1989) (38). Expression of the psRNAV genes may be driven by pol I promoters, pol II promoters, bacteriophage promoters, and/or other suitable promoters. In certain embodiments, the psRNAV structural genes and replicon are under the control of pol II promoters, which may or may not be inducible promoters. In certain embodiments, the psRNAV structural genes and replicon are under the control of bacteriophage promoters, such as a T7 promoter. In this system, the expression of the psRNAV genes is dependent on the expression of a T7 polymerase. T7 polymerase may be expressed by a cotransfected plasmid, or may be stably expressed by the host cell. With either system, the expression plasmids are cotransfected into a packaging cell line and the replicon particles are harvested from the cell medium.

Once generated, the replicon particles are obtained using procedures that are well-known in the art. Exemplary procedures include, but are not limited to, centrifugation, including sedimentation and isopycnic centrifugation, chromatography, and precipitation methods, such as selective precipitation using polyethylene glycol, NaCl, or the like.

Methods for titering replicon particles are also provided. In certain embodiments, an MVA recombinant is used to deliver a reporter gene to a suitable cell line. Coinfection of the cells with replicon particles activates the reporter gene, and the coinfected cells can be detected. In an exemplary embodiment, an MVA recombinant is made such that it contains a defective VEE RNA that encodes green fluorescent protein (GFP). Upon coinfection with replicon particles, the VEE replicase-transcriptase complex replicates and transcribes the "VEE-like" RNA, and GFP protein is expressed. The GFP can then be detected, and the titer of replicon particles determined. Suitable reporter genes include, but are not limited to, green fluorescent protein (GFP), blue fluorescent protein, yellow fluorescent protein, chloramphenicol acetyl-transferase (CAT), luciferase, beta-galactosidase, beta-glucoronidase. Detection methods include, but are not limited to, fluorescence microscopy, chemiluminescence, antibody staining, enzymatic analysis, and colorimetric staining.

The replicon particles formed by the methods of the invention can be employed as therapeutic or prophylactic immunogenic compositions, or as pharmaceutical formulations, depending at least in part on the foreign polypeptide(s) encoded in the replicon particles. The sequence encoding the at least one foreign polypeptide can vary as desired. Depending on the application of a particular replicon particle, the sequence encoding the at least one foreign polypeptide may encode a co-factor, cytokine (such as an interleukin), an epitope for a T cell, including helper, inducer, cytotoxic, and suppressor T cells, a restriction marker, an adjuvant, a polypeptide from a pathogenic microorganism, cancer or tumor cells, allergens, amyloid peptide, protein or other macromolecular components.

Exemplary pathogenic microorganisms include, but are not limited to, viruses, bacteria, fungi, or parasitic microorganisms which infect humans and non-human vertebrates.

Examples of such viruses include, but are not limited to, Human immunodeficiency virus, Simian immunodeficiency virus, Respiratory syncytial virus, Parainfluenza virus types 1–3, Herpes simplex virus, Human cytomegalovirus, Hepatitis A virus, Hepatitis B virus, Hepatitis C virus, Human papillomavirus, poliovirus, rotavirus, caliciviruses, Measles virus, Mumps virus, Rubella virus, adenovirus, rabies virus, canine distemper virus, rinderpest virus, coronavirus, parvovirus, infectious rhinotracheitis viruses, feline leukemia virus, feline infectious peritonitis virus, avian infectious bursal disease virus, Newcastle disease virus, Marek's disease virus, porcine respiratory and reproductive syndrome virus, equine arteritis virus and various Encephalitis viruses.

Examples of such bacteria include, but are not limited to, *Haemophilus influenzae* (both typable and nontypable), *Haemophilus somnus, Moraxella catarrhalis, Streptococcus pneumoniae, Streptococcus pyogenes, Streptococcus agalactiae, Streptococcus faecalis, Helicobacter pylori, Neisseria meningitidis, Neisseria gonorrhoeae, Chlamydia trachomatis, Chlamydia pneumoniae, Chlamydia psiftaci, Bordetella pertussis, Salmonella typhi, Salmonella typhimurium, Salmonella choleraesuis, Escherichia coli, Shigella, Vibrio cholerae, Corynebacterium diphtheriae, Mycobacterium tuberculosis, Mycobacterium avium-Mycobacterium intracellulare complex, Proteus mirabilis, Proteus vulgaris, Staphylococcus aureus, Clostridium tetani, Leptospira interrogans, Borrelia burgdorferi, Pasteurella haemolytica, Pasteurella multocida, Actinobacillus pleuropneumoniae* and *Mycoplasma gallisepticum.*

Examples of such fungi include, but are not limited to, *Aspergillis, Blastomyces, Candida, Coccidiodes, Cryptococcus* and *Histoplasma.* Examples of such parasites include, but are not limited to, *Leishmania major, Ascaris, Trichuris, Giardia, Schistosoma, Cryptosporidium, Trichomonas, Toxoplasma gondii* and *Pneumocystis carinii.*

Exemplary polypeptides from cancer or tumor cells include, but are not limited to, prostate specific antigen, carcino-embryonic antigen, MUC-1, Her2, CA-125 and MAGE-3. Exemplary allergens include, but are not limited to, those described in U.S. Pat. No. 5,830,877 and published International Patent Application No. WO 99/51259, which include pollen, insect venoms, animal dander, fungal spores and drugs (such as penicillin). Such components interfere with the production of IgE antibodies, a known cause of allergic reactions.

In one embodiment, the foreign polypeptide is amyloid peptide protein (APP) which has been implicated in diseases referred to variously as Alzheimer☐s disease, amyloidosis or amyloidogenic disease. The β-amyloid peptide (also referred to as A-beta peptide) is a 42 amino acid fragment of APP, which is generated by processing of APP by the β and γ secretase enzymes, and has the following sequence:

```
Asp Ala Glu Phe Arg His Asp Ser Gly Tyr Glu Val His His Gln Lys    (SEQ ID NO: 1)

Leu Val Phe Phe Ala Glu Asp Val Gly Ser Asn Lys Gly Ala Ile Ile Gly Leu

Met Val Gly Gly Val Val Ile Ala.
```

In some patients, the amyloid deposit takes the form of an aggregated A-beta peptide. Surprisingly, it has now been found that administration of isolated A-beta peptide induces an immune response against the A-beta peptide component of an amyloid deposit in a vertebrate host (See Published International Patent Application No. WO 99/27944). Such A-beta peptides have also been linked to unrelated moieties. Thus, the heterologous nucleotides sequences of this invention include the expression of this A-beta peptide, as well as fragments of A-beta peptide and antibodies to A-beta peptide or fragments thereof. One such fragment of A-beta peptide is the 28 amino acid peptide having the following sequence (as disclosed in U.S. Pat. No. 4,666,829):

```
Asp Ala Glu Phe Arg His Asp Ser Gly Tyr Glu Val His His Gln Lys   (SEQ ID NO: 2)
Leu Val Phe Phe Ala Glu Asp Val Gly Ser Asn Lys.
```

Foreign polypeptide of some embodiments may also include a sequence that is expressed as a single transcriptional unit. However, additional monocistronic transcriptional units or polycistronic transcriptional units may also be included. Use of the additional monocistronic transcriptional units, and polycistronic transcriptional units should permit the insertion of more genetic information. Where, for example, a polycistronic transcriptional unit is included, the sequence may further comprise one or more ribosomal entry sites. Alternatively, the foreign sequence may encode a polyprotein and a sufficient number of proteases that cleaves the polyprotein to generate the individual polypeptides of the polyprotein.

Those skilled in the art would readily recognize that the replicon particles of the invention may be used alone or in conjunction with pharmaceuticals, antigens, immunizing agents or adjuvants, as vaccines in the prevention or amelioration of disease. These active agents can be formulated and delivered by conventional means, i.e. by using a diluent or pharmaceutically acceptable carrier.

Accordingly, in further embodiments of this invention the replicon particles may be employed in immunogenic compositions comprising (i) at least one replicon particle and (ii) at least one of a pharmaceutically acceptable buffer or diluent, adjuvant or carrier. Preferably, these compositions have therapeutic and prophylactic applications as immunogenic compositions in preventing and/or ameliorating, for example, but without limitation, infectious diseases, cancer and other malignant conditions, allergic reactions, autoimmune conditions, and the like. In such applications, an immunologically effective amount of at least one replicon particle of the invention is employed to cause a substantial reduction in the course of the disease, reaction, condition, or malignancy.

Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The term "pharmaceutically acceptable carrier" refers to a carrier that does not cause an allergic reaction or other untoward effect in patients to whom it is administered. Suitable pharmaceutically acceptable carriers include, for example, one or more of water, saline, phosphate-buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the composition. The use of such media and agents for pharmaceutically active substances is well known in the art. Except insofar as any conventional media or agent is incompatible with the active ingredient, use thereof in immunogenic compositions of the present invention is contemplated.

Administration of such immunogenic pharmaceutical formulations may be by any conventional effective form, such as intranasally, parenterally (e.g. by subcutaneous, intramuscular, or intravenous injection), orally, or topically applied to mucosal surface such as intranasal, oral, eye, lung, vaginal, or rectal surface, such as by aerosol spray.

Oral formulations include such normally employed excipients as, for example, pharmaceutical grades of mannitol, lactose, starch, magnesium stearate, sodium saccharine, cellulose, magnesium carbonate, and the like.

The immunogenic compositions or pharmaceutical formulations of the invention can include an adjuvant, including, but not limited to, aluminum hydroxide; aluminum phosphate; Stimulon™ QS-21 (Aquila Biopharmaceuticals, Inc., Framingham, Mass.); MPL™ (3-O-deacylated monophosphoryl lipid A; Corixa, Hamilton, Mont.); synthetic adjuvant RC-529 (an aminoalkyl glucosamine phasphate derivative; Corixa Corp., Seattle, Wash.); IL-12 (Genetics Institute, Cambridge, Mass.); GM-CSF (Immunex Corp., Seattle, Wash.); N-acetyl-muramyl-L-threonyl-D-isoglutamine (thr-MDP); N-acetyl-nor-muramyl-L-alanyl-D-isoglutamine (CGP 11637, referred to as nor-MDP); N-acetyl-muramyl-L-alanyl-D-isoglutaminyl-L-alanine-2-(1'-2'-dipalmitoyl-sn-glycero-3-hydroxyphos-phoryloxy)-ethylamine (CGP 19835A, referred to a MTP-PE); and cholera toxin. Others which may be used are non-toxic derivatives of cholera toxin, holotoxins having reduced toxicity compared to wild-type cholera toxins, including it's A subunit (for example, wherein glutamic acid at amino acid position 29 is replaced by another amino acid, preferably, a histidine in accordance with Published International Patent Application No. WO 00/18434), and/or conjugates or genetically engineered fusions of the at least one foreign polypeptide with cholera toxin or its B subunit, procholeragenoid, fungal polysaccharides.

One important aspect of the invention relates to a method for inducing an immune response in a mammal or human host comprising administering an immunogenic composition of the invention to the host. Provided that an immunologically effective amount of the immunogenic composition is administered, the host will develop a desired immune response. The dosage amount can vary depending upon specific circumstances, such as size (weight) and the developmental state of the host individual. This amount can be determined in routine trials by means, known to those skilled in the art.

Certainly, the isolated foreign polypeptides produced using the packaging systems and/or methods of the invention may be used in forming subunit vaccines. They may also be used as antigens for raising polyclonal or monoclonal antibodies and in immunoassays for the detection of antibodies that are reactive with the foreign polypeptide(s) of the invention. Immunoassays encompassed by the present invention include, but are not limited to those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

The invention also provides kits designed to expedite performing the subject methods. Kits serve to expedite the performance of the methods of interest by assembling two or more components required for carrying out the methods. Kits preferably contain components in pre-measured unit amounts to minimize the need for measurements by end-users. Kits preferably include instructions for performing one or more methods of the invention. Preferably, the kit components are optimized to operate in conjunction with one another.

Kits may also be used to generate the packaging systems disclosed herein or to insert desired foreign genes into the psRNAV replicon. Kits of the invention include kits that facilitate titering replicon particles. The immunogenic compositions and pharmaceutical formulations of the invention may be prepared using the disclosed kits.

The invention, having been described above, may be better understood by reference to examples. The following examples are intended for illustration purposes only, and should not be construed as limiting the scope of the invention in any way. While MVA and VEE are used as exemplary poxvirus and positive-strand RNA virus systems, respectively, the skilled artisan will appreciate that other poxviruses and positive-strand RNA viruses may be used interchangeably without undue experimentation. Thus, the use of other poxviruses and/or alphaviruses are contemplated and are within the intended scope of the invention. Although the wild-type strains of vaccinia virus could also be used to package VRPs, their cytopathic effect and unrestricted growth in a broad range of cells would limit their utility. Other host-range defective mutants of vaccinia virus including the NYVAC strain or naturally occurring poxviruses with limited host-range (e.g., avipoxvirus, parapoxvirus, capripoxvirus, leporipoxvirus, suipoxvirus, or entomopoxviruses) could also be used as packaging vectors. Other positive-strand RNA viruses that may be used included, but are not limited to, Rubella, Hepatitis C virus, Dengue virus, Coronavirus, and the like.

EXAMPLES

Example 1

Materials and Methods

1A Development of a Recombinant MVA Vector Capable of Expressing Abundant T7 RNA Polymerase Early in Infection.

A stock of MVA (24), (23), (25), obtained from Dr. Bernard Moss (NIAID), was plaque purified and amplified on certified chick embryo fibroblasts (CEF; SPAFAS) in minimal essential media (Life Technologies) supplemented with 10% fetal bovine serum (Life Technologies). This virus was utilized as the parent for insertion of all foreign genes and expression cassettes.

Figure 2:
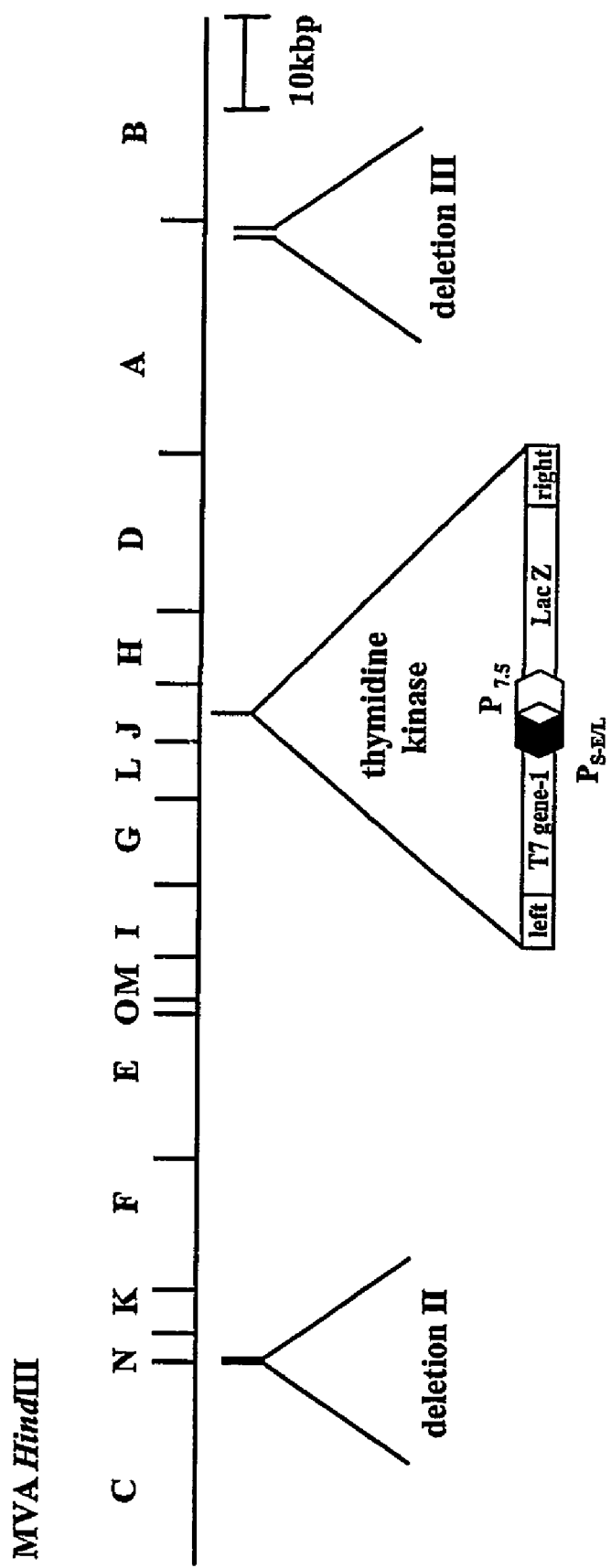
FIG. 2. Schematic representation of the MVGKT7 expression vector. Shown is the HindIII restriction map of the virus. The bacteriophage T7 gene-1 is located in the HindIII J fragment. Also shown are MVA deletions II and III that are useful for the insertion of recombinant polynucleotides and foreign genes. Other deletions (such as I, IV, V, and VI) have been mapped relative to these HindIII restriction sites and may also be useful sites for foreign gene insertion.
Figure 5:
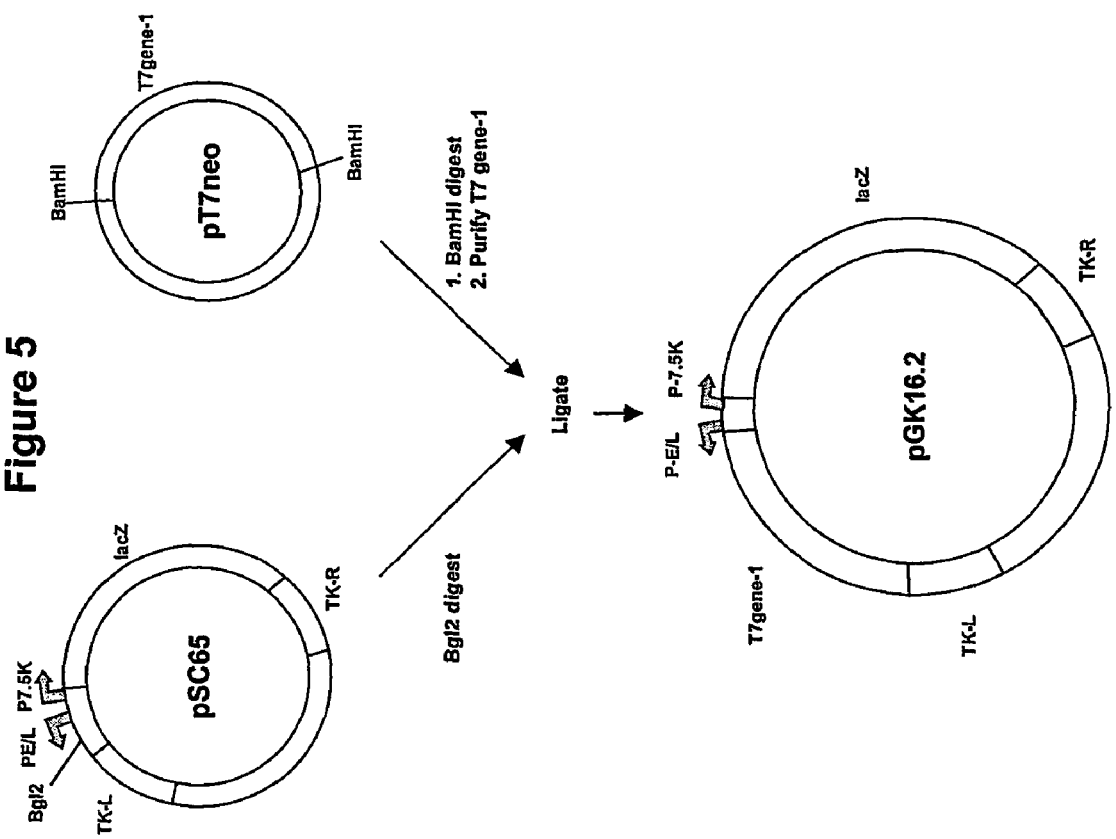
FIG. 5. Schematic map illustrating the generation of plasmid pGK16.2. Stippled arrowheads represent the vaccinia synthetic early/late promoter (PE/L) and the vaccinia 7.5K promoter (P7.5K). TK-L and TK-R indicate regions of homology with the vaccinia virus thymidine kinase (TK) locus.

A recombinant MVA expression vector (MVGKT7) was engineered to express abundant amounts of the bacteriophage T7 RNA polymerase early in infection (FIG. 2). It was necessary to express abundant levels of T7 polymerase early in infection because, as demonstrated below, VEE coinfection limits expression from vaccinia late promoters. The T7 RNA polymerase gene was excised from pT7-Neo (gift of Dr. S. Lee, Wyeth Lederle Vaccines) as a BamHI fragment and subcloned into the Bg/II site of pSC65 ((9); obtained from Dr. Bernard Moss), to generate pGK16.2 (see FIG. 5). The skilled artisan will understand T7 can come from other sources. This plasmid contains flanking sequences for homologous recombination into the thymidine kinase locus of MVA, a lac-Z marker gene, and a synthetic early/late vaccinia virus promoter (9) regulating the transcription of the T7 RNA polymerase gene. The recombinant virus, MVGKT7, was produced using methods described previously (36). Briefly, CEF were infected with MVA at a multiplicity of infection (MOI) equal to 0.5 plaque forming units (PFU) per cell, and subsequently transfected with pGK16.2 using DOTAP transfection reagent (Boehringer Mannheim). Recombinant viruses were plaque-purified three times consecutively on CEF using a 5-Bromo-4-chloro-3-indolyl-β-D-galactopyranoside (X-gal) colorimetric plaque assay (8), (22). The purity and stability of the recombinant virus was assessed by immunostaining with a rabbit polyclonal anti-T7 polymerase antibody (gift of Dr. S. Lee, Wyeth Lederle Vaccines) and a polyclonal antiserum raised against vaccinia virus (BioGenesis). The skilled artisan will appreciate that polyclonal anti-T7 polymerase antiserum is easily generated using commercially available T7 polymerase in conventional serum preparation methods. Detailed descriptions of such methods may be found, among other places, in Harlow and Lane, eds. Antibodies, A Laboratory Manual, Cold Spring Harbor Press, 1988.

1B. Development of an Inducible MVA-based VRP Packaging System.

Figure 6:
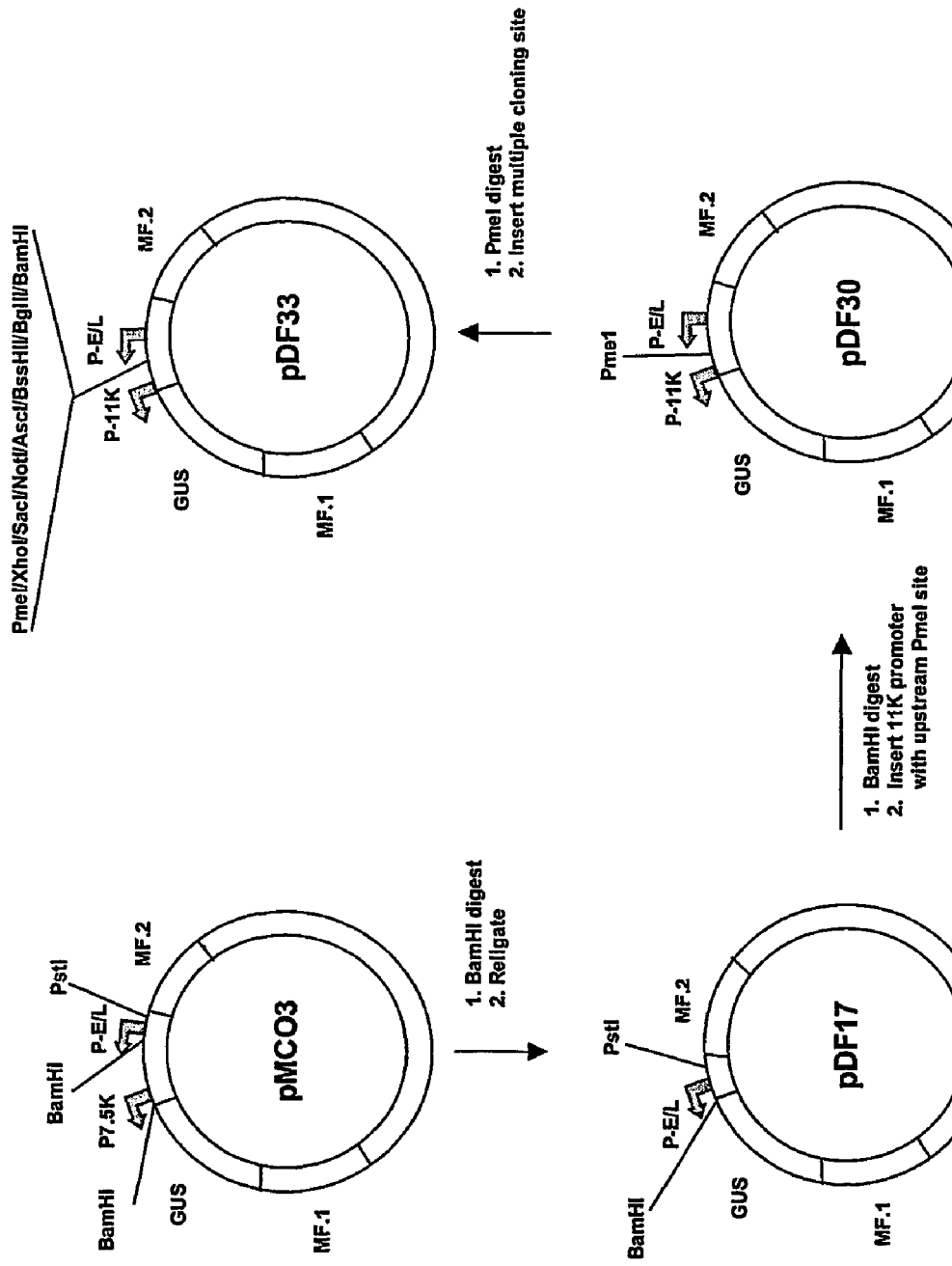
FIG. 6. Schematic map illustrating the generation of plasmids pDF17, pDF30, and pDF33. Stippled arrowheads represent the vaccinia synthetic early/late promoter (PE/L), the vaccinia 7.5K promoter (P7.5K), and the vaccinia 11K promoter (P11K). MF-1 and MF-2, in this figure, indicate regions of homology with the region designated "deletion III" of MVA.
Figure 7:
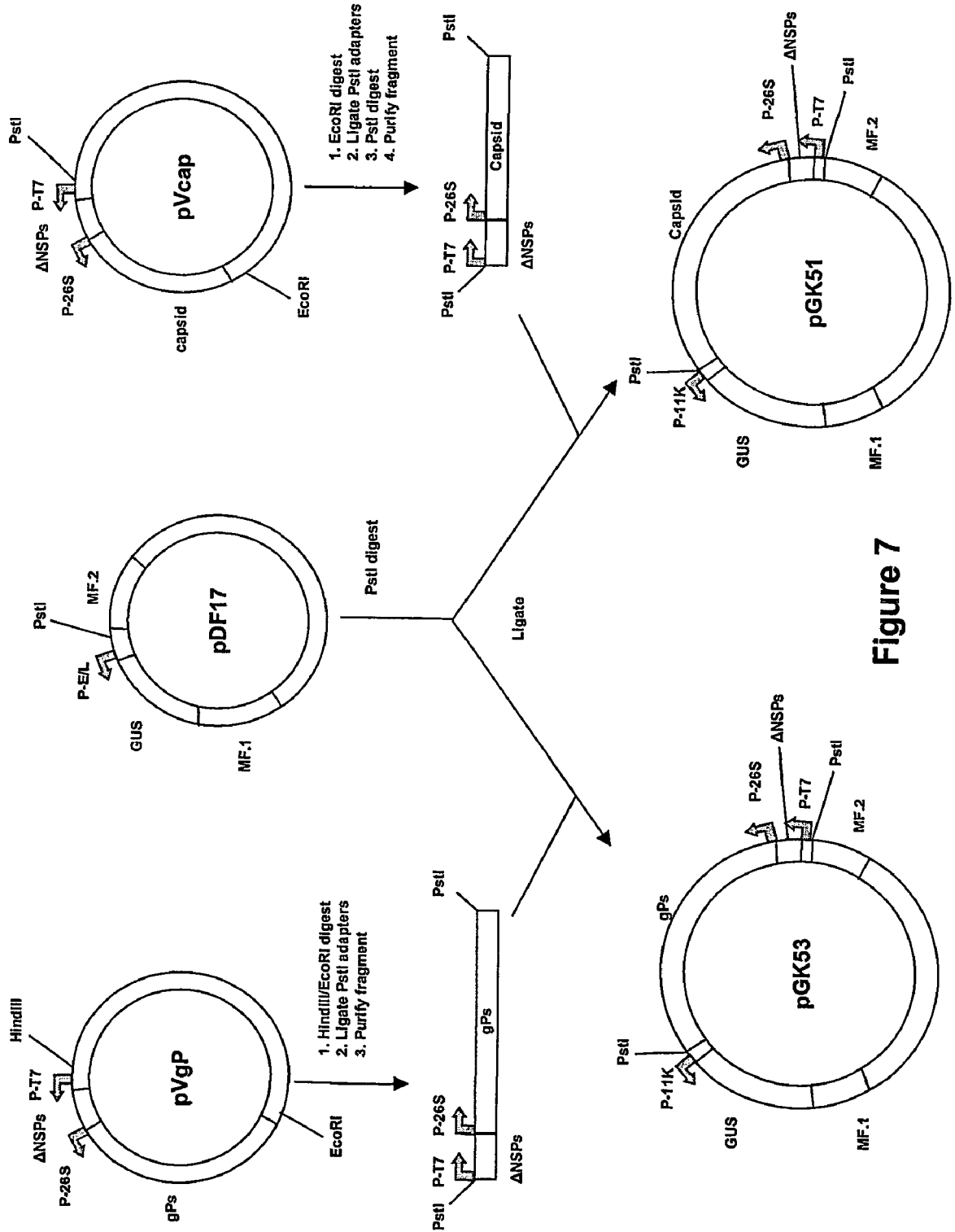
FIG. 7. Schematic map illustrating the generation of plasmids pGK53 and pGK51. Stippled arrowheads represent the vaccinia synthetic early/late promoter (PE/L), the vaccinia 7.5K promoter (P7.5K), the vaccinia 11K promoter (P11K), the bacteriophage T7 promoter (P-T7), and the alphavirus subgenomic promoter (P-26S). ΔnsP is a large deletion within the nsP expression cassette.
Figure 8:
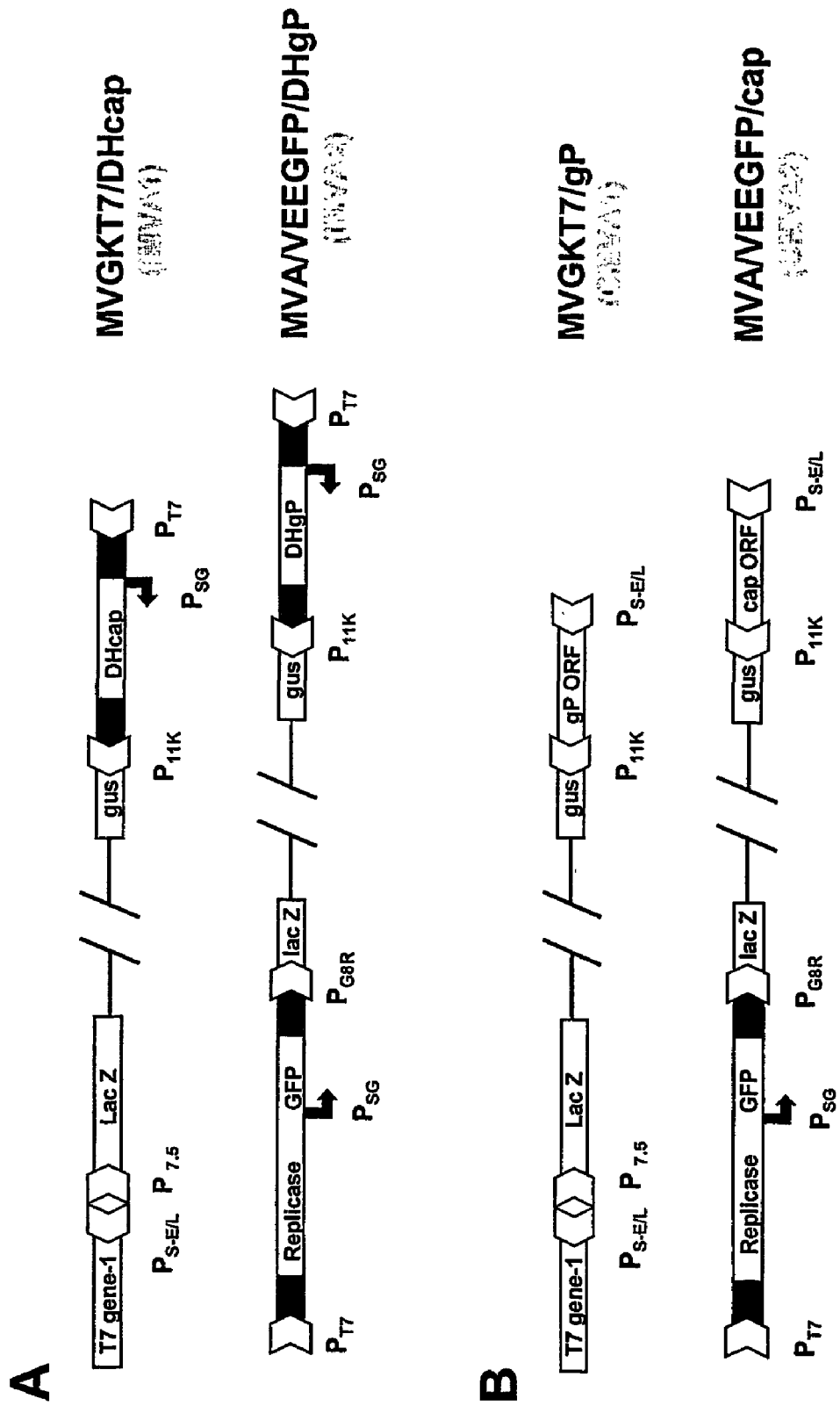
FIG. 8. Schematic representation of the genomes of recombinant MVAs used in exemplary poxvirus-based alphavirus replicon particle packaging systems. (A) Inducible system. (B) Constitutive system. Designations of recombinant MVAs are shown at right. Specific promoters used are indicated as stippled arrowheads. VEE replication sequences are indicated as black boxes. The alphavirus subgenomic promoters are indicated as curved black arrows. The VEE nonstructural protein genes are denoted as replicase. GFP, green fluorescent protein; gus, β-glucuronidase gene; T7 gene-1, T7 RNA polymerase gene; lacZ, β-galactosidase gene; gP, E3/E2/6K/E1 glycoprotein; cap, capsid; DH, defective-helper; ORF, open reading frame. Not drawn to scale.

An expression vector plasmid, pMCO3, used for insertion of foreign DNA into deletion III of MVA (obtained from B. Moss, (7)) was modified by digesting with BamHI and religating (see FIG. 6). This removed the 7.5K promoter used to transcribe the marker gene β-glucuronidase (GUS) and moved the synthetic early/late promoter, used to transcribe foreign genes, upstream of GUS. The modified plasmid, pDF17, contains a unique PstI site upstream of the synthetic early/late promoter-GUS gene. The defective-helper gene cassettes were derived from plasmids pV3014Δ520-7505Δ8495-11229 and pV3014Δ520-7505Δ7565-8386 herein referred to as pVcap and pVgP, respectively (obtained from AlphaVax, (27)). Both helpers were originally isolated from V3014, a laboratory-derived, highly attenuated VEE mutant that contains a mutation in E1 (A272T) and two in E2 (E209K, I239N), yet is immunogenic and has been used as an expression vector (10), (12). Plasmids pVcap and pVgP were digested with EcoRI/PstI or HindIII/EcoRI, respectively, to excise the T7 promoter-helper gene cassettes (see FIG. 7). The ends of both cassettes were modified to contain PstI-compatible cohesive ends, and were then cloned individually into the PstI site of pDF17. The resultant plasmids contain either the capsid defective helper (pGK51) or the glycoprotein defective-helper (pGK53) expression cassettes under the regulation of T7 promoters (see FIG. 7). Recombinant MVA vectors were produced by transfection of pGK51 into MVGKT7-infected cells to yield MVGKT7/DHCap (FIG. 8A), and transfection of pGK53 into MVA-infected cells to yield MVA/DHgP. Both recombinant viruses were selected using a colorimetric plaque assay based on GUS gene expression (7). These viruses express defective-helper VEE RNAs that are not translated into capsid or glycoproteins, unless they are replicated by the VEE replicase. Thus, expression of the helpers is referred to as "inducible".

Figure 9:
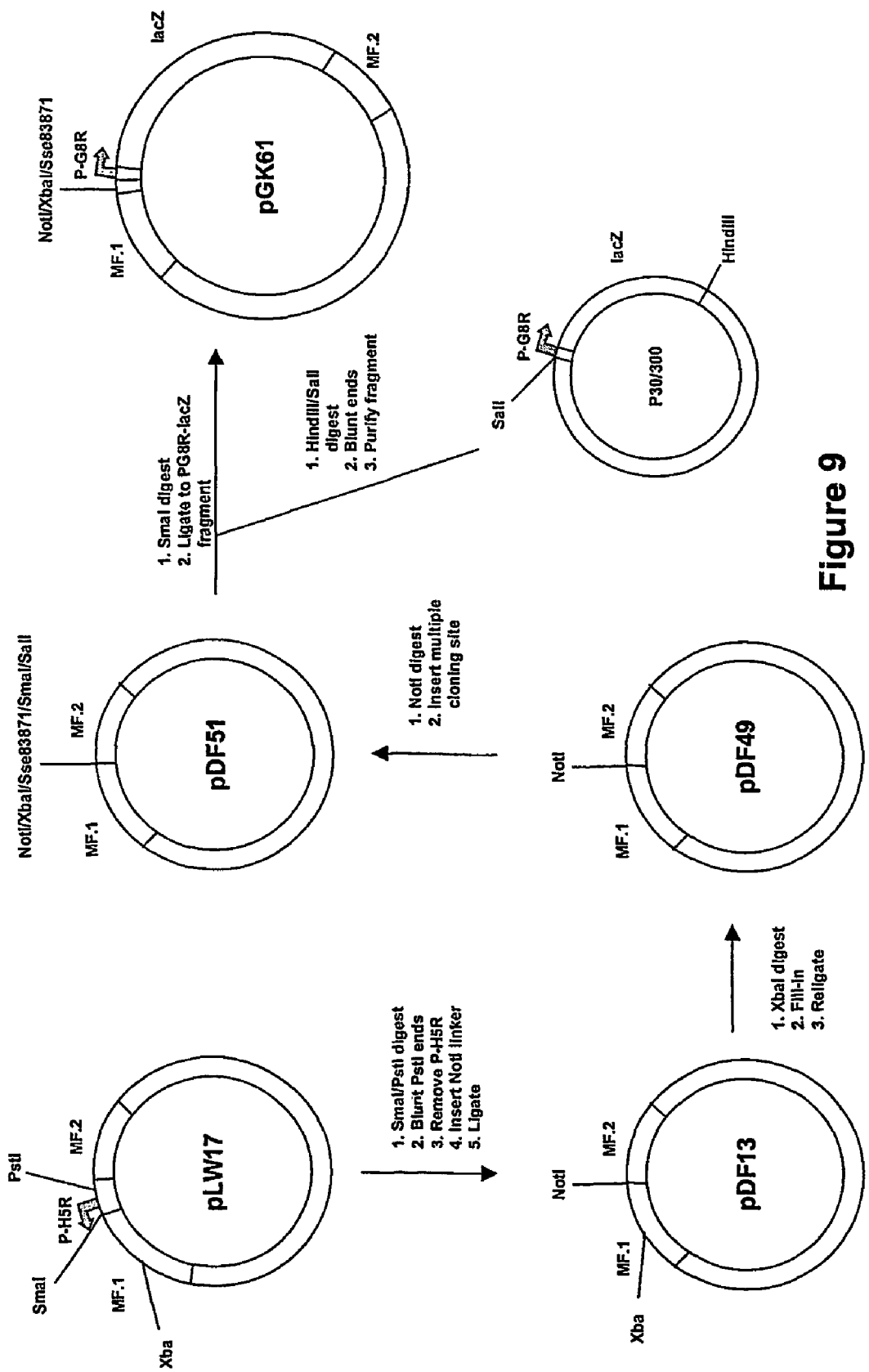
FIG. 9. Schematic map illustrating the generation of plasmids pDF13, pDF49, pDF51, and pGK61. Stippled arrowheads represent the H5R promoter (P-H5R) and the G8R promoter (P-G8R). In this figure, MF-1 and MF-2 indicate regions of homology with the region designated "deletion II" of MVA.
Figure 10:
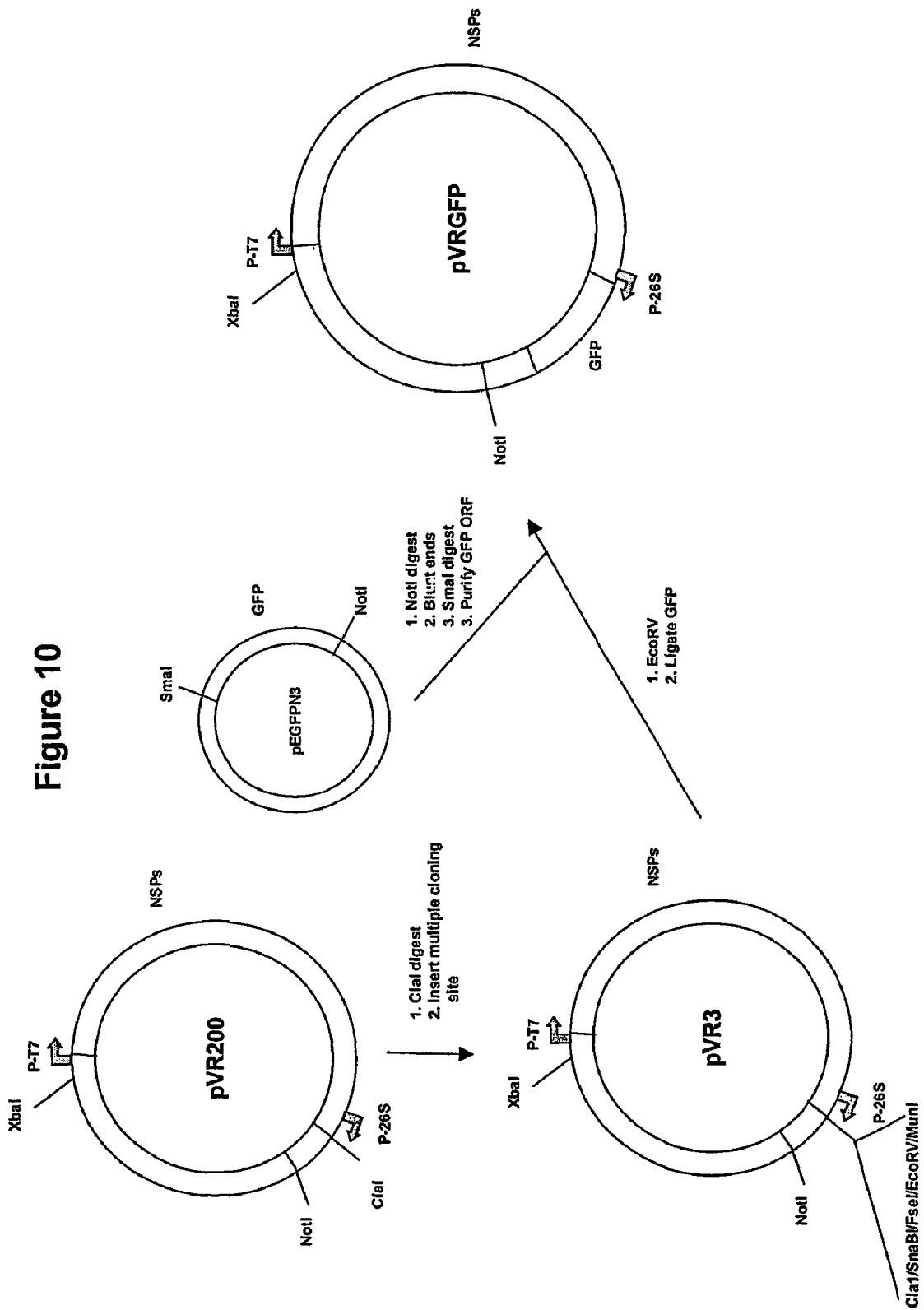
FIG. 10. Schematic map illustrating the generation of plasmids pVR3 and pVRGFP. Stippled arrowheads represent the bacteriophage T7 promoter (P-T7) and the alphavirus subgenomic promoter (P-26S).
Figure 11:
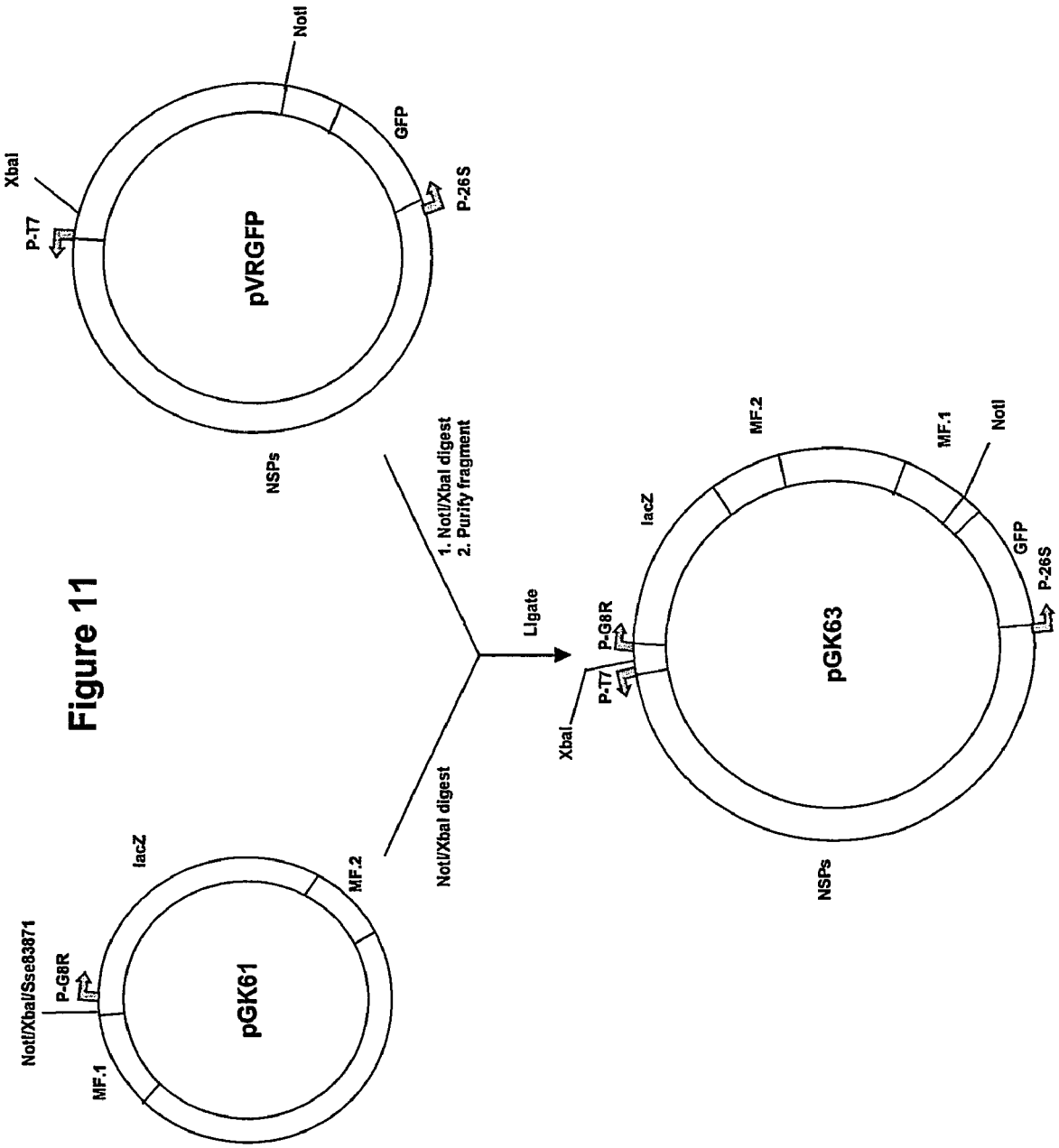
FIG. 11. Schematic map illustrating the generation of plasmid pGK63. Stippled arrowheads represent the bacteriophage T7 promoter (P-T7), the G8R promoter (P-G8R), and the alphavirus subgenomic promoter (P-26S).
Figure 12:
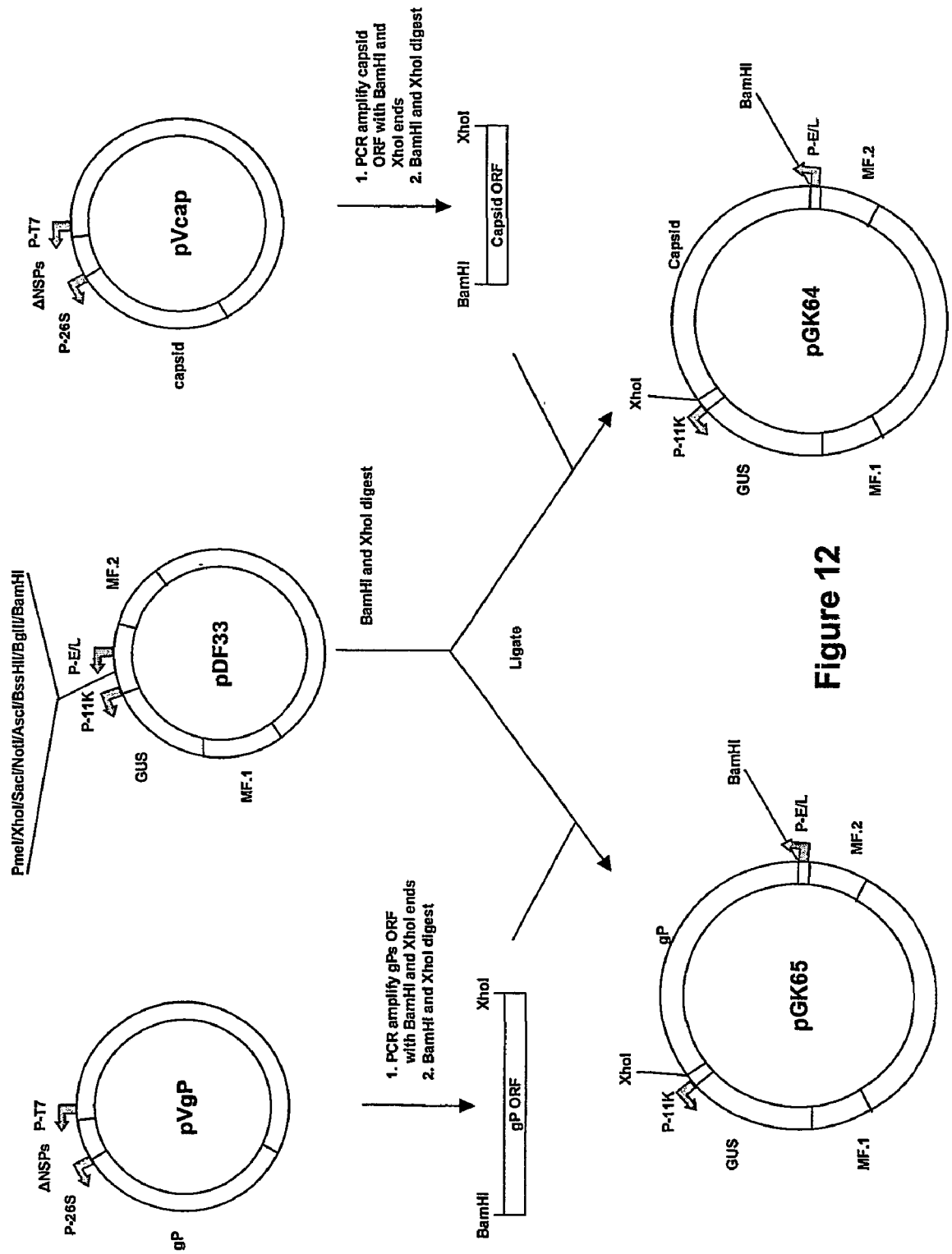
FIG. 12. Schematic map illustrating the generation of plasmids pGK64 and pGK65. Stippled arrowheads represent bacteriophage T7 promoter (P-T7), the vaccinia synthetic early/late (P-E/L) and 11K (P11K) promoters, and the alphavirus subgenomic promoter (P-26S).

The second step in the development of the inducible MVA-based VRP packaging system was to engineer a recombinant MVA vector capable of expressing a full-length VEE replicon under the control of a T7 promoter. As shown in FIG. 9, several modifications were made to pLW17 (an expression vector that enables insertion of foreign genes into deletion II of MVA; obtained from Dr. B. Moss; see FIG. 18; SEQ ID NO: 3) to allow for cloning of replicon cDNAs. First, pLW17 was digested with SmaI and PstI to remove the vaccinia virus H5R promoter used for foreign gene expression, and a unique NotI restriction site was inserted in its place to yield pDF13 (See FIG. 9). To aid cloning into the final transfer vector, a unique XbaI site present in one of the homologous flanking regions in pDF13 was ablated by digestion, filled-in with T4 DNA polymerase and religated. The resultant plasmid, pDF49, was digested with NotI, and a polylinker containing unique NotI, XbaI, Sse83871, SmaI, and SalI restriction sites was inserted to yield pDF51 (See FIG. 9). A vaccinia virus intermediate promoter (G8R)-lacZ expression cassette was derived from p30/300 (obtained from Dr. B. Moss; (1)) and inserted into the SmaI site present in the polylinker of pDF51 to allow colorimetric selection of recombinant viruses. The resultant plasmid (pGK61) contains two regions of homology with MVA for insertion into deletion II, a lacZ colorimetric marker gene, and three unique restriction sites (Sse83871, XbaI and NotI) for directional cloning of VEE replicon cDNAs (See FIG. 9).

A VEE replicon vector capable of expressing the green fluorescent protein (GFP) gene was constructed by removing the GFP gene from pEGFP-N3 (Clontech; Palo Alto, Calif.) as a SmaI-NotI fragment, filling-in staggered ends with T4 DNA polymerase, and inserting into the EcoRV site of pVR3 (a derivative of pVR200 obtained from AlphaVax), (See FIG. 10). The resultant expression plasmid, pVRGFP (provided by Dr. Larry Smith; WyethLederle Vaccines), was digested with XbaI and NotI to excise the entire replicon genome-GFP preceded by a T7 promoter (see FIG. 10). The T7 promoter-linked replicon-GFP fragment was subsequently inserted into pGK61 to yield pGK63 (See FIG. 11). This plasmid was then transfected into MVA/DHgP-infected cells to yield MVA/VEEGFP/DHgP (see FIG. 8A), a recombinant MVA virus that contains both a VEE replicon-GFP cDNA and the glycoprotein helper gene under the transcriptional regulation of T7 promoters 1 C. Development of a Constitutive MVA-based VRP Packaging System.

The polymerase chain reaction (PCR) was used to amplify the open reading frames (ORFs) of the capsid and E3/E2/6K/E1 polyprotein cassette from pVRCap and pVRgP, respectively. These fragments were then cloned into pDF33 (a deletion III MVA expression vector that was derived from pMCO3, (7)) (see FIGS. 6 and 12). The resultant plasmids pGK64 and pGK65 contain the capsid or E3/E2/6K/E1 polyprotein ORFs, respectively, under the regulation of vaccinia virus synthetic early/late promoters. A recombinant MVA virus capable of expressing the T7 RNA polymerase and the VEE glycoproteins was produced by transfection of pGK65 into MVGKT7-infected CEF using the methods described above. The resultant virus (MVGKT7/gP) constitutively expresses T7 RNA polymerase and the VEE spike glycoproteins (FIG. 8B).

A separate recombinant MVA virus capable of transcribing the capsid gene and a VEE replicon RNA was engineered in two steps. First, a recombinant MVA virus was isolated from MVA-infected cells that had been transfected with pGK64. This virus (MVA/cap) contains an expression cassette comprising the VEE capsid gene under the control of the synthetic early/late promoter inserted into deletion III of MVA. Second, pGK63 (from Example 1B, above) was transfected into MVA/cap-infected cells to yield MVA/VEEGFP/cap (FIG. 8B). This virus expresses the VEE capsid gene and also contains a T7 promoter-regulated replicon-GFP expression cassette 1D. Characterization of VRP-packaging MVAs.

Recombinant plasmids were sequenced using dye terminator cycle sequencing and the 377 ABI DNA sequencer (Applied Biosystems). Recombinant MVA viruses were checked for purity by PCR analysis. Expression of the E1 and E2 glycoproteins and capsid was assayed by Western blot analyses. Approximately $2\times10^6$ baby hamster kidney (BHK-21) cells were infected with recombinant MVA viruses at a multiplicity of infection equivalent to 10 PFU per cell, and incubated at 37° C. for 24 hr. Subsequently, cells were boiled in SDS disruption buffer (0.05 M Tris, 4% SDS, 4% beta-mercaptoethanol, 10% glycerol, 0.1% bromophenol blue) and an aliquot was analyzed by immunoblotting using mouse hyperimmune anti-VEE sera (ATCC, Manassas, Va.) at a 1:1,000 dilution. Immunoblots were developed using a rabbit anti-mouse IgG conjugated to alkaline phosphatase secondary antibody (Life Technologies) and the Western Blue substrate (Promega, Madison, Wis.). Expression of the VEE structural proteins was also analyzed in BHK-21 cells that were co-electroporated with in vitro transcribed VEE replicon-GFP RNA, gP helper and capsid helper RNAs as previously described (19), (27). (See FIG. 16).

1 E. Production of VEE Replicon Particles (VRP)

A VEE replicon particle, referred to as VRP/GFP, that expresses the GFP gene under the regulation of the subgenomic promoter was obtained by co-infecting BHK-21 cells with MVGKT7/DHCap and MVA/VEEGFP/DHgP (an exemplary inducible system; see FIG. 4) or MVGKT7/gP and MVA/VEEGFP/cap (an exemplary constitutive system; see FIG. 3). Typically, recombinant viruses were adsorbed in a minimal volume of inocula for 1 h with rocking at room temperature. Infected cells were washed twice with PBS, and incubated in modified Eagle's medium (MEM) containing 10% fetal bovine serum (FBS). Replicon particles were harvested from infected-cell media after 24 hpi using centrifugation at 3,000×g for 10 min. Serial dilutions of VRP/GFP preparations were assayed on fresh BHK-21 cells and the titer, expressed as IU/ml, was determined by counting the total number of fluorescent cells per well at an appropriate dilution.

The titer of the recombinant MVA helper viruses in the VRP preparations was determined by infecting CEF with serially-diluted infected-cell media, fixing cells with 2% formaldehyde at 48 hpi., and subsequently immunostaining monolayers with anti-vaccinia virus antisera (BioGenesis) followed by a horseradish peroxidase-conjugated anti-rabbit IgG secondary antibody (Life Technologies), and staining with the AEC Peroxidase Substrate Kit (Enzo). The titers of recombinant MVA helper viruses were expressed as PFU/ml. Possible contaminating replication-competent VEE, resulting from recombination between helper RNAs and the replicon, was assayed by a standard plaque assay on Vero cells after three serial undiluted passages in naive Vero cells. This assay differentiates between replicon particles and replication-competent virus on the basis of viral growth after the second passage.

Example 2

Characterization of MVA and VEE Coinfection

Figure 13:
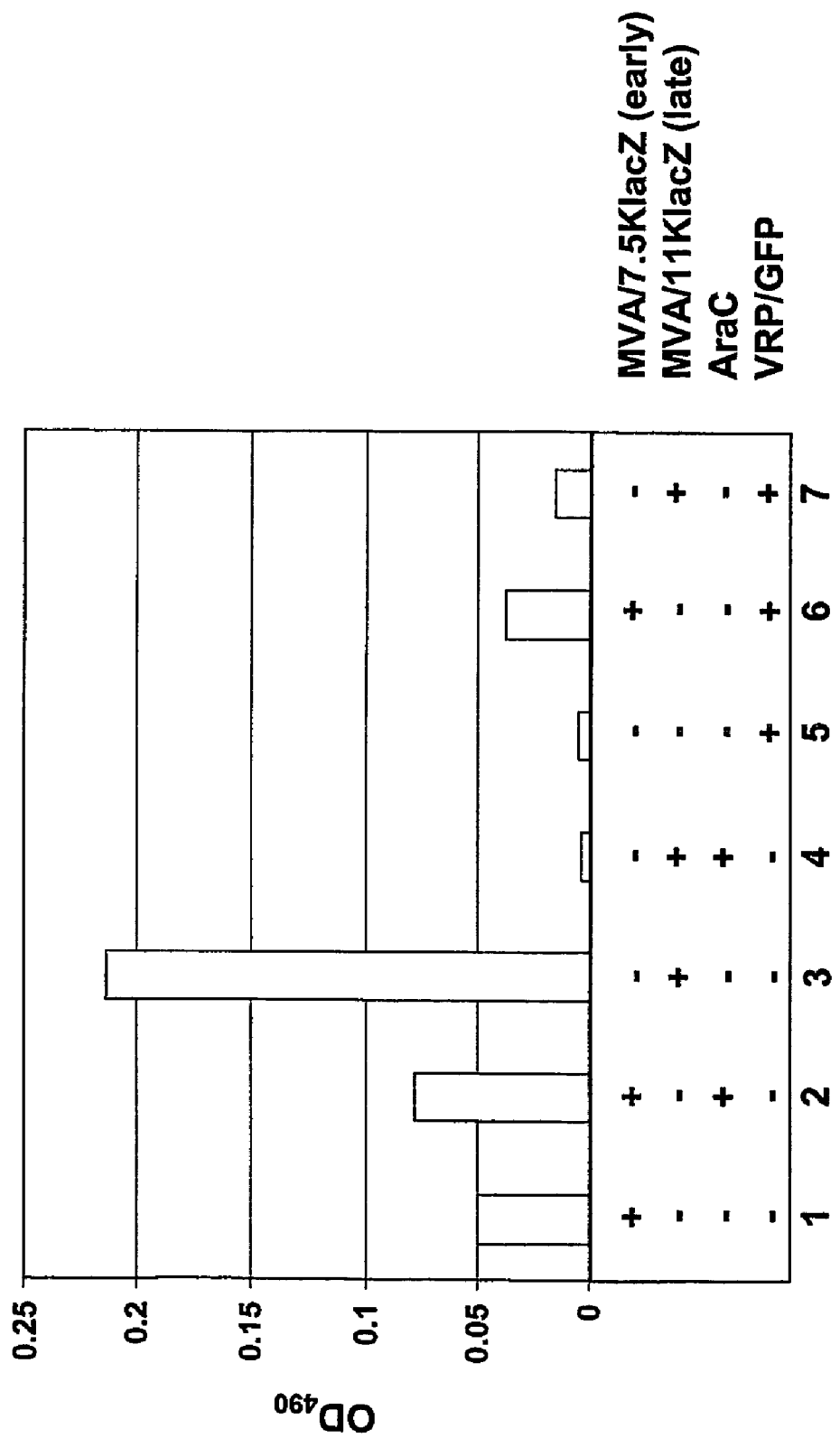
FIG. 13. VEE inhibits MVA late gene expression. BHK-21 cells were infected at a multiplicity of infection (MOI) equivalent to 10 plaque forming units (PFU) of recombinant MVAs alone, or 10 infectious units (IU) of VRP/GFP, or both, and harvested at 24 hours post infection (hpi). Cytosine beta-D arabinosidase, or AraC (44 μg/ml), was added to cells where indicated. Lysates were prepared and assayed for β-galactosidase activity ($OD_{490}$).

To evaluate whether VEE coinfection of MVA infected cells would affect poxvirus early and/or late gene expression, two recombinant MVA viruses that express lacZ under the control of either a viral early promoter (MVA/7.5KlacZ) or a late promoter (MVA/11KlacZ) were used to infect cells with or without VEE coinfection. BHK-21 cells were infected with 10 PFU of MVA/7.5KlacZ or MVA11KlacZ per cell alone or with 10 IU per cell of VRP/GFP. Cells were harvested at 24 hpi, and assayed for β-galactosidase activity, a measure of poxvirus gene expression (see FIG. 13). The levels of β-galactosidase detected in samples 1 and 3 of FIG. 13 are indicative of normal early and late gene expression during MVA infection, respectively. Addition of cytosine-beta-D-arabinofuranoside (AraC), a drug that blocks MVA DNA replication, shows that late but not early genes are inhibited (FIG. 13, compare sample 2 to 4). Coinfection of cells with MVA/11KlacZ and VRP/GFP shows that VEE replication has an effect on late gene expression that is similar to AraC. β-galactosidase expression was reduced in coinfected cells by nearly 95% (FIG. 13, compare samples 3,4, and 7). This indicates that MVA DNA replication and/or late gene transcription is inhibited by VEE replication. MVA early gene expression was also reduced by coinfecting with VRP/GFP, albeit to a lesser extent than late gene expression (FIG. 13, compare samples 1 to 6).

A similar experiment was conducted to determine the effects of MVA infection on VEE replication. (See Table 1). BHK-21 cells were infected with VRP/GFP alone or together with MVA. At 24 hpi, cells were analyzed for expression of GFP by flow cytometry using a FACScan (Beckton Dickinson) and Cell Quest 3.1 software. The intensity of GFP fluorescence is directly proportional to the level of VEE subgenomic promoter transcription. Surprisingly, cells that were co-infected with VRP/GFP and MVA expressed at least 50–60% more GFP than cells infected with VRP/GFP alone. This suggests that one or more MVA gene products appear to facilitate or stimulate the replication and/or transcription of VEE. (See Table 1), The results shown in FIG. 13 and Table 1 suggested that: 1) vaccinia virus strong early promoters (e.g. a synthetic early/late (9), H5R (48), Pse1 (47)) could be used to express the VEE replicon, and structural genes, 2) the growth of the VRP-packaging MVAs would be severely impaired during VEE replicon packaging, thereby further reducing the risk of adventitious contamination of VRP with MVA, and 3) in the presence of an ongoing MVA infection, VEE replication and subsequent particle formation may be enhanced.

Example 3

Characterization of an Inducible MVA-based VRP Packaging System

The titers obtained by coinfection with MVA/VEEGFP/DHgP (IMVA1) and MVGKT7/DHCap (IMVA2) (see FIG. 4) were compared to those produced with the standard split-helper RNA transfection method. BHK-21 cells were chosen as the cell substrate for packaging because they have been shown to produce the highest titers of VRP. However, BHK-21 cells are not appropriate for mass production of VRP using the MVA-based VRP-packaging systems because they are fully permissive for MVA growth (6), (13), (4). BHK-21 cells were infected with two recombinant MVA vectors constituting the inducible packaging system at an MOI of 1, 10 or 20 total PFU/cell. Alternatively, the cells were co-electroporated with VEE replicon-GFP RNA, capsid DH RNA, and gP DH RNA synthesized in vitro by T7 RNA polymerase.

Figure 14:
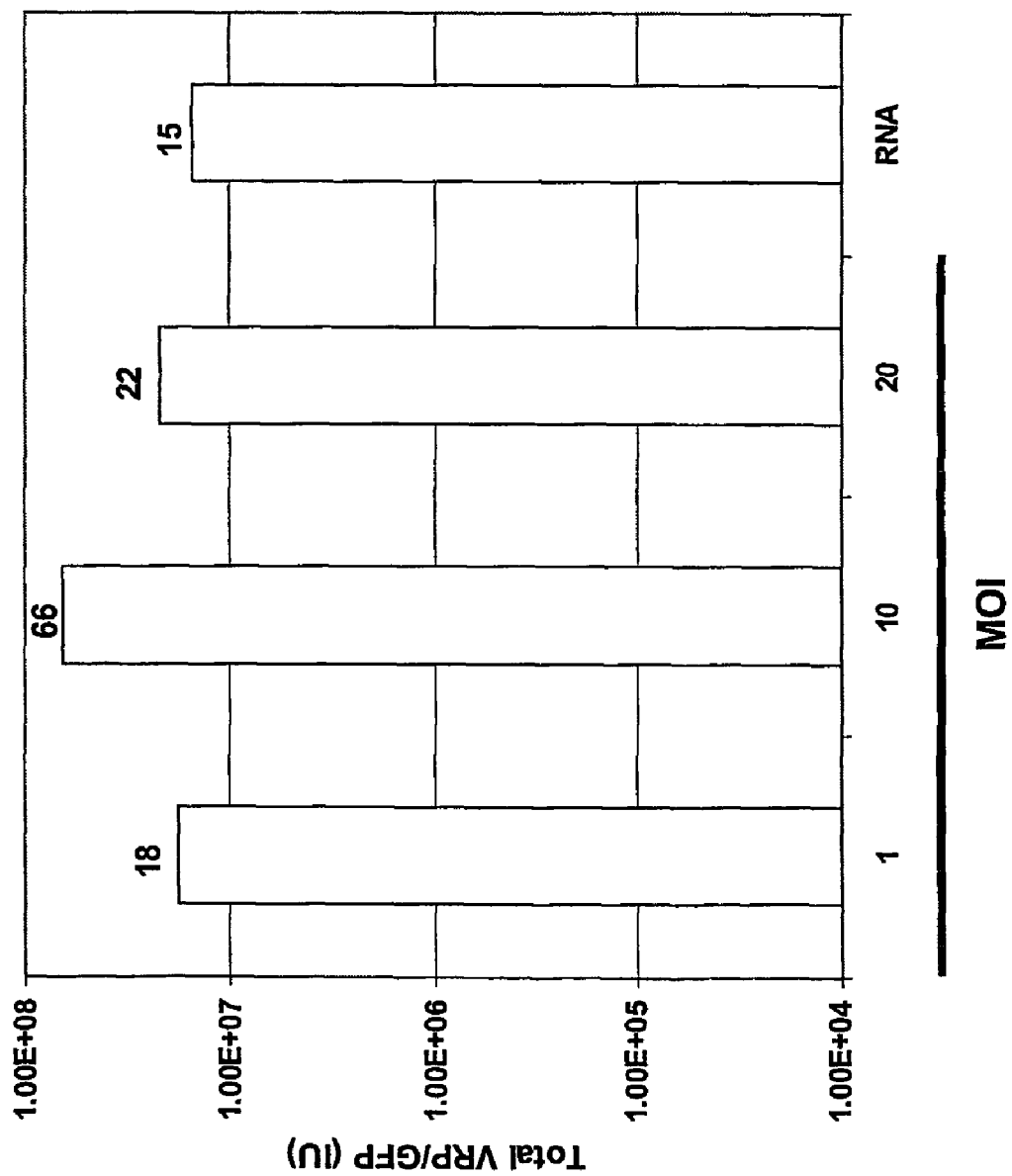
FIG. 14. VRP packaging with an exemplary MVA-based inducible VRP-packaging system. Approximately $1\times10^6$ Baby hamster kidney (BHK)-21 cells were co-infected with MVA/VEEGFP/DHgP (IMVA2) and MVGKT7/DHcap (IMVA1) at the indicated MOI, or alternatively they were co-transfected with replicon-GFP RNA, capsid and glycoprotein DH RNAs. VRP/GFP titers in the infected- and transfected-cell media were determined and plotted as total IU of VRP/GFP per 35 mm dish. Numbers above bars indicate the average number of VRP/GFP produced per cell.

Media from infected and electroporated cells were harvested at 24 h and titered on fresh BHK-21 cells. Additionally, some of the original infected and electroporated cells were trypsinized and counted at the time of harvest to calculate VRP production on a per-cell basis. The results showed that the inducible MVA-based VRP packaging system produced on the average between 20–60 VRP/cell, whereas the RNA transfection method yielded approximately 15 VRP/cell (see FIG. 14).

Although the MVA-based VRP packaging system produced more VRP than the split-helper RNA transfection method, the biosafety issues remained since replication-competent viruses might be generated during the replicon packaging process. This is due to the fact that both the inducible MVA-based VRP-packaging system and the in vitro RNA transfection method employ DH RNAs that are capable of recombining with the replicon.

Example 4

Characterization of a Constitutive MVA-Based VRP-Packaging System

The recombination rate between RNA species during an alphavirus infection has been estimated to be $10^{-6}$ per replication cycle (3). Furthermore, there appears to be a direct correlation between the length of replication sequences on the ends of the helper RNAs and the likelihood of recombination with the replicon RNA (27). To generate a replication-competent virus using a split-helper expression system two recombination events are required, significantly reducing the probability from $10^{-6}$ to $10^{-12}$. However, single-recombination events lead to a significant proportion of VRPs that have genomes capable of expressing one, but not both, of the structural genes in addition to the foreign gene. These particles could theoretically preclude repeated immunizations with recombinant VRPs by inducing a vector-specific immune response. In theory, if helper genes could be expressed as individual mRNAs that lack VEE-specific regulatory elements, instead of DH RNAs, the likelihood of producing replication-competent VEE by recombination would be further decreased. Furthermore, if a single recombination event took place between a helper mRNA and the VEE replicon, then the probability of expressing the helper gene would be infinitesimal since it lacks a subgenomic promoter.

Figure 15:
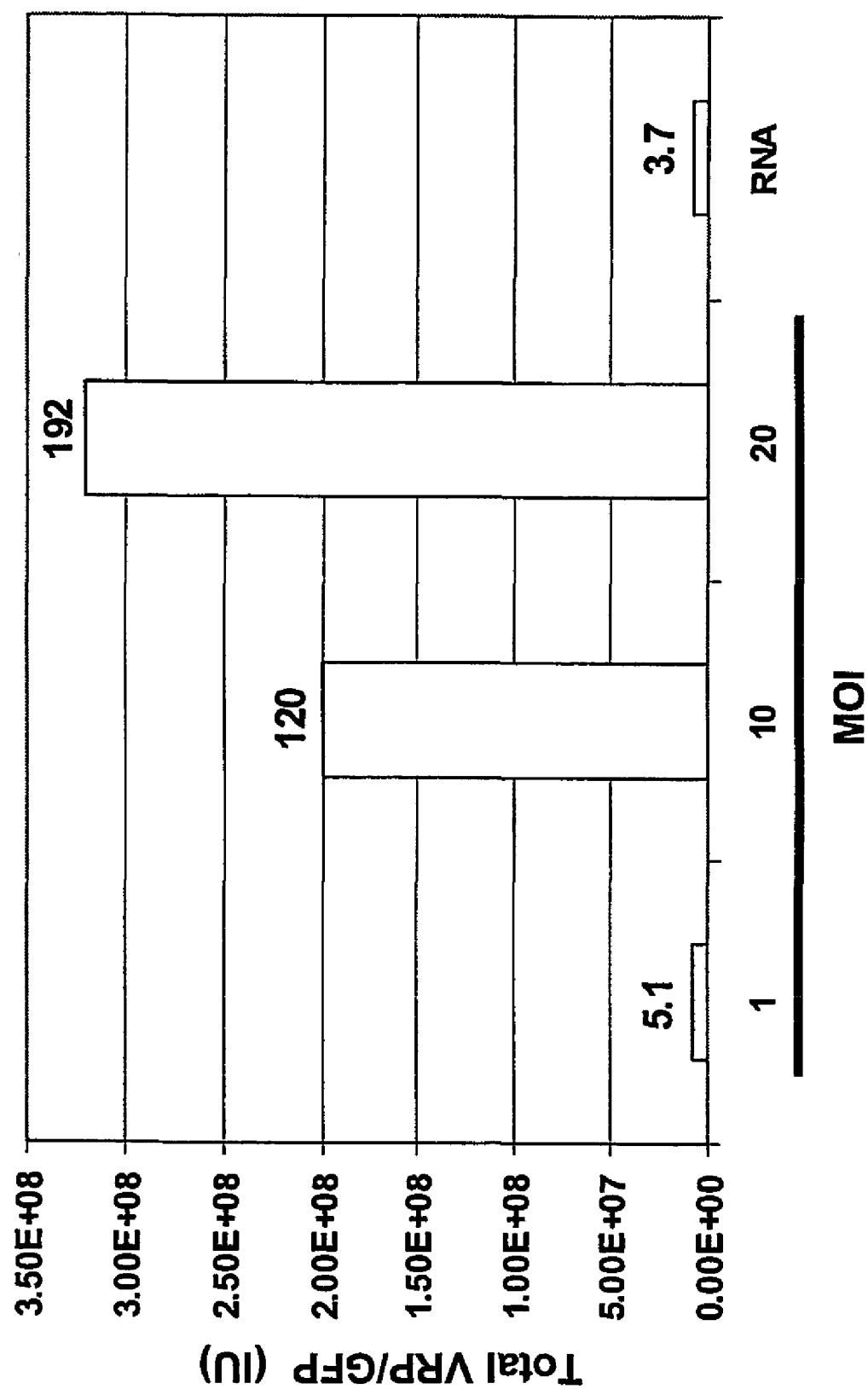
FIG. 15. VRP packaging with an exemplary MVA-based constitutive VRP-packaging system. BHK-21 cells were co-infected with MVA/VEEGFP/cap and MVGKT7/gP at the indicated MOI, or co-transfected as indicated in FIG. 5. Media from infected- and transfected-cells were titered for VRP/GFP. Titers are plotted as total IU of VRP/GFP per $1\times10^6$ cells. Numbers above bars indicate the average number of VRP/GFP yield per cell.

We observed in preliminary experiments that constitutive co-expression of the VEE capsid and glycoproteins by the same vector inhibited growth of recombinant MVAs. By inserting the capsid and glycoproteins genes into separate recombinant vectors, stable recombinant MVA viruses were isolated that grew to normal titers ($>10^8$ PFU/ml). Initial experiments were performed to determine the titers of VRP/GFP that are produced in BHK-21 cells co-infected with MVA/VEEGFP/cap (CMVA2) and MVGKT7/gP (CMVA1; exemplary constitutive system; see FIG. 8B), and to compare them to titers obtained by the split-helper RNA transfection method. Infections were performed with MOIs equivalent to 1, 10, or 20 PFU of total virus per cell. The media from infected and transfected cells were harvested at 24 h, and VRP/GFP titers were determined. Coinfection with the constitutive recombinant MVA viruses yielded titers as high as $2\times10^8$ IU per $1\times10^6$ cells, or approximately 190 VRP/GFP per cell (see FIG. 15). This system regularly yielded higher VRP titers than the DH RNA transfection method.

VRPs were also produced by providing a recombinant replicon and helper functions as transfected plasmids. BHK-21 cells were transfected with the following combination of plasmids: pGK63+pGK51+pGK53 or pGK63+pGK64+ pGK65. Subsequently, transfected cells were infected with MVGKT7. The media from transfected/infected cells was titered for VRP/GFP at 24 h. The titers of VRP/GFP were comparable to those obtained by co-transfection of a VEE replicon-GFP RNA and the two split-helper RNAs (data not shown).

Example 5

Figure 16:
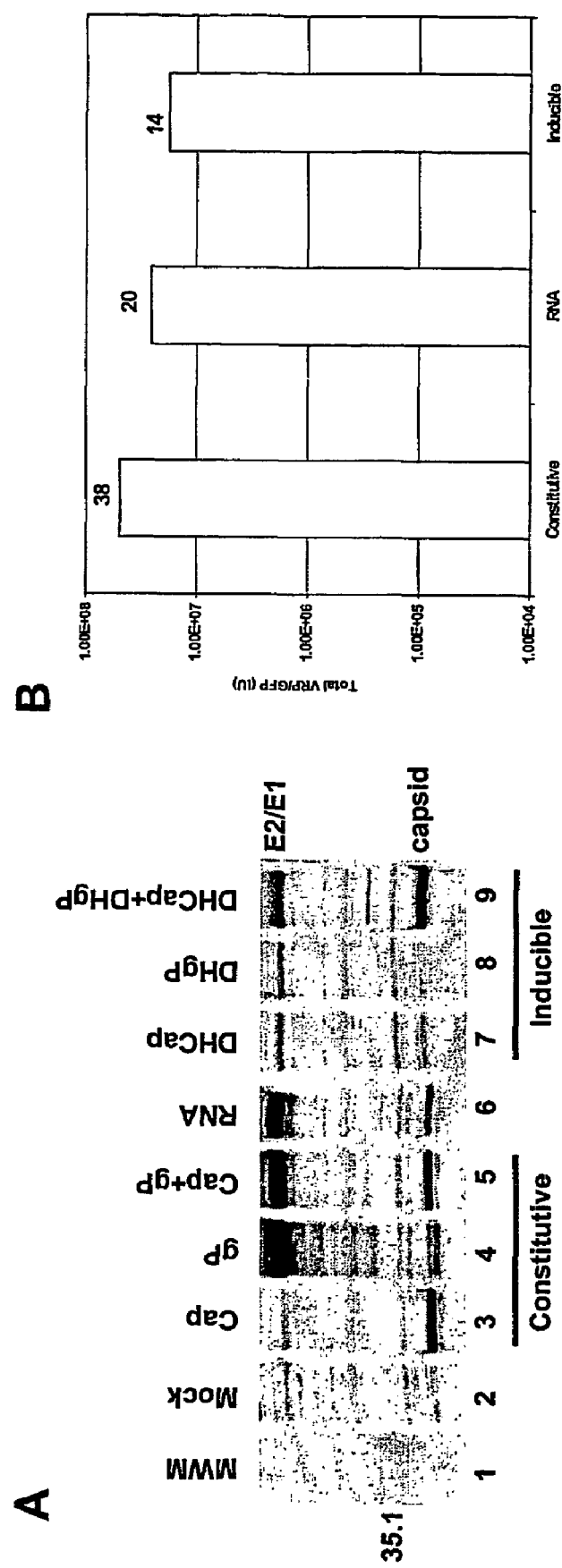
FIG. 16. Illustrates the expression of structural proteins by exemplary MVA-based VRP-packaging systems. Approximately, $1\times10^6$ BHK-21 cells were infected with either MVGKT7/gP and/or MVA/VEEGFP/cap (constitutive system) or MVA/VEEGFP/DHgP and/or MVGKT7/DHcap (inducible system) at a MOI equivalent to 5 PFU of each virus/cell. Alternatively, BHK-21 cells were co-electroporated with replicon-GFP RNA, and the capsid and glycoprotein DH RNAs. (A) Cell lysates were prepared at 24 h and analyzed by immunoblotting using a VEE-specific antiserum. Molecular weight markers are indicated at left. The expected immuno-reactive protein bands of capsid, E2/E1 are indicated at right. The size of a molecular weight marker is shown at the extreme left. MWM, molecular weight markers; Cap, MVA/VEEGFP/cap-infected; gP, MVGKT7/gP-infected; RNA, split-helper RNA electroporated; DHCap, MVGKT7/DHCap-infected; DHgP, MVA/VEE-GFP/DHgP-infected. (B) Infected- and transfected-cell media were harvested and titered on naïve BHK-21 cells. Total IU of VRP/GFP per 35 mm dish were determined. Numbers above bars indicate the average number of VRPs produced per cell.

Comparison of Structural Protein Expression Using MVA-Based VRP Packaging Systems and RNA Electroporation To determine the amounts of alphavirus capsid protein and glycoprotein produced by the MVA-based VRP packaging systems and the RNA electroporation method, lysates from infected and electroporated cells were analyzed by immunobloting. Twenty-four hpi, cell lysates were prepared and probed with anti-VEE antiserum. As shown in FIG. 16A, the expression of capsid (Cap), E1, and E2 (gP), is slightly higher in cells infected with the constitutive MVA-based VRP-packaging system than with the inducible MVA-based VRP-packaging system or RNA electroporation. FIG. 16A also illustrates that expression of the VEE structural genes is possible only when cells are coinfected with both of the exemplary inducible recombinant MVA viruses. In contrast, the respective structural genes in the individual constitutive recombinant MVA viruses are expressed independent of coinfection (see FIG. 16A, compare lanes 3, 4, and 5 to lanes 7, 8, and 9). Lastly, infected- and transfected-cell media were titered for the presence of VRP/GFP (FIG. 16B). The results indicate that there is a direct correlation between VRP titers and the amount of structural proteins produced by each packaging system.

Example 6

VRP Packaging in Cells that are Restrictive for MVA Growth

Figure 17:
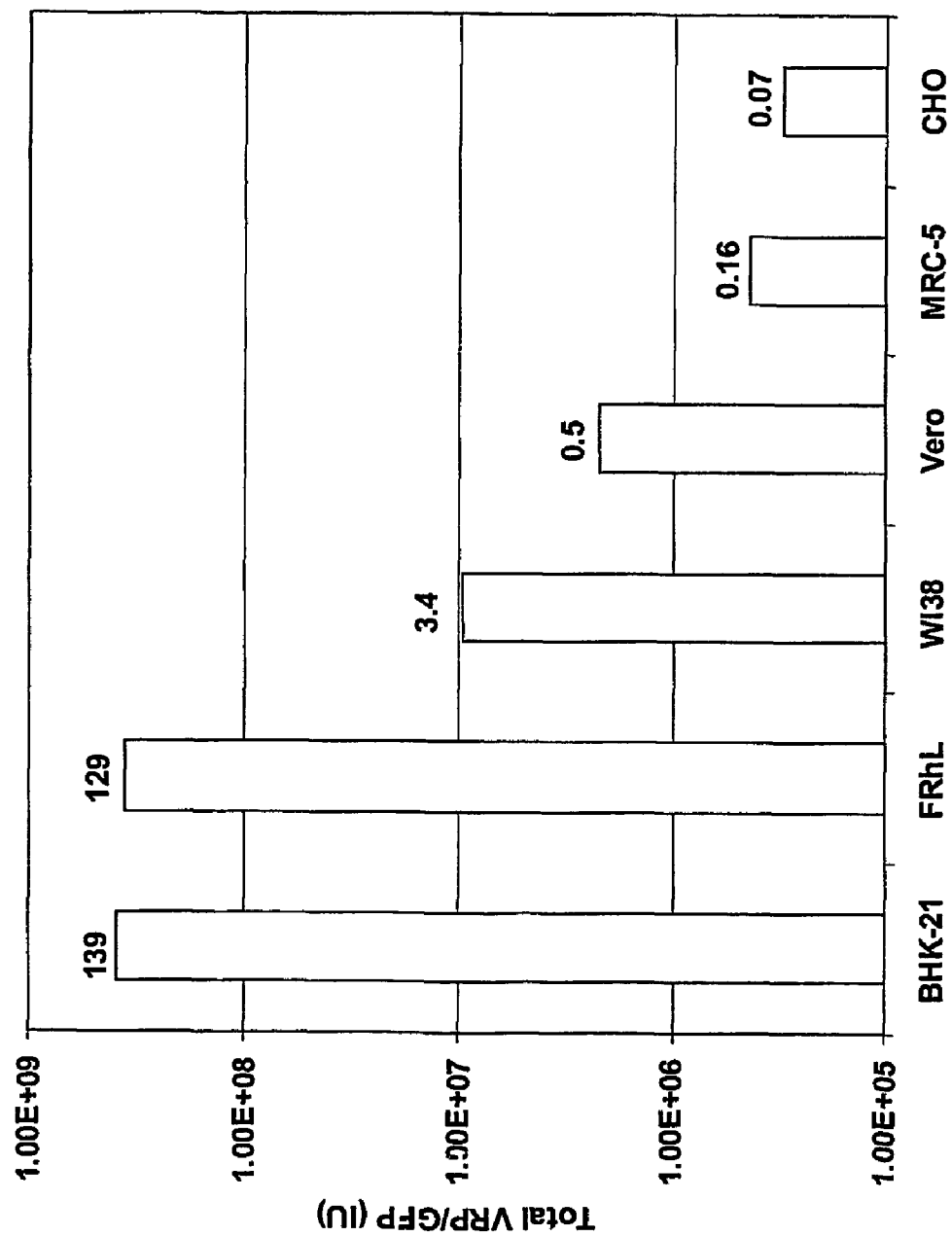
FIG. 17. VRP packaging on cell lines that are restrictive for MVA growth. Approximately $2.5 \times 10^6$ of the indicated cell lines were co-infected with MVA/VEEGFP/cap and MVGKT7/gP at 10 PFU of each virus per cell. Infected-cell media were titered for VRP/GFP at 24 hpi and plotted as total IU produced per T-25 flask. Numbers above bars indicate the average number of VRPs produced per cell.
Figure 19:
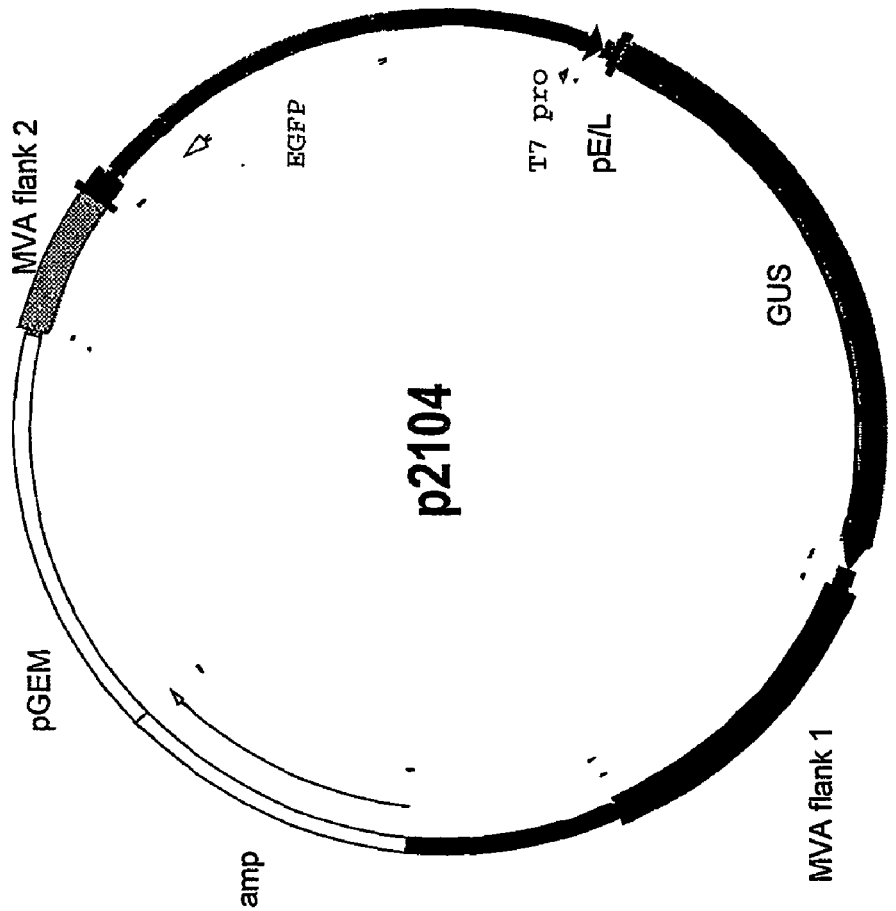
FIG. 19. Shows a schematic representation of the plasmid transfer vector, p2104, used for construction of an MVA recombinant, which will be used to deliver a reporter gene to cells.
Figure 20:
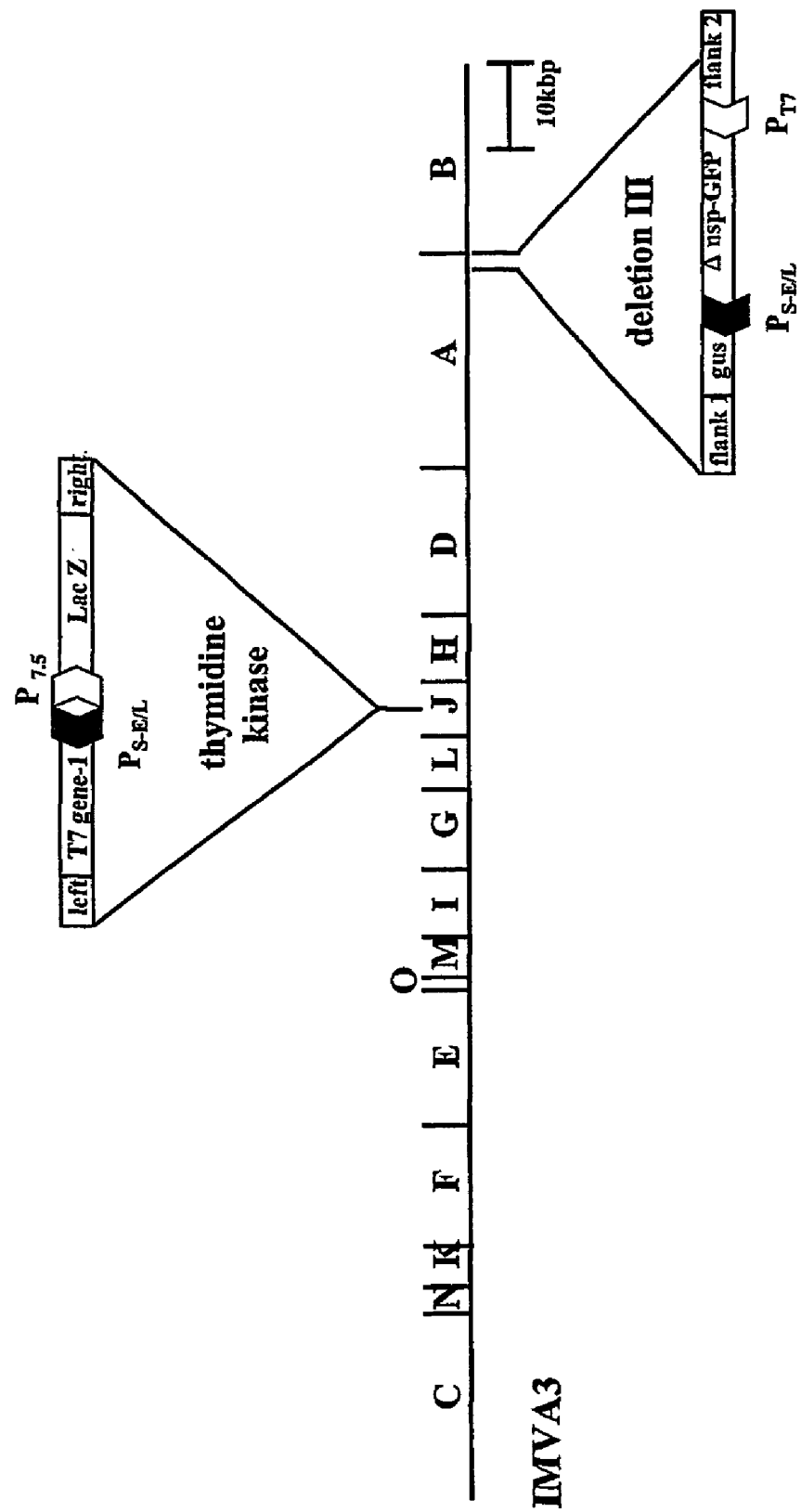
FIG. 20. Shows a schematic representation of the MVA recombinant, IMVA3, after recombination of the p2104 transfer vector into deletion III.
Figure 21:
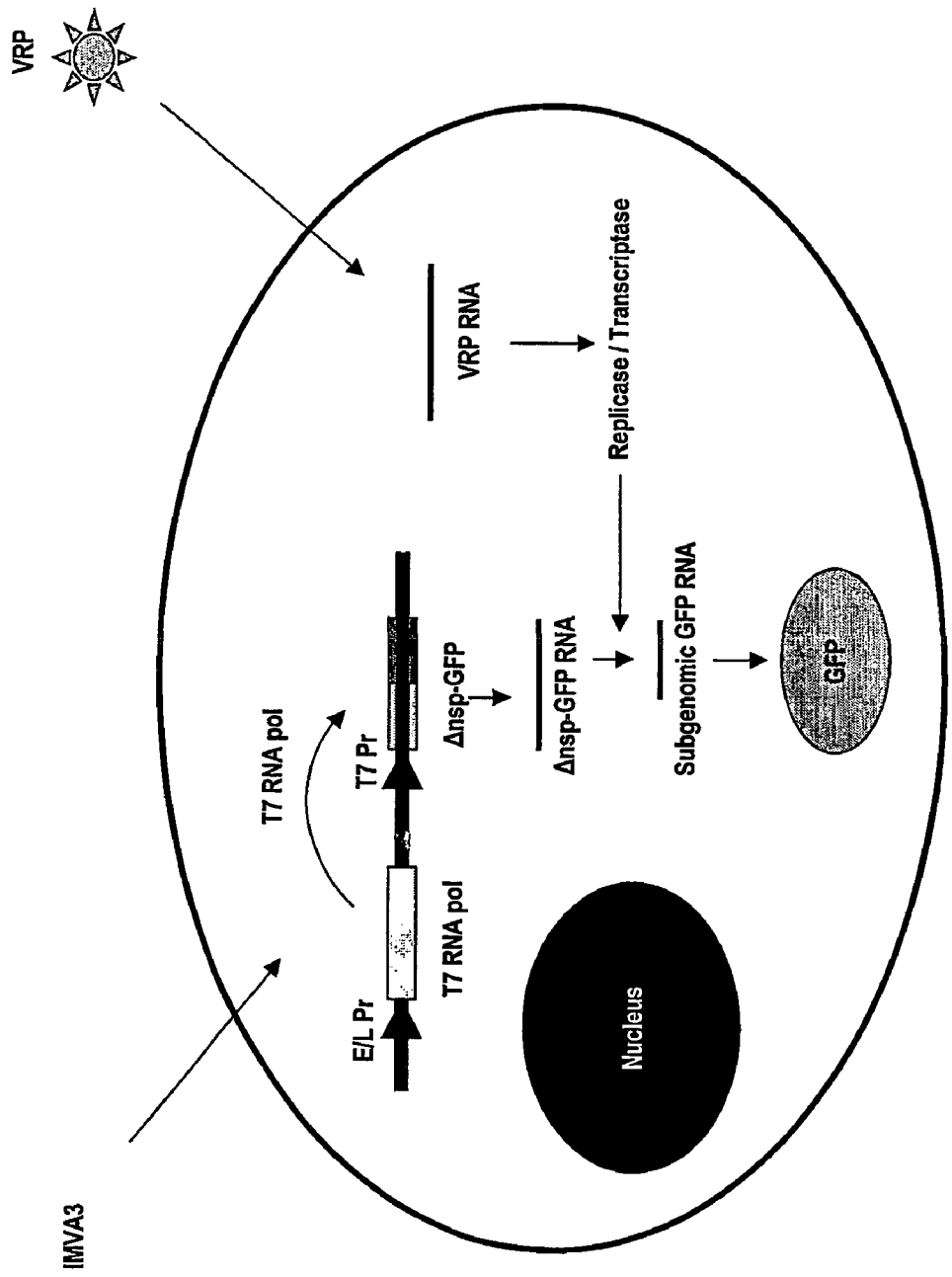
FIG. 21. Depicts the universal replicon titration system diagrammatically.
Figure 22:
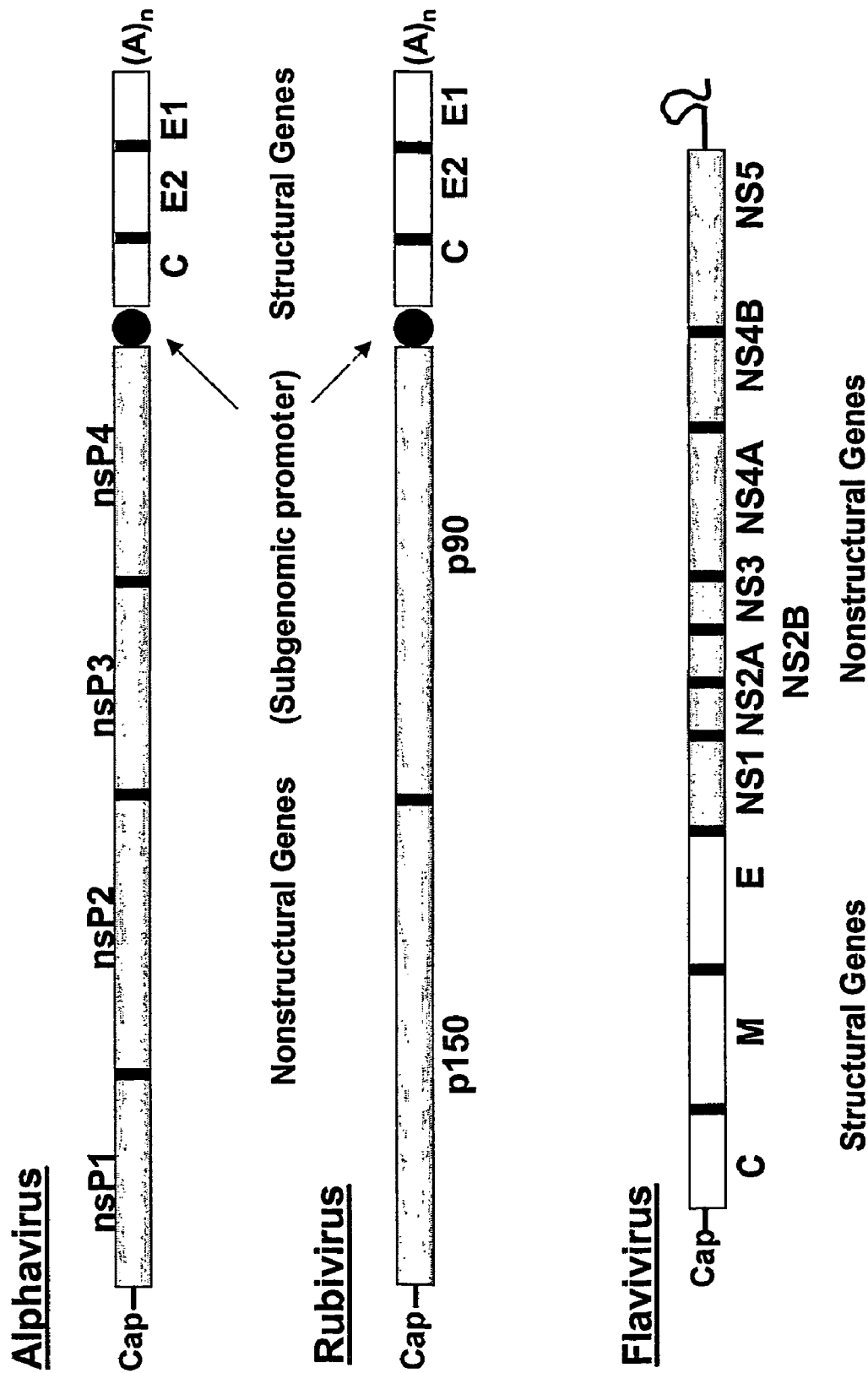
FIG. 22. Depicts the genomes of two members of the Alphaviridae (alphavirus and rubivirus) and one representative virus of the Flaviviridae. Nonstructural genes are indicated in shaded boxes, and structural genes are shown as stippled boxes.
Figure 23:
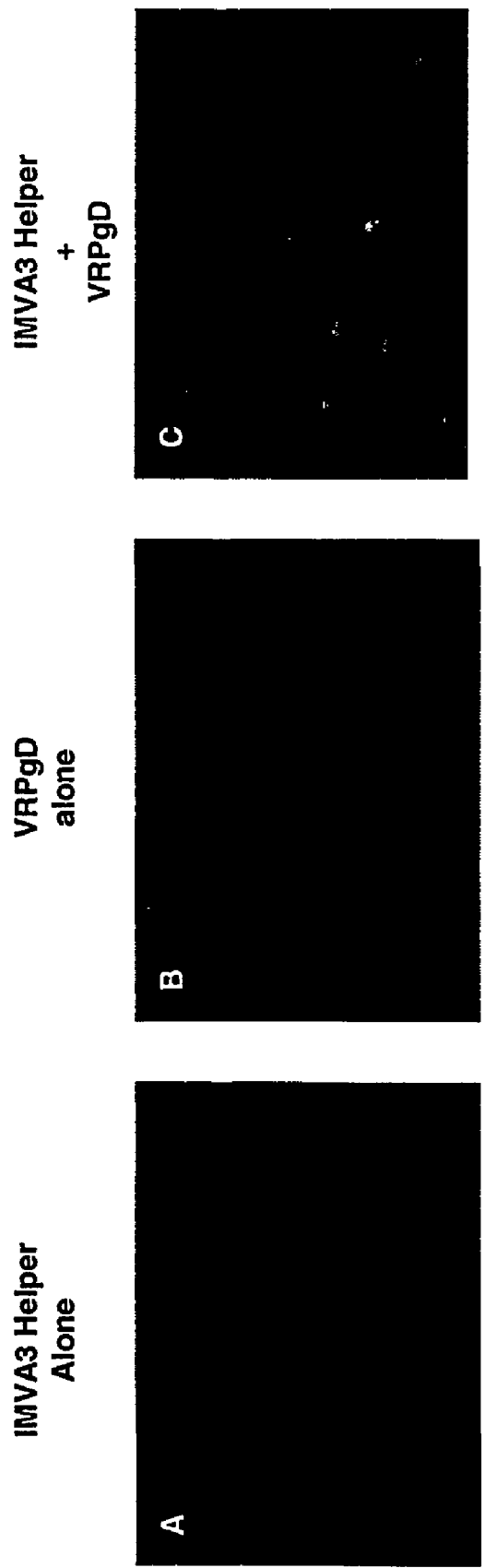
FIG. 23. Titering of VRPgD using the IMVA3-based GFP indicator system. Confluent cultures of VERO cells were infected with IMVA3 indicator virus (panels A and C), and/or VRPgD replicon particles (panels B and C). Cells were observed with UV fluorescence microscopy at 24 hours post infection.

Since BHK-21 cells are fully permissive for MVA growth, they are not an ideal cell line for MVA-based VRP packaging systems. A panel of cells that were restrictive for MVA growth was tested in a VRP packaging experiment. Equivalent numbers of cells were infected with 10 PFU/cell of MVA/VEEGFP/cap and MVGKT7/gP (constitutive system) and incubated for 24 h. Media from infected-cells were harvested and VRP/GFP titers were determined on fresh BHK-21 cells. As shown in FIG. 17 two human cell lines (MRC-5 and WI38), one hamster cell line (CHO), and a nonhuman primate cell line (Vero) yielded VRP titers that were significantly lower than those obtained with BHK-21 cells. Surprisingly, fetal Rhesus monkey lung (FRhL) cells produced VRP/GFP titers as high as BHK-21.

Example 7

The Growth of MVA is Severely Inhibited During VRP-packaging

One potential limitation to using the MVA-based VRP packaging systems is that VRP preparations could be contaminated with MVA recombinants even though VRPs bud from the cell membrane while most of the MVA virus remains cell-associated. As shown in Example 2, MVA late gene expression is inhibited by VEE replication. To measure the level of MVA growth inhibition, BHK-21 cells (permissive for MVA growth) or FRhL cells (restrictive for MVA growth) were infected with MVGKT7/gP alone or together with MVA/VEEGFP/cap. Infection with MVGKT7/gP alone would not result in either VEE replication or production of VRP. Coinfection with MVA/VEEGFP/cap, however, results in VEE replicon replication and VRP production (see FIG. 15). The media from single-infected and coinfected cells were harvested at 24 hpi, and recombinant MVA viruses were titered on CEF. The host-range growth restriction is clearly shown in FRhL cells infected with MVGKT7/gP alone (Table 2). For example, in the absence of VEE replication, the average PFU/cell produced in BHK-21 and FRhL cells was 435 and 0.6 PFU/cell, respectively. When coinfected with MVAGKT7/gP and MVAVEEGFP/cap, the average PFU/cell was decreased to 1.1 in BHK-21 cells (normally permissive), and to 0.007 in FRhL cells. Thus, consistent with the results obtained in Example 2, there is a great reduction in MVA growth during VEE replication.

Example 8

Method for Titering VRPs Using an MVA Indicator Virus

This section describes a method for titering VEE replicon particles (VRPs) that makes use of recombinant MVA viruses similar to those used in packaging these particles. Briefly, an MVA recombinant is used to deliver a reporter gene to a suitable cell line growing in culture. Coinfection of these cells with replicon particles activates the reporter gene of the MVA indicator virus so that the infected cells can be detected, counted, and thus a titer for the preparation can be determined.

This titering system fulfills an important need in the use of VRPs for research, gene expression, and vaccine production. Currently the only practical method of titering a VRP preparation is by immunohistochemistry, using an antibody directed against the foreign protein or a tag engineered on the foreign protein encoded by the VRP. However, antibodies are not always available for the specific gene products, and making antibodies is a lengthy process requiring the isolation and purification of immunogens.

This assay makes use of the fact that all functional replicon particles encode VEE non-structural proteins (nsPs) that replicate and transcribe VEE RNA. By assaying for functional nsP, this assay is capable of measuring titers of VRPs independently of the foreign gene products that they express. This makes comparisons between VRP preparations more accurate, especially in cases where the sensitivity of detection by immuno-detection is significantly different between preparations.

The plasmid transfer vector for construction of such an MVA virus indicator (p2104) is diagrammed in FIG. 19. It consists of two gene cassettes, a gene coding for a defective VEE RNA encoding green fluorescent protein (GFP) under control of the phage T7 transcriptional promoter, and the glucuronidase (gus) gene under control of a vaccinia synthetic early-late promoter, as a selectable marker. The structure of the defective VEE RNA is similar to the "replicon-like helper RNA" referred to above. Thus, the RNA that is produced has 5' and 3' ends identical to that of VEE viral RNA, 90% of the region of VEE coding for nsPs is deleted, and the VEE sub-genomic promoter directs the synthesis of a protein product. However, instead of coding for either VEE glycoproteins or VEE capsid protein, this RNA encodes the GFP reporter protein. The gus gene serves to enable isolation of recombinant viruses. These two gene cassettes in p2104 are flanked by MVA sequences that direct the recombination of this plasmid into deletion III of MVA. The p2104 plasmid is recombined into deletion III of an MVA that already encodes T7 RNA polymerase under a synthetic early/late promoter at the thymidine kinase locus (MVGKT7; see FIG. 2). The resulting virus (IMVA3, FIG. 20) is used as an indicator in the titration assay.

The universal replicon titering system is depicted in FIG. 21. A cell line that is non-permissive for MVA but permissive for VEE replication is used (e.g. Vero). Cells are infected with the IMVA3 indicator virus at a multiplicity of 5 to ensure that all cells in the culture are infected. This virus synthesizes T7 RNA polymerase, which recognizes the T7 promoter (T7 Pr) and transcribes the defective "VEE-like" RNA coding for GFP (nsP-GFP). Since the start of translation is approximately 500 bases from the 5' end of this RNA and since several stop codons are positioned before the GFP open reading frame, GFP is not translated from this RNA. The MVA indicator-infected cultures are co-infected with serial dilutions of a VRP preparation of unknown titer. The VRP delivers, to the cytoplasm of the MVA indicator-infected cell, its replicon RNA which is immediately translated to produce the VEE replicase-transcriptase complex encoded by the nsP gene. The VEE replicase initiates replication of the defective GFP RNA, and also transcribes the subgenomic promoter present on the minus-strand (antisense) replication intermediate. This results in the synthesis of large quantities of mRNA encoding GFP (subgenomic GFP RNA) Translation of the GFP mRNA causes the cell to fluoresce under UV light. The fluorescent cells are counted and the titer of the original stock of VRPs is determined by extrapolation.

The IMVA3 indicator virus was tested for its ability to titer a VEE replicon particle expressing the herpes simplex virus glycoprotein D (VRPgD). Confluent cultures of Vero cells were infected with IMVA3 at a MOI equivalent to 10 PFU/cell, or with IMVA3 at an MOI of 10 PFU/cell plus serial dilutions of a VRPgD preparation of unknown titer. Cells were fixed at 24 hpi with 2% formaldehyde and visualized using fluorescent microscopy (FIG. 23). The results indicate that GFP is not expressed unless cells are coinfected with both a replicon particle and the IMVA3 indicator virus. Panel C of FIG. 23 shows a representative field in the VRPgD dilution series.

Interference between VEE replication and MVA gene expression is not an issue since we have already established, with data presented in Example 2 (Table 1), that MVA infection actually enhances VEE replication. We also showed that it is only late MVA gene expression that is inhibited by VEE (FIG. 13). Accordingly, this assay makes use of a vaccinia promoter that functions early as well as late.

A universal assay for Sindbis virus replicons has been previously described (53). This system uses a defective RNA encoding a reporter gene whose transcription was under the control of a cellular RNA polymerase II promoter. In order to use this system, it would first be necessary to isolate stable cell lines expressing the transcript. The isolation of stable mammalian cell lines is a time consuming and laborious undertaking. An MVA-based reporter system significantly reduces the labor in setting up such an assay.

Example 9

Method for Amplifying Replicon Particles

In addition to its utility as a means of producing alphavirus replicon particles de novo, it is also possible to amplify alphavirus replicon particles using the MVA expression vectors. To amplify a preparation of alphavirus replicon particles one coinfects a cell line (eg. fetal rhesus lung, or FRhL) with the replicon particle preparation at a low MOI (1–5 IU/cell) and a higher MOI of MVA recombinant viruses (5–20 PFU/cell) that express the structural genes needed for packaging. At 24–48 hpi, the medium is collected and newly packaged replicon particles are purified as described in Example 1.

Provided below is a list of references which are expressly incorporated herein for any purpose.

1. Baldick, C. J., J. G. Keck, and B. Moss. 1992. Mutational analysis of the core, spacer and initiator regions of vaccinia virus intermediate class promoters. J. Virol. 66:4710–4719.
2. Barrett, N., A. Mitterer, W. Mundt, J. Eibl, M. Eibl, R. C. Gallo, B. Moss, and F. Dorner. 1989. Large-scale production and purification of a vaccinia recombinant-derived HIV-1 gp160 and analysis of its immunogenicity. AIDS Res. Human Retroviruses. 5:159–171.
3. Berglund, P., M. Sjoberg, H. Garoff, G. J. Atkins, B. J. Sheahan, and P. Liljestrom. 1993. Semliki Forest virus expression system: production of conditionally infectious recombinant particles. Bio/Technology. 11:916–920.
4. Blanchard, T. J., A. Alcami, P. Andrea, and G. L. Smith. 1998. Modified vaccinia virus Ankara undergoes limited replication in human cells and lacks several immunomodulatory proteins: implications for use as a human vaccine. Journal of General Virology. 79:1159–1167.
5. Bredenbeek, P. J., I. Frolov, C. M. Rice, and S. Schlesinger. 1993. Sindbis virus expression vectors: packaging of RNA replicons by using defective helper RNAs. J. Virol. 67:6439–6446.
6. Carroll, M., and B. Moss. 1997. Host range and cytopathogenicity of the highly attenuated MVA strain of vaccinia virus: propagation and generation of recombinant viruses in a nonhuman mammalian cell line. Virology:198–211.
7. Carroll, M. W., and B. Moss. 1995. *E. coli* β-glucuronidase (GUS) as a marker for recombinant vaccinia viruses. BioTechiques. 19:352–354.
8. Chakrabarti, S., K. Brechling, and B. Moss. 1985. Vaccinia virus expression vector: Coexpression of β-galactosidase provides visual screening of recombinant virus plaques. Mol. Cell. Biol. 5:3403–3409.
9. Chakrabarti, S., J. R. Sisler, and B. Moss. 1997. Compact, synthetic, vaccinia virus early/late promoter for protein expression. BioTechniques. 23:1094–1097.
10. Davis, N. L., Powell, N., Greenwald, G. F., Willis, L. V., Johnson, B. J. B., Smith, J. F., Johnston, R. E. 1991. Attenuating mutations in the E2 glycoprotein gene of Venezuelan equine encephalitis virus: Construction of single and multiple mutants in the a full-length cDNA clone. Virology. 183:20–31.
11. Davis, N. L., Willis, L. V., Smith, J. F., Johnston, R. E. 1989. In vitro synthesis of infectious Venezuelan equine encephalitis virus RNA from a cDNA clone: Analysis of a viable deletion mutant. Virology. 171:189–204.
12. Davis, N. L., K. W. Brown, and R. E. Johnston. 1996. A viral vaccine vector that expresses foreign genes in lymph nodes and protects against mucosal challenge. Journal of Virology. 70:3781–3787.
13. Drexler, I., K. Heller, B. Wahren, V. Erfle, and G. Sutter. 1998. Highly attenuated modified vaccinia virus Ankara replicates in baby hamster kidney cells, a potential host for virus propagation, but not in various human transformed and primary cells. Journal of General Virology. 79:347–352.
14. Frolov, I., Hoffman, T. A., Pragai, B. M., Dryga, S. A., Huang, H. V., Schlesinger, S., Rice, C. M. 1996. Alphavirus-based expression vectors: Strategies and Applications. Proceedings of the National Academy of Sciences, USA. 93:11371–11377.
15. Garoff, H., and K. J. Li. 1998. Recent advances in gene expression using alphavirus vectors. Curr. Opin. Biotechnol. 9.
16. Hewson, R. 2000. RNA viruses: emerging vectors for vaccination and gene therapy. Molecular Medicine Today. 6:28–35.
17. Johnston, R. E., and C. J. Peter. 1996. Alphaviruses, 3 ed, vol. 1. Lippincott-Raven, Philadelphia.
18. Kuhn, R. J., H. G. M. Niesters, Z. Hong, and J. H. Strauss. 1991. Infectious RNA transcripts from Ross River virus cDNA clones and the costruction and characterization of defined chimeras with Sindbis virus. Virology. 182:430–441.
19. Liljestrom, P., and H. Garoff. 1991. A new generation of animal cell expression vectors based on the semliki forest virus replicon. Bio/technology. 9:1356–1361.
20. Liljestrom, P., S. Lusa, D. Huylebroeck, and H. Garoff. 1991. In vitro mutagenesis of a full-length cDNA clone of Semliki Forest virus: the small 6,000-molecular weight membrane protein modulates virus release. Journal of Virology. 65.
21. Lundstrom, K. 1997. Alphaviruses as expression vectors. Curr. Opin. Biotechnol. 8.
22. Mackett, M., G. L. Smith, and B. Moss. 1984. General method for production and selection of infectious vaccinia virus recombinants expressing foreign genes. J. Virol. 49:857–864.
23. Mayr, A., V. Hochstein-Mintzel, and H. Stickl. 1975. Abstammung, eigenschaften und verwendung des aftenuierten vaccinia-stammes MVA. Infection. 3:6–14.
24. Mayr, A., and E. Munz. 1964. Veränderung von vaccinevirus durch dauerpassagen in hühnerembryofibroblastenkulturen
Changes in vaccine virus caused by prolonged passage through chick embryo fibroblast cultures (A contribution to the specialization of vaccine virus strains towards original pox viruses). Zbl. Bakt. Orig. I. 195:25–35.
25. Mayr, A., H. Stickl, H. K. Müller, K. Danner, and H. Singer. 1978. Der pockenimpfstamm MVA: Marker, genetische struktur, erfahrungen mit der parenteralen schutzimpfung und verhalten im abwehrgeschwächten organismus. The smallpox vaccination strain MVA: Marker, genetic structure, experience gained with the parenteral vaccination and behavior in organisms with a debilitated defence mechanism. Zbl. Bakt. Hyg. 167: 375–390.
26. Polo, J. M., B. A. Belli, D. A. Driver, I. Frolov, S. Sherrill, M. J. Hariharan, K. Townsend, S. Perri, S. J. Mento, D. J. Jolly, S. M. W. Chang, S. Schlesinger, and T. W. Dubensky. 1999. Stable alphavirus packaging cell lines for Sindbis virus and Semliki Forest virus-derived vectors. Proc. Natl. Acad. Sci. USA. 96:4598–4603.
27. Pushko, P., M. Parker, G. V. Ludwig, N. L. Davis, R. E. Johnston, and J. F. Smith. 1997. Replicon-helper systems from attenuated Venezuelan equine encephalitis virus: Expression of heterologous genes in vitro and immunization against heterologous pathogens in vivo. Virology. 239:389–401.
28. Meyer, H., G. Sutter, and A. Mayr. 1991. Mapping of deletions in the genome of the highly attenuated vaccinia virus MVA and their influence on virulence. J. Gen. Virol. 72:1031–1038.
29. Raju, R., S. V. Subramanian, and M. Hajjou. 1995. Identification of a region in the Sindbis virus nucleocapsid protein that is involved in specificity of RNA encapsidation. Journal of Virology. 69:7391–7401.
30. Rice, C. M. 1996. Alphavirus-based expression systems. Plenum Press, New York.
31. Rice, C. M., R. Levis, J. H. Strauss, and H. V. Huang. 1987. Production of infectious transcripts from Sindbis virus cDNA clones: mapping of lethal mutations, rescue of a temperature-sensitive marker and in vitro mutagenesis to generate defined mutants. Journal of Virology. 61:3809–3819.
32. Schlesinger, S., and M. Schlesinger. 1996. Togaviridae: The Viruses and Their Replication, 3rd ed, vol. I. Lipincott-Raven Publishers, Philadelphia.
33. Smerdou, C., and P. Liljestrom. 1999. Two-helper RNA system for production of recombinant Semliki Forest Virus Particles. Journal of Virology. 73:1092–1098.
34. Strauss, J. H., and E. G. Strauss. 1994. The alphaviruses: Gene expression, replication, and evolution. Microbiological Reviews. 58:491–52.
35. Strauss, J. H., and E. G. Strauss. 1997. Recombination in alphaviruses. Seminars in Virology. 8:85–94.
36. Sutter, G., and B. Moss. 1992. Nonreplicating vaccinia vector efficiently expresses recombinant genes. Proc. Natl. Acad. Sci. USA. 89:10847–10851.
37. Weiss, B. G., and S. Schlesinger. 1991. Recombination between Sindbis virus RNAs. J. Virol. 65:4017–4025.
38. Sambrook et al. 1989. Molecular Cloning—A Laboratory Manual. Cold Spring Harbor Press (Cold Spring Harbor, N.Y.).
39. Ausbel et al. 1993 (including supplements through August 2000). Current Protocols in Molecular Biology. John Wiley & Sons.
40. Beaucage et al. 2000. Current Protocols in Nucleic Acid Chemistry. John Wiley & Sons.
41. Antoine, et al. 1998. The complete genomic sequence of the modified vaccinia virus Ankara strain: comparison with other orthopoxviruses. Virology 244: 365–96.
42. Antoine, G., F. Scheiflinger, G. Holzer, T. Hangmann, F. G. Falkner, and F. Domer. 1996. Characterization of the vaccinia MVA hemagglutinin gene locus and its evaluation as an insertion site for foreign genes. Gene:43–46.
43. Blanchard, T. J., A. Alcami, P. Andrea, and G. L. Smith. 1998. Modified vaccinia virus Ankara undergoes limited replication in human cells and lacks several immunomodulatory proteins: implications for use as a human vaccine. Journal of General Virology. 79:1159–1167.

44. Carroll, M., and B. Moss. 1997. Host range and cytopathogenicity of the highly attenuated mVA strain of vaccinia virus: propagation and generation of recombinant viruses in a nonhuman mammalian cell line. Virology:198–211.
45. Chakrabarti, S., J. R. Sisler, and B. Moss. 1997. Compact, synthetic, vaccinia virus early/late promoter for protein expression. BioTechniques. 23:1094–1097.
46. Drexler, I., K. Heller, B. Wahren, V. Erfle, and G. Sutter. 1998. Highly attenuated modified vaccinia virus Ankara replicates in baby hamster kidney cells, a potential host for virus propagation, but not in various human transformed and primary cells. Journal of General Virology. 79:347–352.
47. Hammond, J. M., P. G. Oke, and B. E. H. Coupar. 1997. A synthetic vaccinia virus promoter with enhanced early and late activity. Journal of Virological Methods. 66:135–138.
48. Kovacs, G. R., and B. Moss. 1996. The vaccinia virus H5R gene encodes viral late gene transcription factor-4: purification, cloning and overexpression. Journal of Virology. 70:6796–6802.
49. Altenburger, W., C.-P. Süter, and J. Altenburger. 1989. Partial deletion of the human host range gene in the attenuated vaccinia virus MVA. Arch. virol. 105:15–27.
50. Hirsch, V. M., S. Goldstein, R. Chanock, W. R. Elkins, G. Suffer, B. Moss, J. Sisler, J. Lifson, and T. Fuerst. 1995. Limited virus replication following SIV challenge of macaques immunized with attenuated MVA vaccinia expressing SIVsm env and gag-pol Vaccines 95:195–200.
51. Meyer, H., G. Suffer, and A. Mayr. 1991. Mapping of deletions in the genome of the highly attenuated vaccinia virus MVA and their influence on virulence. J. Gen. Virol. 72:1031–1038.
52. Schleiflinger, F., Falkner, F. G., and Dorner, F. 1996. Evaluation of the thymidine kinase (TK) locus as an insertion site in highly attenuated vaccinia virus MVA strains. Archives of Virology 141:663–69.
53. Olivo, P. D., Frolov, I., and Schlesinger, S. 1994. A cell line that expresses a reporter gene in response to infection by Sindbis virus: a prototype for detection of positive strand RNA viruses. Virology 198: 381–384.
54. Strauss, J. H., and Strauss. 2001. E.G. Virus Evolution: How Does an Enveloped Virus Make a Regular Structure. Cell 105: 5–8.
55. Behrens, S. E., Grassmann, C. W., Thiel, H. J., Meyers, G., and Tautz, N. 1998. Characterization of an autonomous subgenomic pestivirus RNA replicon. J. Virol. 72: 2364–2374.
56. Pietschmann, T., Lohmann, V., Rutter, G., Kurpanek, K., and Bartenschlager, R. 1991. Characterization of cell lines carrying self-replicating hepatitis C virus RNAs. J. Virol. 75: 1252–1264.
57. Khromykh, A. A., Vamavski, A. N., and Westaway, E. G. 1998. Encapsidation of the flavivirus Kunjin replicon RNA by using a complementation system providing Kunjin virus structural proteins in trans. J. Virol. 72: 5967–5977.
58. Porter, D., Ansardi, D.C., and Morrow, C. D. 1995. Encapsidation of Poliovirus Replicons Encoding the Complete Human Immunodeficiency Virus Type 1 gag Gene by Using a Complementation System Which Provides the P1 Capsid Protein in trans. J. Virol. 69: 1548–1555.
59. Almazan, F., Gonzalez, J. M., Penzes, Z., Izeta, A., Calvo, E., and Plana-Duran, J. 2000. Engineering the largest RNA virus genome as an infectious bacterial artificial chromosome. PNAS 97: 5516–5521

Although the invention has been described with reference to various applications, methods, and compositions, it will be appreciated that various changes and modifications may be made without departing from the invention.

What is claimed is:

1. A recombinant DNA polynucleotide comprising: a first portion comprising a DNA sequence encoding a DNA-dependent RNA polymerase operatively linked to a first heterologous promoter; and a second portion comprising either (i) a sequence encoding at least one structural protein of a positive-strand RNA virus (psRNAV), but not all of the structural proteins of said psRNAV, operatively linked to a second heterologous promoter or (ii) a second portion comprising a DNA sequence encoding a replicon-like psRNAV helper RNA sequence operatively linked to a second heterologous promoter; or (iii) a second portion comprising a DNA sequence encoding a replicon-like PSRNAV helper RNA sequence comprising a reporter gene operatively linked to a second heterologous promoter.

2. The recombinant polynucleotide of claim 1, wherein the DNA-dependent RNA polymerase of the first portion is selected from T3, T7, and SP6 DNA-dependent RNA polymerase; wherein the first heterologous promoter is a poxvirus promoter; wherein the at least one psRNAV structural protein of the second portion is an alphavirus structural protein selected from an alphavirus capsid and an alphavirus glycoprotein; and wherein the second heterologous promoter binds to said DNA-dependent RNA polymerase.

3. The recombinant polynucleotide of claim 2, wherein the DNA-dependent RNA polymerase of the first portion is a T7 polymerase; wherein the poxvirus promoter is a vaccinia virus synthetic early/late promoter; wherein the second heterologous promoter binds to a T7 DNA-dependent RNA polymerase; and wherein the alphavirus capsid is a Venezuelan equine encephalitis virus (VEE) capsid and the alphavirus glycoprotein is a VEE glycoprotein.

4. The recombinant polynucleotide of claim 1, wherein the at least one psRNAV structural protein of the second portion is selected from an alphavirus structural protein, a rubella virus structural protein, a coronavirus structural protein, a dengue virus structural protein, and a Hepatitis C virus structural protein.

5. A recombinant DNA polynucleotide comprising: a first portion comprising a sequence encoding at least one structural protein of a psRNAV, but not all of the structural proteins of said psRNAV, operatively linked to a first heterologous promoter; and a second portion comprising a second heterologous promoter operatively linked to a psRNAV replicon comprising an psRNAV subgenomic promoter operatively linked to a sequence encoding at least one foreign polypeptide.

6. The recombinant polynucleotide of claim 5, wherein the at least one psRNAV structural protein is an alphavirus structural protein selected from an alphavirus capsid and an alphavirus glycoprotein; and wherein the first and second heterologous promoters both bind to a polymerase selected from T3, T7, and SP6 DNA-dependent RNA polymerase.

7. The recombinant polynucleotide of claim 6, wherein the alphavirus capsid is a VEE capsid and the alphavirus glycoprotein is a VEE glycoprotein; and wherein the first and second heterologous promoters both bind to a T7 DNA-dependent RNA polymerase.

8. The recombinant polynucleotide of claim 5, wherein the at least one psRNAV structural protein of the first portion is selected from an alphavirus structural protein, a rubella virus structural protein, a coronavirus structural protein, a dengue virus structural protein, and a Hepatitis C virus structural protein; and the psRNAV replicon of the second portion is selected from an alphavirus replicon, a rubella virus replicon, a coronavirus replicon, a dengue virus replicon, and a Hepatitis C virus replicon.

9. A recombinant polynucleotide of claim 1 wherein the second portion comprises a DNA sequence encoding a replicon-like psRNAV helper RNA sequence operatively linked to a second heterologous promoter.

10. The recombinant polynucleotide of claim 9, wherein the DNA-dependent RNA polymerase of the first portion is selected from a T3, T7, and SP6 DNA-dependent RNA polymerase; wherein the first heterologous promoter is a poxvirus promoter, wherein the replicon-like psRNAV helper RNA sequence of the second portion is an alphavirus helper RNA sequence comprising a sequence encoding an alphavirus structural protein selected from an alphavirus capsid and an alphavirus glycoprotein; and wherein the second heterologous promoter binds to a polymerase selected from T3, T7, and SP6 DNA-dependent RNA polymerase.

11. The recombinant polynucleotide of claim 10, wherein the DNA-dependent RNA polymerase of the first portion is a T7 DNA-dependent RNA polymerase; wherein the poxvirus promoter is a vaccinia virus synthetic early/late promoter; wherein the alphavirus capsid is a VEE capsid and the alphavirus glycoprotein is a VEE glycoprotein; and wherein the second heterologous promoter binds to a T7 DNA-dependent RNA polymerase.

12. The recombinant polynucleotide of claim 9, wherein the psRNAV helper RNA sequence is selected from an alphavirus helper RNA sequence, a rubella virus helper RNA sequence, a coronavirus helper RNA sequence, a dengue virus helper RNA sequence, and a Hepatitis C virus helper RNA sequence.

13. A recombinant DNA polynucleotide comprising: a first portion comprising a DNA sequence encoding a replicon-like psRNAV helper RNA sequence operatively linked to a first heterologous promoter; and a second portion comprising a second heterologous promoter operatively linked to a psRNAV replicon comprising a psRNAV subgenomic promoter operatively linked to a sequence encoding at least one foreign polypeptide.

14. The recombinant polynucleotide of claim 13, wherein the replicon-like psRNAV helper RNA sequence of the first portion is an alphavirus helper RNA sequence comprising a sequence encoding an alphavirus structural protein selected from an alphavirus glycoprotein and an alphavirus capsid; and wherein the first and second heterologous promoters both bind to a polymerase selected from T3, T7, and SP6 DNA-dependent RNA polymerase.

15. The recombinant polynucleotide of claim 14, wherein the alphavirus capsid is a VEE capsid and the alphavirus glycoprotein is a VEE glycoprotein; and wherein the first and second promoters both bind to a T7 DNA-dependent RNA polymerase.

16. The recombinant polynucleotide of claim 13, wherein the psRNAV helper RNA sequence of the first portion is selected from an alphavirus helper RNA sequence, a rubella virus helper RNA sequence, a coronavirus helper RNA sequence, a dengue virus helper RNA sequence, and a Hepatitis C virus helper RNA sequence; and the psRNAV replicon of the second portion is selected from an alphavirus replicon, a rubella virus replicon, a coronavirus replicon, a dengue virus replicon, and a Hepatitis C virus replicon.

17. A recombinant vector comprising a viral vector and the recombinant polynucleotide of any of claims 1–16.

18. A recombinant modified vaccinia virus Ankara (MVA) comprising the recombinant polynucleotide of any of claims 1–16.

19. A psRNAV replicon packaging system comprising:

(a) a recombinant MVA comprising a recombinant polynucleotide comprising: a first portion comprising a sequence encoding a DNA-dependent RNA polymerase operatively linked to a first heterologous promoter; and a second portion comprising a sequence encoding at least one structural protein of a positive-strand RNA virus (psRNAV), but not all of the structural proteins of said psRNAV, operatively linked to a second heterologous promoter, wherein the at least one psRNAV structural protein of the second portion is selected from a psRNAV capsid and a psRNAV glycoprotein; and (b) a recombinant MVA comprising a recombinant polynucleotide comprising: a first portion comprising a sequence encoding at least one structural protein of a psRNAV, but not all of the structural proteins of said psRNAV, operatively linked to a first heterologous promoter; and a second portion comprising a second heterologous promoter operatively linked to a psRNAV replicon comprising an psRNAV subgenomic promoter operatively linked to a sequence encoding at least one foreign polypeptide; wherein the at least one psRNAV structural protein of the first portion is selected from a psRNAV capsid and a psRNAV glycoprotein;

wherein the psRNAV structural protein of (a) and the psRNAV structural protein of (b) are not the same.

20. A psRNAV replicon packaging system comprising:

(a) a recombinant MVA comprising a recombinant polynucleotide comprising: a first portion comprising a sequence encoding a DNA-dependent RNA polymerase operatively linked to a first heterologous promoter; and a second portion comprising a sequence encoding a replicon-like psRNAV helper RNA sequence operatively linked to a second heterologous promoter; wherein the replicon-like psRNAV helper RNA sequence of the second portion is a sequence encoding a psRNAV structural protein selected from a psRNAV capsid and a psRNAV glycoprotein; and (b) a recombinant MVA comprising a recombinant polynucleotide comprising: a first portion comprising a sequence encoding a replicon-like psRNAV helper RNA sequence operatively linked to a first heterologous promoter; and a second portion comprising a second heterologous promoter operatively linked to a psRNAV replicon comprising a psRNAV subgenomic promoter operatively linked to a sequence encoding at least one foreign polypeptide, wherein the replicon-like psRNAV helper RNA sequence of the first portion is a sequence encoding a psRNAV structural protein selected from a psRNAV capsid and a psRNAV glycoprotein;

wherein the psRNAV structural protein of (a) and the psRNAV structural protein of (b) are not the same.

21. A psRNAV replicon packaging system comprising:

(a) a first recombinant vector comprising a recombinant DNA polynucleotide comprising: a first portion comprising a sequence encoding a DNA-dependent RNA polymerase operatively linked to a first heterologous promoter; and a second portion comprising either (i) a sequence encoding at least one structural protein of a positive-strand RNA virus (psRNAV), but not all of the structural proteins of said psRNAV, operatively linked to a second heterologous promoter or (ii) a second portion comprising a DNA sequence encoding a replicon-like psRNAV helper RNA sequence operatively linked to a second heterologous promoter, wherein the at least one psRNAV structural protein of the second portion is selected from a psRNAV capsid and a psRNAV glycoprotein; and (b) a second recombinant vector comprising a recombinant DNA polynucleotide comprising: a first portion comprising a sequence encoding at least one structural protein of a psRNAV, but not all of the structural proteins of said psRNAV, operatively linked to a first heterologous promoter; and a second portion comprising a second heterologous promoter operatively linked to a psRNAV replicon comprising an psRNAV subgenomic promoter operatively linked to a sequence encoding at least one foreign polypeptide, wherein the at least one psRNAV structural protein of the first portion is selected from a psRNAV capsid and a psRNAV glycoprotein;

wherein the psRNAV structural protein of (a) and the psRNAV structural protein of (b) are not the same; and wherein the first recombinant vector and the second recombinant vector are not derived from the same plasmid or virus vector.

22. A kit for obtaining alphavirus replicon particles comprising the recombinant MVA of claim 18.

23. The recombinant vector of claim 17, wherein the recombinant vector is a viral vector selected from poxvirus, adenovirus, herpesvirus, picornavirus, poliovirus, influenza virus, lentivirus, and retrovirus.

24. A recombinant DNA polymycleotide comprising: a first portion comprising a first heterologous promoter operatively linked to a first sequence encoding a psRNAV capsid; and a second portion comprising a second heterologous promoter operatively linked to a second sequence encoding a psRNAV glycoprotein.

25. The recombinant polynucleotide of claim 24, wherein the first and second heterologous promoters are each selected from a poxvirus promoter, a vaccinia virus synthetic early/late promoter, a T7 promoter, a T3 promoter, and an SP6 promoter; and wherein the psRNAV capsid of the first portion is an alphavirus capsid; and wherein the psRNAV glycoprotein of the second portion is an alphavirus glycoprotein.

26. The recombinant polynucleotide of claim 25, wherein the first and second heterologous promoters are both vaccinia virus synthetic early/late promoters; wherein the alphavirus capsid of the first sequence is a VEE capsid; and wherein the alphavirus glycoprotein of the second sequence is a VEE glycoprotein.

27. A recombinant MVA comprising the polynucleotide of any of claims 24–26.

28. A method of amplifying alphavirus replicon particles comprising:

(a) coinfecting a cell with the recombinant MVA of claim 27 and an alphavirus replicon particle;

(b) incubating the coinfected cell under appropriate conditions for the replicon particle to be replicated; and (c) obtaining the amplified replicon particles from the cell.

29. A recombinant polynucleotide of claim 1 wherein the second portion comprises a replicon-like psRNAV helper RNA sequence comprising a reporter gene operatively linked to a second heterologous promoter.

30. The recombinant polynucleotide of claim 29, wherein the DNA-dependent RNA polymerase of the first portion is selected from a T3, T7, or SP6 DNA-dependent RNA polymerase; wherein the first heterologous promoter is a poxvirus promoter; wherein the reporter gene of the second portion is selected from a luciferase gene, a chloramphenicol acetyltransferase (CAT) gene, a beta-galactosidase gene, a beta-glucoronidase gene, a blue fluorescent protein (BFP) gene, a yellow fluorescent protein (YFP) gene, and a green fluorescent protein (GFP) gene; and wherein the second heterologous promoter binds to a polymerase selected from a T3, T7, or SP6 DNA-dependent RNA polymerase.

31. The recombinant polynucleotide of claim 30, wherein the DNA-dependent RNA polymerase of the first portion is a T7 DNA-dependent RNA polymerase; wherein the first heterologous promoter is a vaccinia virus synthetic early/late promoter; wherein the reporter gene of the second portion is a GFP gene; and wherein the second heterologous promoter binds to a T7 DNA-dependent RNA polymerase.

32. The recombinant polynucleotide of claim 20, wherein the psRNAV helper RNA sequence is selected from an alphavirus helper RNA sequence, a rubella virus helper RNA sequence, a coronavirus helper RNA seguence, a dengue virus helper RNA sequence, and a Hepatitis C virus helper RNA sequence.

33. A recombinant MVA comprising the recombinant polynucleotide of any of claims 29–32.

34. A method of determining the titer of a solution of psRNAV replicon particles comprising:
 (a) coinfecting cells with the recombinant MVA of claim 33 and a solution of psRNAV replicon particles;
 (b) incubating the coinfected cells under appropriate conditions for expression of a reporter gene;
 (c) detecting the expression of the reporter gene; and
 (d) determining the titer of the solution of psRNAV replicon particles.

35. A recombinant MVA comprising the polynucleotide of any of claims 1–16, 24–26, or 29–32, wherein the polynucleotide is inserted into deletion I, deletion II, deletion III, deletion IV, deletion V, deletion VI, the sequence encoding hemaglutinin or the sequence encoding thymidine kinase.

36. The method of claim 28, wherein the cell is selected from a BHK-21 cell and a FRhL cell.

37. The method of claim 34, wherein the cells are selected from BHK-21 cells and FRhL cells.

* * * * *

UNITED STATES PATENT AND TRADEMARK OFFICE
CERTIFICATE OF CORRECTION

PATENT NO. : 7,034,141 B2 Page 1 of 1
APPLICATION NO. : 10/363082
DATED : April 25, 2006
INVENTOR(S) : Gerald R. Kovacs et al.

It is certified that error appears in the above-identified patent and that said Letters Patent is hereby corrected as shown below:

Column 39
Line 3 -- replace PSRNAV with psRNAV

Column 42
Line 18 -- replace polymycleotide with polynucleotide

Column 43
Line 4 -- replace claim 20 with claim 29

Signed and Sealed this

Twenty-second Day of August, 2006

JON W. DUDAS
*Director of the United States Patent and Trademark Office*

SEQUENCE LISTING

```
<160> NUMBER OF SEQ ID NOS: 3

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 28
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys
```

-continued

<210> SEQ ID NO 3
<211> LENGTH: 4082
<212> TYPE: DNA
<213> ORGANISM: Human immunodeficiency virus
<220> FEATURE:
<223> OTHER INFORMATION: Description of Artificial Sequence: vector pLW17

<400> SEQUENCE: 3

```
cctcctgaaa aactggaatt taatacacca tttgtgttca tcatcagaca tgatattact      60
ggatttatat tgtttatggg taaggtagaa tctccttaat atgggtacgg tgtaaggaat     120
cattatttta tttatattga tgggtacgtg aaatctgaat tttcttaata aatattattt     180
ttattaaatg tgtatatgtt gttttgcgat agccatgtat ctactaatca gatctattag     240
agatattatt aattctggtg caatatgaca aaaattatac actaattagc gtctcgtttc     300
agacatggat ctgtcacgaa ttaatacttg gaagtctaag cagctgaaaa gctttctctc     360
tagcaaagat gcatttaagg cggatgtcca tggacatagt gccttgtatt atgcaatagc     420
tgataataac gtgcgtctag tatgtacgtt gttgaacgct ggagcattga aaaatcttct     480
agagaatgaa tttccattac atcaggcagc cacattggaa gataccaaaa tagtaaagat     540
tttgctattc agtggactgg atgattcgag gtacccgggg atcctctaga gtcaaccttat     600
tttatgatta tttctcgctt tcaatttaac acaaccctca agaacctttg tatttatttt     660
caatttttag ctgcaggtgg atgcgatcat gacgtcctct gcaatggata caatgaacc      720
taaagtacta gaaatggtat atgatgctac aattttaccc gaaggtagta gcatggattg     780
tataaacaga cacatcaata tgtgtataca acgcacctat agttctagta taattgccat     840
attggataga ttcctaatga tgaacaagga tgaactaaat aatacacagt gtcatataat     900
taaagaattt atgacatacg aacaaatggc gattgaccat tatggagaat atgtaaacgc     960
tattctatat caaattcgta aaagacctaa tcaacatcac accattaatc tgtttaaaaa    1020
aataaaaaga acccggtatg acacttttaa agtggatccc gtagaattcg taaaaaaagt    1080
tatcggattt gtatctatct tgaacaaata taaaccggtt tatagttacg tcctgtacga    1140
gaacgtcctg tacgatgagt tcaaatgttt cattgactac gtggaaacta agtatttcta    1200
aaattaatga tgcattaatt tttgtattga ttctcaatcc taaaaactaa aatatgaata    1260
agtattaaac atagcggtgt actaattgat ttaacataaa aaatagttgt taactaatca    1320
tgaggactct acttattaga tatattcttt ggagaaatga caacgatcaa accgggcatg    1380
caagcttgtc tccctatagt gagtcgtatt agagcttggc gtaatcatgg tcatagctgt    1440
ttcctgtgtg aaattgttat ccgctcacaa ttccacacaa catacgagcc ggaagcataa    1500
agtgtaaagc ctggggtgcc taatgagtga gctaactcac attaattgcg ttgcgctcac    1560
tgcccgcttt cgagtcggga aacctgtcgt gccagctgca ttaatgaatc ggccaacgcg    1620
cggggagagg cggtttgcgt attgggcgct cttccgcttc ctcgctcact gactcgctgc    1680
gctcggtcgt tcggctgcgg cgagcggtat cagctcactc aaaggcggta atacggttat    1740
ccacagaatc aggggataac gcaggaaaga acatgtgagc aaaaggccag caaaaggcca    1800
ggaaccgtaa aaaggccgcg ttgctggcgt ttttcgatag gctccgcccc cctgacgagc    1860
atcacaaaaa tcgacgctca agtcagaggt ggcgaaaccc gacaggacta taaagatacc    1920
aggcgtttcc ccctggaagc tccctcgtgc gctctcctgt tccgaccctg ccgcttaccg    1980
```

-continued

```
gataccctgtc cgcctttctc ccttcgggaa gcgtggcgct ttctcatagc tcacgctgta    2040
ggtatctcag ttcggtgtag gtcgttcgct ccaagctggg ctgtgtgcac gaaccccccg    2100
ttcagcccga ccgctgcgcc ttatccggta actatcgtct tgagtccaac ccggtaagac    2160
acgacttatc gccactggca gcagccactg gtaacaggat tagcagagcg aggtatgtag    2220
gcggtgctac agagttcttg aagtggtggc ctaactacgg ctacactaga aggacagtat    2280
ttggtatctg cgctctgctg aagccagtta ccttcggaaa aagagttggt agctcttgat    2340
ccggcaaaca aaccaccgct ggtagcggtg gtttttttgt ttgcaagcag cagattacgc    2400
gcagaaaaaa aggatctcaa gaagatcctt tgatcttttc tacggggtct gacgctcagt    2460
ggaacgaaaa ctcacgttaa gggattttgg tcatgagatt atcaaaaagg atcttcacct    2520
agatcctttt aaattaaaaa tgaagtttta aatcaatcta agtatatat gagtaaactt    2580
ggtctgacag ttaccaatgc ttaatcagtg aggcacctat ctcagcgatc tgtctatttc    2640
gttcatccat agttgcctga ctccccgtcg tgtagataac tacgatacgg gagggcttac    2700
catctggccc cagtgctgca atgataccgc gagacccacg ctcaccggct ccagatttat    2760
cagcaataaa ccagccagcc ggaagggccg agcgcagaag tggtcctgca actttatccg    2820
cctccatcca gtctattaat tgttgccggg aagctagagt aagtagttcg ccagttaata    2880
gtttgcgcaa cgttgttggc attgctacag gcatcgtggt gtcacgctcg tcgtttggta    2940
tggcttcatt cagctccggt tcccaacgat caaggcgagt tacatgatcc cccatgttgt    3000
gcaaaaaagc ggttagctcc ttcggtcctc cgatcgttgt cagaagtaag ttggccgcag    3060
tgttatcact catggttatg gcagcactgc ataattctct tactgtcatg ccatccgtaa    3120
gatgcttttc tgtgactggt gagtactcaa ccaagtcatt ctgagaatag tgtatgcggc    3180
gaccgagttg ctcttgcccg gcgtcaatac gggataatac cgcgccacat agcagaactt    3240
taaaagtgct catcattgga aaacgttctt cggggcgaaa actctcaagg atcttaccgc    3300
tgttgagatc cagttcgatg taacccactc gtgcacccaa ctgatcttca gcatctttta    3360
ctttcaccag cgtttctggg tgagcaaaaa caggaaggca aaatgccgca aaaaagggaa    3420
taagggcgac acggaaatgt tgaatactca tactcttcct ttttcaatat tattgaagca    3480
tttatcaggg ttattgtctc atgagcggat acatatttga atgtatttag aaaaataaac    3540
aaataggggt tccgcgcaca tttccccgaa aagtgccacc tgacgtctaa gaaaccatta    3600
ttatcatgac attaacctat aaaaataggc gtatcacgag gccctttcgt ctcgcgcgtt    3660
tcggtgatga cggtgaaaac ctctgacaca tgcagctccc ggagacggtc acagcttgtc    3720
tgtaagcgga tgccgggagc agacaagccc gtcagggcgc gtcagcgggt gttggcgggt    3780
gtcgggctg gcttaactat gcggcatcag agcagattgt actgagagtg caccatatgc    3840
ggtgtgaaat accgcacaga tgcgtaagga gaaaataccg catcaggcgc cattcgccat    3900
tcaggctgcg caactgttgg gaagggcgat cggtgcgggc ctcttcgcta ttacgccagc    3960
tggcgaaagg gggatgtgct gcaaggcgat taagttgggt aacgccaggg ttttcccagt    4020
cacgacgttg taaaacgacg gccagtgaat tggatttagg tgacactata gaatacgaat    4080
tc                                                                   4082
```